(12) United States Patent
Kwon et al.

(10) Patent No.: US 12,629,399 B2
(45) Date of Patent: *May 19, 2026

(54) RECOMBINANT HERPES SIMPLEX VIRUS FOR MULTIPLE TARGETING AND USE THEREOF

(71) Applicant: Gencellmed Inc., Seoul (KR)

(72) Inventors: Heechung Kwon, Gyeonggi-do (KR); Hyunjung Baek, Gyeonggi-do (KR)

(73) Assignee: Gencellmed Inc., Seoul (KR)

( * ) Notice: Subject to any disclaimer, the term of this patent is extended or adjusted under 35 U.S.C. 154(b) by 1095 days.

This patent is subject to a terminal disclaimer.

(21) Appl. No.: 17/430,003

(22) PCT Filed: Feb. 19, 2021

(86) PCT No.: PCT/KR2021/002155
§ 371 (c)(1),
(2) Date: Aug. 11, 2021

(87) PCT Pub. No.: WO2021/251589
PCT Pub. Date: Dec. 16, 2021

(65) Prior Publication Data
US 2022/0305066 A1 Sep. 29, 2022

(30) Foreign Application Priority Data

Jun. 12, 2020 (KR) ......................... 10-2020-0071873
Jun. 16, 2020 (KR) ......................... 10-2020-0072979

(51) Int. Cl.
*A61K 35/763* (2015.01)
*A61P 29/00* (2006.01)
(Continued)

(52) U.S. Cl.
CPC ............ *A61K 35/763* (2013.01); *A61P 29/00* (2018.01); *A61P 35/00* (2018.01); *C07K 14/705* (2013.01); *C07K 16/32* (2013.01); *C12N 7/00* (2013.01)

(58) Field of Classification Search
CPC ........ A61K 35/763; A61P 29/00; A61P 35/00; C07K 14/005; C07K 14/705; C07K 16/30;
(Continued)

(56) References Cited

U.S. PATENT DOCUMENTS 11,421,017 B2 * 8/2022 Kwon .................. C07K 16/087
2010/0233758 A1 9/2010 Kwon et al.
(Continued)

FOREIGN PATENT DOCUMENTS

CN 109563490 A 4/2019
KR 10-2009-0028971 A 3/2009
(Continued)

OTHER PUBLICATIONS

Morimoto, T., Arii, J., Akashi, H. and Kawaguchi, Y. (2009), Identification of multiple sites suitable for insertion of foreign genes in herpes simplex virus genomes. Microbiology and Immunology, 53: 155-161. https://doi.org/10.1111/j.1348-0421.2008.00104.x (Year: 2009).*
(Continued)

*Primary Examiner* — Nicole Kinsey White
*Assistant Examiner* — Marlene V Buckmaster
(74) *Attorney, Agent, or Firm* — Harness, Dickey & Pierce, P.L.C.

(57) ABSTRACT

Proposed are a recombinant herpes simplex virus for multiple targeting and the use thereof. Particularly, a recombinant HSV capable of multiple targeting through multiple expression of an adapter, which is a fused protein of a
(Continued)

cancer-cell-targeting domain and an extracellular domain of HVEM, a recombinant HSV capable of multiple targeting by having a modified glycoprotein so as to enable retargeting, in addition to being capable of expressing the adapter that is the fused protein of the cancer-cell-targeting domain and the extracellular domain of HVEM, and the use of the virus for anti-inflammatory therapy are disclosed.

17 Claims, 18 Drawing Sheets

Specification includes a Sequence Listing.

(51) Int. Cl.

| | |
|---|---|
| *A61P 35/00* | (2006.01) |
| *C07K 14/705* | (2006.01) |
| *C07K 16/32* | (2006.01) |
| *C12N 7/00* | (2006.01) |

(58) Field of Classification Search

CPC ............... C07K 16/3007; C07K 16/32; C07K 2317/622; C07K 2319/00; C12N 2710/16621; C12N 2710/16622; C12N 2710/16632; C12N 2710/16643; C12N 2710/16645; C12N 7/00

See application file for complete search history.

(56) References Cited

U.S. PATENT DOCUMENTS

| | | | |
|---|---|---|---|
| 2017/0035818 A1 | 2/2017 | Seymour et al. | |
| 2017/0306415 A1* | 10/2017 | Abu-Yousif | ....... C07K 16/2863 |
| 2018/0002723 A1* | 1/2018 | Campadelli | .......... C12N 15/869 |

FOREIGN PATENT DOCUMENTS

| | | |
|---|---|---|
| KR | 10-2019-0020727 A | 3/2019 |
| WO | WO-2020/113151 A1 | 6/2020 |
| WO | WO-2021/034157 A1 | 2/2021 |

OTHER PUBLICATIONS

Macdonald SJ, Mostafa HH, Morrison LA, Davido DJ. 2012. Genome Sequence of Herpes Simplex Virus 1 Strain Kos. J Virol 86:. https://doi.org/10.1128/jvi.00646-12 (Year: 2012).*

Shibata, T., Uchida, H., Shiroyama, T et al. Development of an oncolytic HSV vector fully retargeted specifically to cellular EpCAM for virus entry and cell-to-cell spread. Gene Ther 23, 479-488 (2016). https://doi.org/10.1038/gt.2016.17 (Year: 2016).*

Nakano et al. "Herpes simplex virus targeting to the EGF receptor by a gD-specific soluble bridging molecule." Mol Ther. 2005; 11(4):617-626. Published Jan. 22, 2005 (Year: 2005).*

Galdiero et al. "Site-directed and linker insertion mutagenesis of herpes simplex virus type 1 glycoprotein H." Journal of virology vol. 71,3 (1997): 2163-70. Published Mar. 1, 1997 (Year: 1997).*

Office Action from corresponding Japanese Patent Application No. 2023-509359, dated Oct. 2, 2023.

Dmitriev, I., et al.; "Ectodomain of Coxsackievirus and Adenovirus Receptor Genetically Fused to Epidermal Growth Factor Mediates Adenovirus Targeting to Epidermal Growth Factor Receptor-Positive Cells", Journal of Virology, Aug. 2000, p. 6875-6884.

Hemminki, A., et al.; "Targeting Oncolytic Adenoviral Agents to the Epidermal Growth Factor Pathway with a Secretory Fusion Molecule1", Cancer Research 61, 6377-6381, Sep. 1, 2001.

Hemminki, A., et al.; "Production of an EGFR targeting molecule from a conditionally replicating adenovirus impairs its oncolytic potential", Cancer Gene Therapy (2003) 10, 583-588.

Baek, H., et al.; "Bispecific Adapter-Mediated Retargeting of a Receptor-Restricted HSV-1 Vector to CEA-Bearing Tumor Cells". Molecular Therapy vol. 19 No. 3, 507-514 Mar. 2011.

Notice of Allowance from corresponding Korean Patent Application No. 10-2021-0022781, issued on Jul. 1, 2022.

Menotti, L., et al.; "HSV as A Platform for the Generation of Retargeted, Armed, and Reporter-Expressing Oncolytic Viruses", Viruses 2018, 10, 352, pp. 1-29.

Examination Report from corresponding Australian Patent Application No. 2021287536, dated Sep. 18, 2024.

Menotti, L., et al.; "Inhibition of human tumor growth in mice by an oncolytic herpes simplex virus designed to target solely HER-2-positive cells", PNAS, Jun. 2, 2009, vol. 106, No. 22, pp. 9039-9044.

Office Action from corresponding Chinese Patent Application No. 202180038288.X, dated Feb. 7, 2025.

Extended European Search Report from corresponding European Patent Application No. 21777612.9, dated Jul. 5, 2024.

Valentina Gatta et al: "The Engineering of a Novel Ligand in gH Confers to HSV an Expanded Tropism Independent of gD Activation by Its Receptors", PLOS Pathogens, vol. 11, No. 5, May 21, 2015, pp. 1-18.

William F Goins et al: "Retargeting of herpes simplex virus (HSV) vectors", Current Opinion in Virology, vol. 21, Sep. 7, 2016 (Sep. 7, 2016), pp. 93-101.

J C Whitbeck et al: "Glycoprotein D of 1-15 herpes simplex virus (HSV) binds directly to HVEM, a member of the tumor necrosis factor receptor superfamily and a mediator of HSV entry", Journal of Virology, Aug. 1, 1997 (Aug. 1, 1997), pp. 6083-6093.

* cited by examiner gD: NI (R222N/F2231)

HVEM-restricted gD mutant gD: NI
(R222N/F2231)

HVEM-restricted gD mutant

J1    J-HVEM    J-Nectin

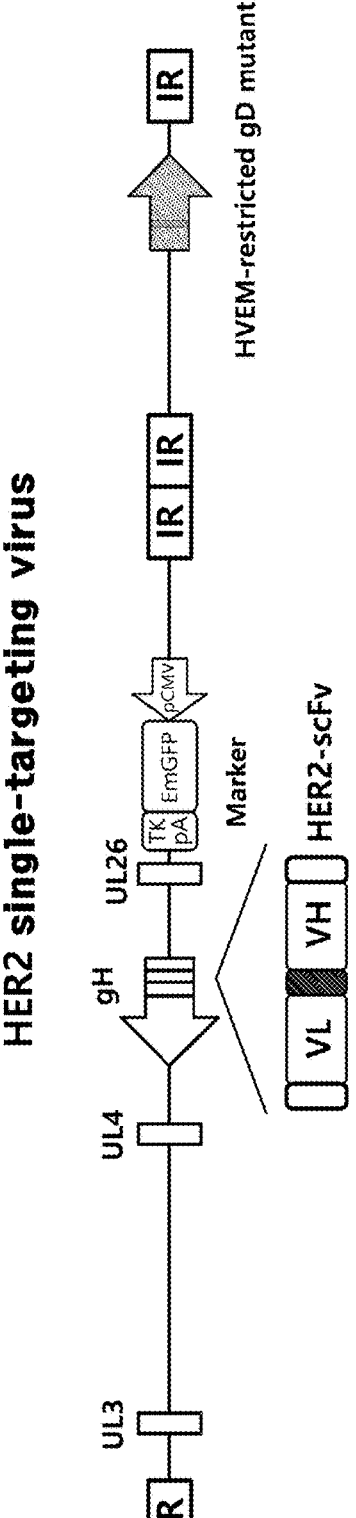
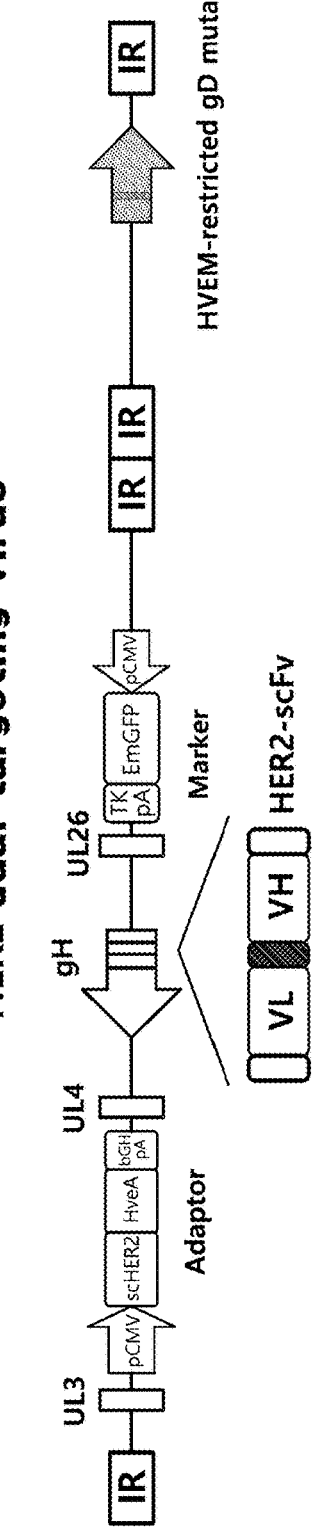
FIG. 7

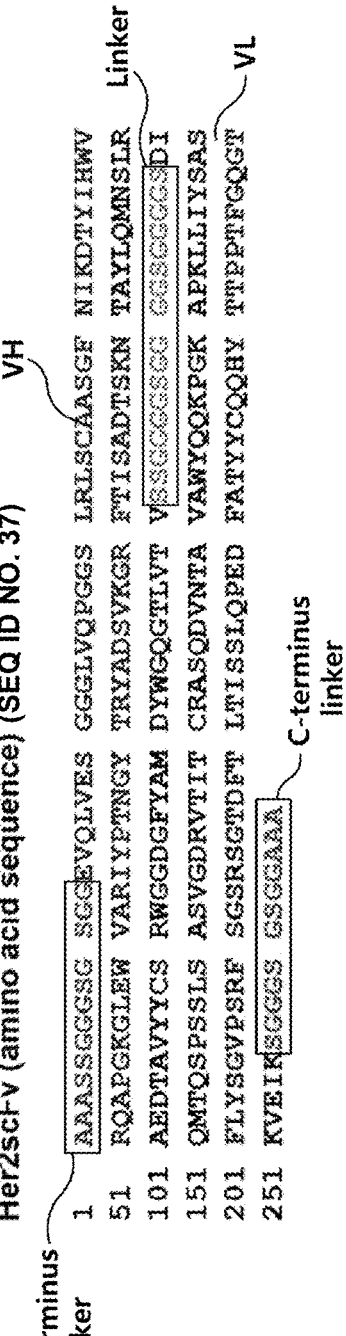

Her2scFv (amino acid sequence) (SEQ ID NO. 37)

N-terminus linker

VH

Linker

C-terminus linker

VL

1    AAASSGGGSG    SGGEVQLVES    GGGLVQPGGS    LRLSCAASGF    NIKDTYIHWV
51   RQAPGKGLEW    VARIYPTNGY    TRYADSVKGR    FTISADTSKN    TAYLQMNSLR
101  AEDTAVYYCS    RWGGDGFYAM    DYWGQGTLVT    VSSGGGGSGG    GGSGGGGSDI
151  QMTQSPSSLS    ASVGDRVTIT    CRASQDVNTA    VAWYQQKPGK    APKLLIYSAS
201  FLYSGVPSRF    SGSRSGTDFT    LTISSLQPED    FATYYCQQHY    TTPPTFGQGT
251  KVEIKSGGGS    GSGGAAA

FIG. 8

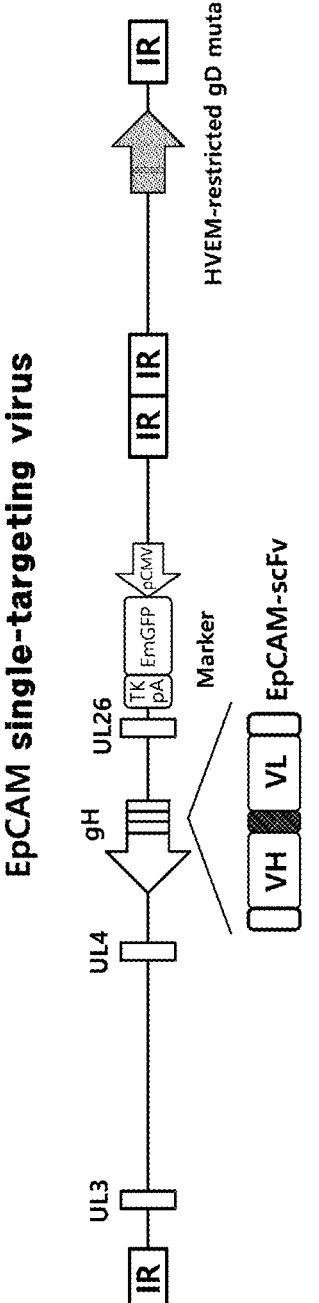
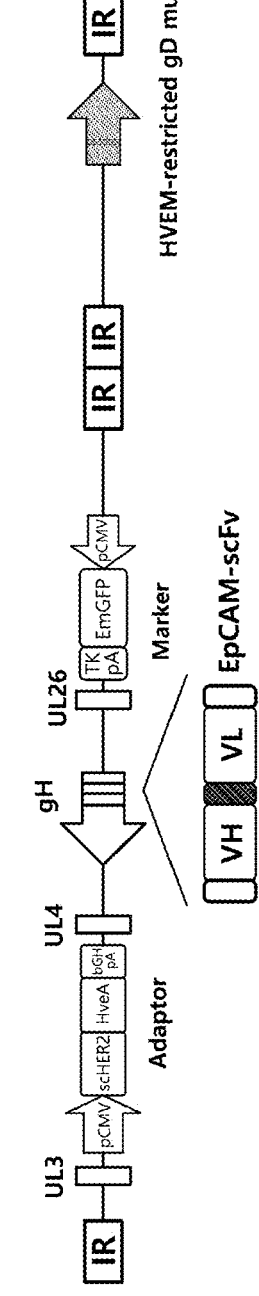
FIG. 9

RECOMBINANT HERPES SIMPLEX VIRUS FOR MULTIPLE TARGETING AND USE THEREOF

CROSS-REFERENCE TO RELATED APPLICATIONS

This application is a national phase application of PCT Application No. PCT/KR2021/002155, filed on Feb. 19, 2021, which claims priority to Korean Patent Application Nos. 10-2020-0072979, filed on Jun. 16, 2020 and 10-2020-0071873 filed on Jun. 12, 2020. The entire disclosure of the applications identified in this paragraph is incorporated herein by reference.

SEQUENCE LISTING

This application contains references to amino acid sequences and/or nucleic acid sequences which have been submitted herewith as the sequence listing text file entitled "000022usnp_SequenceListing_ST25.txt", file size 65,536 bytes, created on 24 Apr. 2025. The aforementioned sequence listing is hereby incorporated by reference in its entirety pursuant to 37 C.F.R. § 1.52 (e).

TECHNICAL FIELD

The present disclosure relates to a recombinant herpes simplex virus for multiple targeting, and to the use thereof.

BACKGROUND ART

In the treatment of cancer, surgical therapy, anticancer chemotherapy, radiotherapy, and the like have been widely used to date, but most of these are characterized by side effects, incomplete treatment effects, and problems such as cancer recurrence and metastasis. Therefore, the development of new and effective cancer therapies is continually required, and in recent years, rapid advancements have been made in the field of anticancer immunotherapy, examples of which include oncolytic virus therapy, chimeric antigen receptor T (CAR-T) cell therapy, and the like.

In anticancer immunotherapy, an oncolytic virus is a virus imparted with the ability to lyse cancer cells through manipulation of the genes of a living virus and selective propagation thereof in cancer cells, and propagation thereof in normal cells is limited. The virus released by lysis of cancer cells is able to continuously infect surrounding cancer cells, thereby providing a continuous and synergistic therapeutic effect. Moreover, the oncolytic virus is capable of increasing the anticancer effect by stimulating the immune response of the human body by releasing an immunogenic tumor antigen in the process of lysing cancer cells. Furthermore, such anticancer effects may be enhanced through artificial manipulation so as to express cytokines, chemokines, and the like.

Currently developed oncolytic viruses may be classified into 10 or more types, including adenovirus, herpes simplex virus (HSV), vaccinia virus, etc. Among these, HSV is an enveloped icosahedral virion containing linear double-stranded DNA having a size of 152 kb, and includes HSV-1 and HSV-2 types. HSV has many non-essential genes, and the genome size thereof is large, making it easy to use to manipulate or transport external genes, and the replication cycle thereof is short, and moreover, HSV has high infection efficiency, and is desirably capable of exhibiting improved cancer-cell-targeting efficiency through easy manipulation of glycoproteins involved in cell attachment and infection.

HSV is a virus having an envelope, and the entry of HSV into cells is achieved through complex interactions involving gD, gB, gH/gL and gC glycoproteins present in the envelope thereof. First, when gB and gC are attached to 3-O-S HS (3-O-sulfated heparan sulfate) on the cell surface, gD binds to at least one receptor among cell receptors such as HVEM (herpesvirus entry mediator, HveA), nectin-1 (HveC), and nectin-2 (HveB) to thus induce fusion between the virus and the cell membrane, whereby HSV enters the cells (Hiroaki Uchida et al., Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83 (7): 2951-61).

T-VEC (talimogene laherparepvec, product name: Imlygic), approved by the US FDA in October 2015, is an oncolytic viral therapeutic agent for malignant melanoma using HSV-1. T-VEC is an attenuated HSV-1 virus from which ICP34.5 and ICP47 genes are deleted to attenuate the pathogenicity thereof and which expresses GM-CSF (granulocyte-macrophage-colony-stimulating factor) to promote the human immune response. However, T-VEC has a drawback in that the therapeutic efficacy thereof is low due to the limited viral propagation thereof, attributed to the loss of some genes.

In order to overcome such limitations, attempts have been made to perform retargeting to specifically target cancer cells by manipulating the envelope glycoproteins gD, gB, gH, and gC, which are involved in the entry of HSV into cells, without weakening the virus. This retargeting is the introduction of an exogenous sequence encoding a targeting domain for a cancer cell target molecule into the glycoprotein gD, gB, gH, or gC sequence, and uses a recombinant virus having a chimeric glycoprotein in which a targeting domain (also called a ligand) of an exogenous sequence is inserted into the glycoprotein, rather than a wild-type glycoprotein. Such a recombinant virus is capable of entering cancer cells having a target molecule that is specifically recognized and bound by the targeting domain. The targeting domain is typically an scFv (single-chain variable fragment), and the target molecules that are currently retargeted are EpCAM (epithelial cell adhesion molecule), HER2 (human epidermal growth factor receptor 2), etc., and gB, gH, gC and the like, as glycoproteins, have been modified.

Meanwhile, among the cell receptors of HSV, HVEM belongs to the tumor necrosis factor receptor protein family (TNFR family), and is mainly expressed in T/B lymphocytes, macrophages, DC cells, sensory neurons, and mucosal epithelial cells (Shui J. W., Kronenberg M. 2013. Gut Microbes 4 (2): 146-151), but is known to be expressed in abundance in various tumor tissues such as B/T lymphoma, melanoma, colorectal cancer, hepatocellular carcinoma, breast cancer, ovarian serous adenocarcinoma, clear renal cell carcinoma, and glioblastoma (Pasero C. et al., Curr. Opin. Pharmacol. 2012. 2 (4): 478-85, Malissen N. et al., ONCOIMMUNOLOGY 2019, VOL. 8 (12): e1665976). HVEM has four CRDs (cysteine-rich domains), which are the feature of the TNFR family, and two of four CRDs are linked with gD of HSV to thus induce the entry of HSV-1 and HSV-2 into cells (Sarah A Connolly et al., Structure-based Analysis of the Herpes Simplex Virus Glycoprotein D Binding Site Present on Herpesvirus Entry Mediator HveA (HVEM). J. Virol. 2002 November; 76 (21): 10894-904).

As already reported by the inventors of the present disclosure, a fused protein (CEAscFv-HveA) of scFv (single-chain variable fragment) for CEA (carcinoembryonic antigen) and an extracellular domain of HVEM, which is one of the HSV cell surface receptors, is manufactured, and when the fused protein is used along with HSV to treat a cell line expressing CEA, the fused protein acts as an adapter to induce HSV to target and infect the corresponding cell line (Korean Patent No. 10-0937774 and U.S. Pat. No. 8,318,662).

The inventors of the present disclosure have ascertained that, when a gene encoding a fused protein (HER2scFv-HveA, EpCAM2scFv-HveA), which is an adapter capable of targeting HER2 (human epidermal growth factor receptor 2) or EpCAM, is inserted into the genome of HSV so that the fused protein is expressed in cells infected with HSV, the fused protein acts to induce HSV to target and infect a cell line expressing HER2 or EpCAM. Moreover, it is confirmed that, in order to enable multiple targeting using an adapter, when an expression cassette capable of expressing the fused protein (HER2scFv-HveA), which is an adapter having a targeting function for HER2, and an expression cassette capable of expressing the fused protein (EpCAM-HveA), which is an adapter having a targeting function for EpCAM, are subjected to dual insertion into the HSV genome so that the fused proteins are expressed in HSV-infected cells, the fused proteins are confirmed to induce an HSV virion to infect cell lines expressing HER2 and/or EpCAM through multiple targeting. In addition, it is confirmed that a recombinant HSV, which enables retargeting to HER2 and/or EpCAM by inserting the expression cassette of such an adapter into the genome of HSV and further modifying the glycoprotein, infects cell lines expressing HER2 and/or EpCAM through multiple targeting.

SUMMARY

Technical Problem

Therefore, the present disclosure has been made keeping in mind the problems encountered in the related art, and an objective of the present disclosure is to provide a recombinant HSV capable of multiple targeting through multiple expression of an adapter, which is a fused protein of a cancer-cell-targeting domain and an extracellular domain of HVEM.

Another objective of the present disclosure is to provide a recombinant HSV capable of multiple targeting by having a modified glycoprotein so as to enable retargeting, in addition to being able to express an adapter that is a fused protein of a cancer-cell-targeting domain and an extracellular domain of HVEM.

Still another objective of the present disclosure is to provide a pharmaceutical composition for treating cancer containing the recombinant HSV as an active ingredient.

Yet another objective of the present disclosure is to provide a method of preventing or treating cancer including administering the pharmaceutical composition to a subject such as a patient in an effective amount.

Other or specific objectives of the present disclosure will be set forth below.

Technical Solution

An aspect of the present disclosure pertains to a recombinant HSV capable of multiple targeting. In an exemplary aspect, the recombinant HSV capable of multiple targeting according to the present disclosure may be configured such that at least one expression cassette expressing a fused protein (i.e. an adapter) of a cancer-cell-targeting domain (i.e. a domain that specifically binds to a target molecule on the surface of a cancer cell) and an extracellular domain of HVEM is inserted into the genome of a herpes simplex virus so as to express the fused protein in two or more ways, that is, multiple ways without inhibiting the propagation of the herpes simplex virus.

In the recombinant HSV for multiple targeting according to the present disclosure, a fused protein is expressed in two or more ways, that is, multiple ways, whereby the targeting domain of the fused protein that is expressed in multiple ways is able to target the same target molecule in multiple ways or to target different target molecules in multiple ways. The target molecule is any antigen or any receptor present on the surface of a cancer cell that the targeting domain of the fused protein specifically recognizes and binds. The recombinant HSV of the present disclosure may be configured such that at least one expression cassette capable of multiple expression of a fused protein that is able to target a target molecule, for example, HER2, is inserted into the genome thereof or such that at least one expression cassette capable of expressing a fused protein that is able to target each of different target molecules, for example, HER2 and EpCAM, is inserted into the genome thereof.

When the recombinant HSV of the present disclosure infects target cells, which are cancer cells, and enters the target cells, HSV proliferates, and the adapter, which is the fused protein, is expressed in two or more ways, that is, multiple ways in the cells and is released to the outside of the cells along with the proliferated HSV virion upon cell lysis. Alternatively, in the case in which the adapter has a leader sequence, it may be released even before virion release due to cell lysis. Then, the adapter, which is expressed in multiple ways, is released to the outside of the cells and acts to induce the HSV virion in multiple ways to infect surrounding cancer cells expressing a target molecule recognized by the cancer-cell-targeting domain of the adapter. Thereby, compared to a single-targeting recombinant HSV (i.e. a recombinant HSV containing only one expression cassette capable of expressing a fused protein of a cancer-cell-targeting domain and an extracellular domain of HVEM), the infection efficiency thereof is further increased, and the efficiency of continuous proliferation to surrounding cancer cells is further increased, ultimately leading to more effective cancer cell death.

In another exemplary aspect, the recombinant HSV capable of multiple targeting according to the present disclosure may be a recombinant HSV capable of multiple targeting (i) in which at least one expression cassette capable of expressing an adapter, which is a fused protein of a cancer-cell-targeting domain and an extracellular domain of HVEM, is inserted into the genome of a herpes simplex virus without inhibiting the propagation of the herpes simplex virus, and (ii) in which a cancer-cell-targeting domain is inserted and fused into the glycoprotein thereof.

The recombinant HSV for multiple targeting according to the present disclosure has a modified glycoprotein capable of retargeting through insertion and fusion of the cancer-cell-targeting domain, thereby enabling additional targeting by the glycoprotein, in addition to targeting by the adapter. Like the recombinant HSV having the expression cassette capable of expressing the adapter in multiple ways as described above, the recombinant HSV for multiple targeting is more effective for the efficiency of infection of cancer cells with the virion, continuous proliferation of the virion to surrounding cancer cells, and cancer cell death.

In general, a recombinant HSV is HSV that is genetically manipulated so as to be capable of losing or altering certain functions or expressing a target protein of interest by introducing an artificial mutation (through deletion, substitution or insertion of some nucleic acid sequences) compared to a wild-type HSV. In the present disclosure, the recombinant HSV is HSV capable of expressing an adapter in infected cancer cells and provided with a modified glycoprotein for retargeting, by introducing (i.e. inserting) an adapter-expressing cassette (i.e. a construct in which the adapter gene is operably linked with a promoter sequence that enables expression thereof and a polyadenylation signal sequence) into the HSV genome without inhibiting the propagation of HSV.

Recombinant virus production techniques such as genetic manipulation of viruses and production of virions are well known in the art, and reference may be made to Sandri-Goldin R. M. et al. [Alpha Herpesviruses: Molecular and Cellular Biology, Caister Academic Press, 2006], Robin H. Lachmann [Herpes simplex virus-based vectors, Int. J. Exp. Pathol. 2004 August; 85 (4): 177-190], and the like. All documents cited in the present specification, including the above documents, are considered part of the present specification.

In particular, in addition to being manipulated to express the adapter, the recombinant HSV of the present disclosure may be further manipulated to enter cells only through an HVEM receptor, as an entry receptor, rather than nectin-1. In the following examples of the present disclosure, the sequence of the HSV envelope glycoprotein gD is manipulated to allow HSV to enter cells only through the HVEM receptor. Specifically, arginine (R) at position 222 of gD and phenylalanine (F) at position 223 of gD are substituted with asparagine (N) and isoleucine (I), respectively, so the function of gD is altered. The recombinant HSV having the gD function thus altered may enter host cells only through the HVEM (HveA) receptor (Hiroaki Uchida et al., Generation of Herpesvirus Entry Mediator (HVEM)-restricted Herpes Simplex Virus Type 1 Mutant Viruses: Resistance of HVEM-expressing Cells and Identification of Mutations That Rescue nectin-1 Recognition. J. Virol. 2009 April; 83 (7): 2951-61). The HVEM (HveA) receptor is seldom present in normal cells, and is present only in lymphomas, etc., whereas nectin-1 is usually present in normal cells, so the recombinant HSV having the altered gD function, which may enter cells only through the HVEM receptor, rather than the nectin-1 receptor, does not infect normal cells, and is thus advantageous from the aspect of safety.

In addition, the recombinant HSV of the present disclosure is manipulated to enable additional targeting through insertion and fusion of a cancer-cell-targeting domain into a glycoprotein, in addition to targeting through the adapter. The glycoprotein that is capable of being used for additional targeting may include gB, gC, gH, or the like, and HSV in which a cancer-cell-targeting domain is inserted and fused into a glycoprotein may be manufactured by deleting or not deleting some genes of the glycoprotein and inserting the gene for the cancer-cell-targeting domain into an open reading frame. In the case in which the gene of the cancer-cell-targeting domain is inserted into such a glycoprotein gene, the cancer-cell-targeting domain is integrated into the envelope of a virion when the recombinant HSV is produced in the cells in the state of being fused to the glycoprotein.

Insertion and fusion of the cancer-cell-targeting domain into the glycoprotein may occur in the glycoprotein, such as gB, gC, gD, gH, or the like, at any position of the amino acid sequence from which the amino acid sequence of the glycoprotein is not deleted, at a position from which an amino acid sequence having some length (particularly 1 to 40 contiguous amino acids) is deleted, or at any position of the amino acid sequence from which an amino acid sequence is not deleted or substituted despite the deletion or substitution of an amino acid sequence having some length. Here, the deletion or substitution of the amino acids having some length may be carried out in order to inactivate the binding site of the glycoprotein to a specific cell receptor such as HVEM, nectin-1, or the like.

When the cancer-cell-targeting domain is inserted and fused into the gB glycoprotein, the position thereof may be any position including the N-terminus, but in HSV-1, a preferred position may be any position within the region of amino acids 9 to 896 in the amino acid sequence of gB (SEQ ID NO: 1, GenBank Accession No. ASM47779). In addition, a preferred position may be any position within the region of amino acids 31 to 78, any position within the region of amino acids 80 to 363, or any position within the region of amino acids 408 to 896. In addition, a preferred position may be a position after amino acid 43, a position after amino acid 52, a position after amino acid 70, a position after amino acid 76, a position after amino acid 80, a position after amino acid 81, a position after amino acid 95, a position after amino acid 100, a position after amino acid 137, a position after amino acid 185, a position after amino acid 187, a position after amino acid 241, a position after amino acid 261, a position after amino acid 265, a position after amino acid 304, a position after amino acid 334, a position after amino acid 361, a position after amino acid 408, a position after amino acid 419, a position after amino acid 430, a position after amino acid 458, a position after amino acid 470, a position after amino acid 481, a position after amino acid 495, a position after amino acid 497, a position after amino acid 546, a position after amino acid 608, a position after amino acid 630, a position after amino acid 663, a position after amino acid 664, a position after amino acid 665, a position after amino acid 671, a position after amino acid 673, a position after amino acid 690, a position after amino acid 725, a position after amino acid 730, a position after amino acid 732, a position after amino acid 742, a position after amino acid 772, a position after amino acid 868, a position after amino acid 869, a position after amino acid 886, a position after amino acid 893, a position after amino acid 894, or a position after amino acid 895 of gB. Here, the position is based on the amino acid sequence of SEQ ID NO: 1 of gB, but in the case of a mutant strain having some differences in the sequence of gB, it is based on a homologous sequence corresponding thereto.

When the cell-targeting domain is additionally inserted and fused into the gC glycoprotein, the position thereof may be any position including the N-terminus, but in HSV-1, a preferred position may be any position within the region of amino acids 1 to 442 in the amino acid sequence of gC (SEQ ID NO: 2, GenBank Accession No. ASM47796), and moreover, a preferred position may be any position within the region of amino acids 33 to 154. In addition, a preferred position may be a position after amino acid 33, a position after amino acid 82, a position after amino acid 148, a position after amino acid 149, or a position after amino acid 153 of gC. Here, the position is based on the amino acid sequence of SEQ ID NO: 2 of gC, but in the case of a mutant strain having some differences in the sequence of gC, it is based on a homologous sequence corresponding thereto.

When the cancer-cell-targeting domain is inserted and fused into the gH glycoprotein, the position thereof may be any position including the N-terminus, the N-terminus of the H1A domain, or the like, but in HSV-1, a preferred position may be a position within the region of amino acids 12 to 88, a position within the region of amino acids 116 to 137, or a position within the region of amino acids 209 to 839 in the amino acid sequence of gH (SEQ ID NO: 3, GenBank Accession No. ASM47773). In addition, a preferred position may be a position within a region of amino acids 12 to 49 or a position within a region of amino acids 116 to 137. In addition, a preferred position may be a position after amino acid 12, a position after amino acid 22, a position after amino acid 23, a position after amino acid 29, a position after amino acid 83, a position after amino acid 116, a position after amino acid 209, a position after amino acid 215, a position after amino acid 225, a position after amino acid 277, a position after amino acid 386, a position after amino acid 437, a position after amino acid 447, a position after amino acid 472, a position after amino acid 636, a position after amino acid 637, a position after amino acid 666, a position after amino acid 731, a position after amino acid 763, a position after amino acid 764, a position after amino acid 775, a position after amino acid 806, a position after amino acid 824, or a position after amino acid 838. Here, the position is based on the amino acid sequence of SEQ ID NO: 3 of gH, but in the case of a mutant strain having some differences in the sequence of gH, it is based on a homologous sequence corresponding thereto.

For more specific information on the preferred insertion site of the glycoprotein, reference may be made to JOHN R. GALLAGHER et al. [Functional Fluorescent Protein Insertions in Herpes Simplex Virus gB Report on gB Conformation before and after Execution of Membrane Fusion, PLOS Pathog., 2014 September 18, 10 (9): e1004373], Gatta V. et al. [The Engineering of a Novel Ligand in gH Confers to HSV an Expanded Tropism Independent of gD Activation by Its Receptors, PLOS Pathog. 2015 May 21; 11 (5): e1004907], Tina M. Cairns et al. [Structure-Function Analysis of Herpes Simplex Virus Type 1 gD and gH-gL: Clues from gDgH Chimeras, JOURNAL OF VIROLOGY, June 2003, p. 6731-6742], E. U. Lorentzen et al. [Replication-Competent Herpes Simplex Virus Type 1 Mutant Expressing an Autofluorescent Glycoprotein H Fused protein, Intervirology 2001; 44:232-242], Qing Fan et al. [Differential Effects on Cell Fusion Activity of Mutations in Herpes Simplex Virus 1 Glycoprotein B (gB) dependent on Whether a gD Receptor or a gB Receptor Is Overexpressed, JOURNAL OF VIROLOGY, August 2009, 83 (15): 7384-7390], Erick Lin et al. [Random linker-insertion mutagenesis to identify functional domains of herpes simplex virus type 1 glycoprotein B, Proc. Natl. Acad. Sci. USA. August 2007, 104 (32): 13140-13145], Julia O. Jackson et al. [Insertion Mutations in Herpes Simplex Virus 1 Glycoprotein H Reduce Cell Surface Expression, Slow the Rate of Cell Fusion, or Abrogate Functions in Cell Fusion and Viral Entry, JOURNAL OF VIROLOGY, February 2010, 84 (4): 2038-2046], Guoying Zhou et al. [Engineered herpes simplex virus 1 is dependent on IL13R*2 receptor for cell entry and independent of glycoprotein D receptor interaction, Proc. Natl. Acad. Sci. USA. November 2002, 99 (23): 15124-15129], A R Frampton Jr. et al. [HSV trafficking and development of gene therapy vectors with applications in the nervous system, Gene Therapy, 2005, 12:891-901], Paola Grandi et al. [HSV-1 Virions Engineered for Specific Binding to Cell Surface Receptors, MOLECULAR THERAPY, March 2004, 9 (3): 419-427], William F Goins et al. [Retargeting of Herpes Simplex Virus (HSV) Vectors, Curr. Opin. Virol., 2016 Dec. 21:93-101], Xiaodan Wang et al. [Targeted gene transfer to nigrostriatal neurons in the rat brain by helper virus-free HSV-1 vector particles that contain either a chimeric HSV-1 glycoprotein C-GDNF or a gC-BDNF protein, Brain Res. Mol. Brain Res. 2005 September, 139 (1): 88-102], and the like.

When the cancer-cell-targeting domain is inserted and fused into the glycoprotein, a linker peptide may be present at the N-terminus and the C-terminus of the cancer-cell-targeting domain. The linker peptide is intended to ensure a distance between the cancer-cell-targeting domain and the glycoprotein so that the cancer-cell-targeting domain fused to the glycoprotein does not interfere with the formation of the inherent three-dimensional structure thereof due to fusion with the glycoprotein. The linker peptide may be a linker peptide having any length and any sequence, so long as it has the ability to specifically bind to the target molecule. Taking into consideration flexibility, solubility, and resistance to proteolysis, the linker preferably comprises at least one amino acid selected from among amino acids such as Ser, Gly, Ala, Thr and the like, and the length thereof may be 1 to 30 amino acids, preferably 3 to 25 amino acids, and more preferably 8 to 20 amino acids.

The recombinant HSV of the present disclosure may be mutated so that non-essential genes that are not required for the propagation of HSV (i.e. survival and replication) are deleted, or so that the function thereof is not exhibited (i.e. transcription or translation is interrupted). Specific examples of the non-essential genes may include a UL3 gene (e.g. GenBank Accession No. AFE62830.1), a UL4 gene (e.g. GenBank Accession No. AFE62831.1), a UL14 gene (e.g. GenBank Accession No. AFE62841.1), a UL16 gene (e.g. GenBank Accession No. AFE62843.1), a UL21 gene (e.g. GenBank Accession No. AFE62848.1), a UL24 gene (e.g. GenBank Accession No. AFE62851.1), a UL31 gene (e.g. GenBank Accession No. AFE62859.1), a UL32 gene (e.g. GenBank Accession No. AFE62860.1), a US3 gene (e.g. GenBank Accession No. AFE62891.1), a UL51 gene (e.g. GenBank Accession No. AFE62880.1), a UL55 gene (e.g. GenBank Accession No. AFE62884.1), a UL56 gene (e.g. GenBank Accession No. AFE62885.1), a US2 gene (e.g. GenBank Accession No. AFE62890.1), a US12 gene (e.g. GenBank Accession No. AFE62901.1; ICP47 gene), a LAT gene (e.g. GenBank Accession No. JQ673480.1), a gB gene (e.g. the sequence between 52996 and 55710 of GenBank Accession No. GU734771.1), a gL gene (e.g. GenBank Accession No. AFE62828.1), a gH gene (e.g. GenBank Accession No. AFE62849.1), a gD gene (e.g. GenBank Accession No. AFE62894.1), and the like.

For more specific information on the non-essential genes of HSV, reference may be made to D. M. Knipe and P. M. Howley (eds.) [Fields Virology (vol. 2) Lippincott Williams & Wilkins, Philadelphia, Pa. 2001. pp. 2399-2460)], Subak-Sharpe J. H. and Dargan D. J. [HSV Molecular Biology: General Aspects of Herpes Simplex Virus Molecular Biology Virus Genes, 1998, 16 (3): 239-251], Travis J. Taylor and David M. Knipe [Proteomics of Herpes Simplex Virus Replication Compartments: Association of Cellular DNA Replication, Repair, Recombination, and Chromatin-Remodeling Proteins with ICP8, J. Virol. 2004 June; 78 (11): 5856-5866], and the like.

The recombinant HSV of the present disclosure may be a recombinant HSV-1 virus, a recombinant HSV-2 virus, or an HSV-1/HSV-2 chimeric virus (i.e. a recombinant HSV in which the genome contains both DNA derived from HSV-1 and DNA derived from HSV-2), preferably a recombinant HSV-1 virus, and more preferably a recombinant HSV-1 derived from an HSV-1 KOS strain. The HSV-1 KOS strain is available from ATCC (Cat No VR-1493TM), and the entire genome sequence of the strain is completely analyzed and represented in GenBank Accession No. JQ673480.1 (Stuart J. Macdonald et al. Genome Sequence of Herpes Simplex Virus 1 Strain KOS. J. Virol. 2012 June; 86 (11): 6371-2).

The genome of the HSV-1 virus is composed of 152 kb double-stranded linear DNA encoding a total of 84 genes comprising two fragments connected to each other, particularly a long fragment (L region) and a short fragment (S region). The long fragment (L region) accounts for about 82% of the genome, and the short fragment (S region) accounts for about 18% of the genome, and the long and short fragments are joined by two IRLs (intermediate inverted repeat sequences), which are junction regions, and a TRL (terminal inverted repeat segment) is present at the end of each fragment. The L region (UL) comprises 56 UL1-UL56 genes and 10 genes (UL8.5, 9.5, 10.5, 12.5, 15.5, 20.5, 26.5, 27.5, 43.5, and 49.5), the S region (US) comprises 12 US1-US12 genes and 2 genes (US1.5 and 8.5), and two IRLs, which are junction regions, comprise 4 genes (ICP4, ICP34.5, ICPO, and LAT).

In the present disclosure, the adapter-expressing cassette is configured such that the adapter gene is operably linked with a promoter sequence that enables expression thereof and a polyadenylation signal sequence, which is a transcription termination signal sequence. Here, "operably linked" means linkage that enables transcription and/or translation of the expressed adapter gene. For example, when any promoter affects the transcription of the adapter gene linked thereto, the promoter is said to be operably linked to the adapter gene.

Typically, a promoter is a nucleic acid sequence having a function of controlling transcription of one or more genes, is located at the upstream (5' side) of the transcription start site of a gene, and includes a site for binding to a DNA-dependent RNA polymerase, a transcription start site, a transcription-factor-binding site, and the like. In the case of eukaryotic origin, the promoter includes a TATA box upstream of the transcription start site (usually located at positions −20 to −30 with respect to the transcription start site (+1)), a CAAT box (usually located at position −75 with respect to the transcription start site), an enhancer, a transcription-factor-binding site, and the like.

So long as the promoter is able to express a target gene linked thereto, all of a constitutive promoter (which induces gene expression at all times), an inducible promoter (which induces expression of a target gene in response to a specific external stimulus), a tissue-specific promoter (which induces gene expression in specific tissues or cells), a tissue-non-specific promoter (which induces gene expression in all tissues or cells), an endogenous promoter (which is derived from virus-infected cells), and an exogenous promoter (which is derived from cells other than virus-infected cells) may be used. Many promoters are known in the art, and an appropriate promoter may be selected therefrom and used. For example, useful are a CMV (cytomegalovirus) promoter, a RSV (Rous sarcoma virus) promoter, an HSV (herpes simplex virus) TK (thymidine kinase) promoter, an adenovirus late promoter, a vaccinia virus 75K promoter, an SV40 promoter, a metallothionein promoter, a CD45 promoter (hematopoietic-stem-cell-specific promoter), a CD14 promoter (monocyte-specific promoter), and a cancer-cell-specific promoter (tumor-specific promoter) such as Survivin, Midkine, TERT, CXCR4, etc. In particular, when a cancer-cell-specific promoter is used, the expression of the adapter is induced only in the cancer cells, thus suppressing adapter expression in normal cells, thereby increasing the safety of the recombinant HSV of the present disclosure.

The adapter-expressing cassette is configured to include a transcription termination signal sequence in addition to the promoter, and the transcription termination signal sequence is a sequence that acts as a poly (A) addition signal (poly-adenylation signal) to increase the integrity and efficiency of transcription. Many transcription termination signal sequences are known in the art, and an appropriate sequence, such as an SV40 transcription termination signal sequence, an HSV TK (herpes simplex virus thymidine kinase) transcription termination signal sequence, or the like, may be selected therefrom and used.

The adapter-expressing cassette is inserted into the HSV genome for expression thereof without inhibiting the propagation of HSV, and such insertion may be carried out without deletion of the HSV genome, or insertion into loci from which some or all non-essential genes in the HSV genome are deleted may be conducted. When the adapter-expressing cassette is inserted without deletion of the HSV genome, it may be inserted between genes. Preferred examples of the insertion locus include the locus between UL3 and UL4 genes, the locus between UL26 and UL27 genes, the locus between UL37 and UL38 genes, the locus between UL48 and UL49 genes, the locus between UL53 and UL54 genes, the locus between US1 and US2 genes, etc.

When the adapter-expressing cassette is inserted into loci from which some or all non-essential genes in the HSV genome are deleted, the deleted non-essential genes may be any non-essential genes, as exemplified above.

In order to express the adapter in multiple ways, at least one adapter-expressing cassette having a polycistronic configuration may be inserted into the HSV genome, or at least two adapter-expressing cassettes having a monocistronic configuration may be inserted into the HSV genome.

The adapter-expressing cassette having a polycistronic configuration includes at least two adapter genes therebetween, in addition to the promoter and the transcription termination signal sequence, and between these genes, a nucleic acid sequence encoding an IRES (internal ribosome entry site) or a 2A peptide is located so as to be capable of expressing each protein. Here, the 2A peptide is identified from picornavirus and insect virus type C rotavirus, and preferred examples of the 2A peptide include 2A of Thosea asigna virus (T2A), 2A of porcine teschovirus-1 (P2A), 2A of ERAV (equine rhinitis A virus) (E2A), 2A of FMDV (foot-and-mouth disease virus) (F2A), and the like. For specific information on the IRES or 2A peptide, reference may be made to Edith Renaud-Gabardos et al. [Internal ribosome entry site-based vectors for combined gene therapy, World J. Exp. Med. 2015 Feb. 20; 5 (1): 11-20], Szymczak et al. [Development of 2A peptide-based strategies in the design of polycistronic vectors, (2005) Expert Opin. Biol. Ther. 5:627-638], Kim et al. [High Cleavage Efficiency of a 2A Peptide Derived from Porcine Teschovirus-1 in Human Cell Lines, Zebrafish and Mice, (2011) PLOS One 6 (4): e18556], and the like.

In order to express the adapter in multiple ways, when the adapter-expressing cassette has a monocistronic configuration, at least two adapter-expressing cassettes are inserted into the HSV genome. Here, at least two adapter-expressing cassettes may be continuously inserted at the same locus in the HSV genome, or may be inserted at different respective loci. For example, an adapter-expressing cassette for a target molecule HER2 and an adapter-expressing cassette for a target molecule EpCAM may be inserted at the same locus between UL3 and UL4 genes, or alternatively, an adapter for a target molecule HER2 may be inserted between UL3 and UL4 genes and an adapter for a target molecule EpCAM may be inserted between UL26 and UL27 genes, as different loci. When at least two adapter-expressing cassettes are inserted continuously at the same locus, a non-coding region may be interposed between the expression cassettes. The non-coding region is intended to prevent at least two expression cassettes from interfering with expression (transcription and/or translation), and the non-coding region may comprise 3-60 nucleotides.

In the present disclosure, when it is necessary to express three or more types of adapters in multiple ways, an adapter-expressing cassette having a polycistronic configuration capable of expressing two types of adapters and an adapter-expressing cassette having a monocistronic configuration capable of expressing the remaining adapter may be inserted together at the same locus or different loci in the HSV genome.

In the recombinant HSV of the present disclosure, the cancer-cell-targeting domain of the adapter is a site that specifically recognizes and binds to the target molecule of cancer cells, which are target cells, and the target molecule recognized by the cancer-cell-targeting domain is any antigen or any receptor present on the surface of cancer cells.

The antigen or receptor is preferably an antigen or a receptor that is expressed only in cancer cells or is overexpressed in cancer cells compared to normal cells. Examples of the antigen or receptor may include target molecules, such as EGFRvIII (epidermal growth factor receptor variant III) expressed in glioblastoma, EGFR (epidermal growth factor receptor) overexpressed in anaplastic thyroid cancer, breast cancer, lung cancer, glioma and the like, a metastin receptor overexpressed in papillary thyroid cancer and the like, an ErbB-based receptor tyrosine kinase overexpressed in breast cancer and the like, HER2 (human epidermal growth factor receptor 2) overexpressed in breast cancer, bladder cancer, gallbladder cancer, cholangiocarcinoma, esophagogastric junction cancer and the like, a tyrosine kinase-18-receptor (c-Kit) overexpressed in sarcomatoid renal carcinoma and the like, an HGF receptor c-Met overexpressed in esophageal adenocarcinoma and the like, CXCR4 or CCR7 overexpressed in breast cancer and the like, an endothelin-A receptor overexpressed in prostate cancer, PPAR-δ (peroxisome proliferator activated receptor δ) overexpressed in rectal cancer and the like, PDGFR-α (platelet-derived growth factor receptor α) overexpressed in ovarian cancer and the like, CD133 overexpressed in liver cancer, multiple myeloma and the like, CEA (carcinoembryonic antigen) overexpressed in lung cancer, colorectal cancer, stomach cancer, pancreatic cancer, breast cancer, rectal cancer, colon cancer, medullary thyroid cancer and the like, EpCAM (epithelial cell adhesion molecule) overexpressed in liver cancer, stomach cancer, colorectal cancer, pancreatic cancer, breast cancer and the like, MSLN (mesothelin) overexpressed in lung cancer, breast cancer, pancreatic cancer, ovarian cancer and the like, GD2 (disialoganglioside) overexpressed in neuroblastoma and the like, GPC3 (glypican 3) overexpressed in hepatocellular carcinoma and the like, PSMA (prostate-specific membrane antigen) overexpressed in prostate cancer and the like, TAG-72 (tumor-associated glycoprotein 72) overexpressed in ovarian cancer, breast cancer, colon cancer, lung cancer, pancreatic cancer and the like, GD3 (disialoganglioside) overexpressed in melanoma and the like, HLA-DR (human leukocyte antigen-DR) overexpressed in blood cancer, solid cancer and the like, MUC1 (Mucin 1) overexpressed in advanced solid cancer and the like, NY-ESO-1 (New York esophageal squamous cell carcinoma 1) overexpressed in advanced non-small-cell lung cancer and the like, LMP1 (latent membrane protein 1) overexpressed in nasopharyngeal neoplasms and the like, TRAILR2 (tumor-necrosis factor-related apoptosis-inducing ligand receptor) overexpressed in lung cancer, non-Hodgkin's lymphoma, ovarian cancer, colon cancer, colorectal cancer, pancreatic cancer and the like, VEGFR2 (vascular endothelial growth factor receptor 2) as an angiogenesis factor receptor, and HGFR (hepatocyte growth factor receptor) overexpressed in hepatocellular carcinoma and the like. Moreover, the surface antigen of cancer stem cells, such as CD44, CD166 or the like, may be a target molecule. Many target molecules overexpressed in cancer cells compared to normal cells are known in the art, and for other target molecules in addition to the examples listed above, reference may be made to Anne T. Collins et al. [Prospective Identification of Tumorigenic Prostate Cancer Stem Cells. Cancer Res. 2005 Dec. 1; 65 (23): 10946-51], Chenwei Li et al. [Identification of Pancreatic Cancer Stem Cells. Cancer Res. 2007 Feb. 1; 67 (3): 1030-7], Shuo Ma et al. [Current Progress in CAR-T Cell Therapy for Solid Tumors. Int. J. Biol. Sci. 2019 Sep. 7; 15 (12): 2548-2560], Dhaval S. Sanchala et al. [Oncolytic Herpes Simplex Viral Therapy: A Stride Toward Selective Targeting of Cancer Cells. Front Pharmacol. 2017 May 16; 8:270], and the like.

In particular, the target molecule is preferably HER2 or EpCAM in the present disclosure.

The target cell targeted by the adapter of the recombinant HSV of the present disclosure is any cancer cell having a target molecule capable of being targeted by the cancer-cell-targeting domain of the adapter of the present disclosure. The cancer cell may be any type of carcinoma, such as esophageal cancer, stomach cancer, colorectal cancer, rectal cancer, oral cancer, pharyngeal cancer, laryngeal cancer, lung cancer, colon cancer, breast cancer, uterine cervical cancer, endometrial cancer, ovarian cancer, prostate cancer, testicular cancer, melanoma, bladder cancer, kidney cancer, liver cancer, pancreatic cancer, bone cancer, connective tissue cancer, skin cancer, brain cancer, thyroid cancer, leukemia, Hodgkin's disease, lymphoma, multiple myeloma, blood cancer, and the like.

In the present disclosure, the cell-targeting domain of the adapter may be an antibody derivative or an antibody analogue, in addition to a complete antibody having the ability to specifically bind to the target molecule. The antibody derivative is a fragment of a complete antibody that includes at least one antibody variable region having the ability to specifically bind to the target molecule, or is a modified antibody. Examples of the antibody derivative may include antibody fragments such as Fab, scFv, Fv, VhH, VH, VL, etc., multivalent or multispecific modified antibodies such as Fab2, Fab3, minibodies, diabodies, tribodies, tetrabodies, bis-scFv, etc., and the like. The antibody analogue is an artificial peptide or polypeptide that has the ability to specifically bind to the target molecule, like the antibody, but is different in structure from the antibody, and generally has a lower molecular weight than the antibody. Examples of the antibody analogue may include ABD, Adhiron, affibodies, affilins, affimers, alphabodies, anticalin, armadillo repeat protein, centyrins, DARPins, fynomers, a Kunitz region, ProNectin, repebodies, and the like.

A considerably large number of documents in the art regarding the antibody, antibody derivative, antibody analogue, and production thereof have been published, and examples thereof include Renate Kunert & David Reinhart [Advances in recombinant antibody manufacturing. Appl. Microbiol. Biotechnol. 2016 April; 100 (8): 3451-61], Holliger P. and Hudson P. J. [Engineered antibody fragments and the rise of single domains, Nat. Biotechnol. 2005 September; 23 (9): 1126-36], Xiaowen Yu et al. [Beyond Antibodies as Binding Partners: The Role of Antibody Mimetics in Bioanalysis, Annual Review of Analytical Chemistry, 2017, 10:293-320], Abdul Rasheed Baloch et al. [Antibody mimetics: promising complementary agents to animal-sourced antibodies, Critical Reviews in Biotechnology, 2016, 36:268-275], and the like.

In the present disclosure, the cell-targeting domain of the adapter is preferably an scFv (single-chain variable fragment). The scFv is a single-chain antibody in which the heavy-chain variable region (VH) and the light-chain variable region (VL) of an immunoglobulin are linked via a short linker peptide. In the scFv, the C-terminus of VH is linked to the N-terminus of VL, or the C-terminus of VL is linked to the N-terminus of VH. In the scFv, the linker peptide may be a linker peptide having any length and any sequence, so long as it does not interfere with the inherent three-dimensional structures of heavy and light chains and enables the heavy and light chains to be spatially adjacent to each other to thus have the ability to specifically bind to the target molecule. Taking into consideration flexibility, solubility, resistance to proteolysis, etc., the linker preferably comprises at least one selected from among amino acids such as Ser, Gly, Ala, Thr, etc., and the length thereof may be 1-30 amino acids, preferably 3-25 amino acids, and more preferably 8-20 amino acids.

In the present disclosure, the target molecule targeted by scFv is HER2 or EpCAM. Specifically, scFv for HER2 is preferably configured such that VH of SEQ ID NO: 4 and VL of SEQ ID NO: 5 are linked in the order of VH, linker peptide and VL via a linker peptide (i.e. the C-terminus of VH is linked to the N-terminus of VL via the linker peptide), and scFv for EpCAM is preferably configured such that VL of SEQ ID NO: 6 and VH of SEQ ID NO: 7 are linked in the order of VL, linker peptide and VH via a linker peptide (i.e. the C-terminus of VL is linked to the N-terminus of VH via the linker peptide).

In the present disclosure, the extracellular domain of HVEM may be HveA87 of SEQ ID NO: 10 (the HveA87 sequence comprising the leader sequence is represented in SEQ ID NO: 11), HveA102 of SEQ ID NO: 12 (the HveA102 sequence comprising the leader sequence is represented in SEQ ID NO: 13), or HveA107 of SEQ ID NO: 14 (the HveA107 sequence comprising the leader sequence is represented in SEQ ID NO: 15), which is disclosed in Korean Patent No. 10-0937774 and U.S. Pat. No. 8,318,662 (these documents are considered part of the present specification), in addition to HveA82 of SEQ ID NO: 8 (the HveA82 sequence comprising the leader sequence is represented in SEQ ID NO: 9), used in the following examples. The leader sequence contained in the sequences of SEQ ID NOs: 9, 11, 13 and 15 is the signal peptide sequence of HveA. HveA87, HveA102, and HveA107 further comprise 5, 20, and 25 more amino acids than HveA82, respectively, and all of these may be used as HSV receptors of adapters, as confirmed in Korean Patent and U.S. Patent described above.

In the present disclosure, the linker sequence may be interposed between the cancer-cell-targeting domain and the extracellular domain of HVEM, and this linker sequence may be a linker having any length and any sequence, so long as it does not inhibit the function of each domain of the adapter. Preferably, the linker comprises at least one amino acid among the four amino acids Ser, Gly, Ala and Thr, and the length thereof may be 1-30 amino acids, preferably 3-25 amino acids, and more preferably 8-20 amino acids.

Also, the adapter of the present disclosure may be configured in the order of NH₂/cancer-cell-targeting domain/extracellular domain of HVEM/COOH or in the reverse order thereof. When the linker peptide is interposed therebetween, the adapter may be configured in the order of NH₂/cancer-cell-targeting domain/linker peptide/extracellular domain of HVEM/COOH or in the reverse order thereof.

The adapter of the present disclosure may be configured such that the leader sequence (i.e. secretion-inducing signal sequence) may be further attached to the N-terminus thereof, particularly the N-terminus of the cancer-cell-targeting domain (the N-terminus of VH or VL when scFv is used) in the adapter configuration in the order of NH₂/cancer-cell-targeting domain/linker peptide/extracellular domain of HVEM/COOH, or to the N-terminus of the extracellular domain of HVEM in the adapter configuration in the order of NH₂/extracellular domain of HVEM/linker peptide/cancer-cell-targeting domain/COOH. The leader sequence is a sequence having a function of inducing a protein expressed in the cytoplasm to be secreted to the outside of the cells through the cell membrane, and typically comprises about 15 to 30 consecutive hydrophobic amino acid residues. The leader sequence that may be used is not particularly limited, but may be any sequence present at the N-terminus of the protein secreted to the outside of the cell membrane, such as the leader sequence of HveA, the leader sequence of the antibody variable region VL (kaapa), the leader sequence of the tissue plasminogen activator (t-PA), the leader sequence of serum albumin, the leader sequence of lactoferrin, the leader sequence of α-casein, the leader sequence of various hormones including human growth hormone, the leader sequence of polypeptide secreted from yeast or bacteria, etc.

The leader sequence is a sequence that acts to induce the expression of the adapter in the target cells and the release of the adapter to the outside of the cells, and may be omitted, because the adapter acts to induce infection of the adjacent target cells with HSV only after the target cells are lysed and HSV is released.

In the present disclosure, in order to facilitate cloning, an amino acid corresponding to an arbitrary restriction enzyme site may be interposed between VH and VL when scFv for the target molecule is used as the cell-targeting domain, between VH or VL and the linker peptide when the linker peptide is disposed between VH and VL, between scFv and HVEM, between scFv and the linker when the linker peptide is disposed between scFv and HVEM, or between the linker and HVEM. For example, EF (base sequence: GAATTC), on which the restriction enzyme EcoRI acts, GS (base sequence: GGATCC), on which BamHI acts, or LEEL (SEQ ID NO: 47) (base sequence: CTCGAGGAGCTC (SEQ ID NO: 48)), on which XhoI acts, may be interposed therebetween.

In the present disclosure, in order to express factors alone or in any combination for inducing or enhancing an immune response to cancer cells, the recombinant HSV may be configured such that a gene for the corresponding factor is inserted into the HSV genome. Such factors may be manipulated so as to express cytokines, chemokines, immune checkpoint antagonists (e.g. antibodies, antibody derivatives or antibody analogues, especially scFv), co-stimulatory factors capable of inducing activation of immune cells (T cells or NK cells), antagonists capable of inhibiting the function of TGFβ, which suppresses the immune response to cancer cells (e.g. antibodies, antibody derivatives or antibody analogues, especially scFv), heparanase capable of degrading heparan sulfate proteoglycan for a solid tumor microenvironment, antagonists capable of inhibiting the function of angiogenesis factor receptor VEGFR-2 (VEGF receptor-2) (e.g. antibodies, antibody derivatives or antibody analogues, especially scFv), and the like.

As cytokines, for example, interleukins such as IL-2, IL-4, IL-7, IL-10, IL-12, IL-15, IL-18, IL-24, etc., interferons such as IFNα, IFNβ, IFNγ, etc., tumor necrosis factors such as TNFα, etc., and colony-stimulating factors such as GM-CSF, G-CSF, FLT3L, etc. may be used alone or in any combination of two or more thereof so as to be expressed in the recombinant HSV.

As chemokines, for example, CCL2 (C—C motif chemokine ligand 2), CCL5 (RANTES), CCL7, CCL9, CCL10, CCL12, CCL15, CCL19, CCL21, CCL20, and XCL-1 (X—C motif chemokine ligand 1) may be used alone or in combination so as to be expressed in the recombinant HSV.

As immune checkpoint antibodies, antagonists to PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIR (killer-cell immunoglobulin-like receptor), LAG3 (lymphocyte activation gene 3), GITR (glucocorticoid-induced TNFR-related protein), GITRL (glucocorticoid-induced TNFR-related protein ligand), and CTLA-4 (cytolytic T lymphocyte associated antigen-4) may be used alone or in combination so as to be expressed in the recombinant HSV.

As co-stimulatory factors, CD2, CD7, LIGHT, NKG2C, CD27, CD28, 4-1BB, OX40, CD30, CD40, LFA-1 (lymphocyte function-associated antigen-1), ICOS (inducible T cell co-stimulator), CD3γ, CD30, and CD38 may be used alone or in combination so as to be expressed in the recombinant HSV.

In the present disclosure, the recombinant HSV may be manipulated so as to express a prodrug-activating enzyme that converts a prodrug into a drug that exhibits toxicity to cancer cells. Examples of the prodrug-activating enzyme may include cytosine deaminase, which converts 5-FC (5-fluorocytosine) as a prodrug into 5-FU (5-fluorouracil) as a drug, rat cytochrome P450 (CYP2B1), which converts CPA (cyclophosphamide) as a prodrug into PM (phosphoramide mustard) as a drug, carboxylesterase, which converts irinotecan (SN-38150) as a prodrug into SN-38 as a drug, bacterial nitroreductase, which converts BC1954 as a prodrug into 4-hydroxylamine151 as a DNA cross-linker, PNP (purine nucleoside phosphorylase) isolated from *E. coli*, which converts 6-methylpurine-2'-deoxyriboside as a prodrug into 6-methylpurine as a drug, and the like.

Moreover, in the present disclosure, the recombinant HSV may be manipulated so as to express TRAIL (TNF-related apoptosis-inducing ligand). TRAIL is known to induce the death of cancer cells by binding to the receptor thereof, which is overexpressed in cancer cells (Kaoru Tamura et al. Multimechanistic Tumor Targeted Oncolytic Virus Overcomes Resistance in Brain Tumors. Mol. Ther. 2013 January; 21 (1): 68-77).

For more details regarding the use of factors or prodrug-activating enzymes to induce or enhance these immune responses, reference may be made to Michele Ardolino et al. [Cytokine treatment in cancer immunotherapy, J. Oncotarget, Oncotarget. 2015 Aug. 14; 6 (23): ], Bernhard Homey et al. [Chemokines: Agents for the Immunotherapy of Cancer. Nat Rev Immunol. 2002 March; 2 (3): 175-84], Marianela Candolfi et al. [Evaluation of proapoptotic transgenes to use in combination with Flt3L in an immune-stimulatory gene therapy approach for Glioblastoma multiforme (GBM), J. FASEB J., 2008, 22:107713], Danny N Khalil et al. [The Future of Cancer Treatment: Immunomodulation, CARs and Combination Immunotherapy. Nat Rev Clin Oncol. 2016 May; 13 (5): 273-90], Paul E Hughes et al. [Targeted Therapy and Checkpoint Immunotherapy Combinations for the Treatment of Cancer. Trends Immunol. 2016 July; 37 (7): 462-476], Cole Peters and Samuel D. Rabkin [Designing herpes viruses as oncolytics, Mol. Ther. Oncolytics. 2015; 2:15010], and the like.

In the present disclosure, as in the aforementioned adapter, the factors or prodrug-activating enzymes to induce or enhance immune responses are configured such that the expression cassette of the gene thereof (i.e. a construct in which the gene thereof is operably linked with a promoter sequence that enables expression thereof and a polyadenylation signal sequence) is inserted into the HSV genome without inhibiting the propagation of HSV. Such insertion may be performed without deletion of the HSV genome, or insertion into loci from which some or all non-essential genes in the HSV genome are deleted may be conducted. Here, upon insertion without deletion of the HSV genome, insertion may be performed between genes, and preferred insertion loci are, for example, between UL3 and UL4, between UL26 and UL27, between UL37 and UL38, between UL48 and UL49, between UL53 and UL54, and between US1 and US2. Upon insertion into loci from which non-essential genes are deleted or into genes without deletion of non-essential genes, such non-essential genes may be selected from among any non-essential genes, as described above.

Another aspect of the present disclosure pertains to a pharmaceutical composition for treating cancer containing the recombinant HSV described above as an active ingredient.

The pharmaceutical composition of the present disclosure has anticancer effects against a carcinoma expressing a target molecule targeted by the targeting domain of the adapter expressed by the recombinant HSV. Examples of the carcinoma are as described above in relation to the target molecule.

In particular, it is preferable that the composition of the present disclosure have anticancer effects against carcinoma having tumor cells expressing HER2 or EpCAM. Examples of tumor cells expressing HER2 include breast cancer cells, ovarian cancer cells, stomach cancer cells, lung cancer cells, head and neck cancer cells, osteosarcoma cells, glioblastoma multiforme cells, salivary gland tumor cells, and the like. Also, examples of tumor cells expressing EpCAM include liver cancer cells, prostate cancer cells, breast cancer cells, colorectal cancer cells, lung cancer cells, gallbladder cancer cells, pancreatic cancer cells, stomach cancer cells, and the like.

In the present disclosure, anticancer effects include death of cancer cells, decreased viability of cancer cells, inhibition or delay of pathological symptoms of cancer due to suppression of cancer-cell propagation, inhibition or delay of onset of such pathological symptoms, inhibition of cancer metastasis, and inhibition of cancer recurrence.

The pharmaceutical composition of the present disclosure may further include a recombinant adapter molecule in addition to the recombinant HSV as the active ingredient. The recombinant adapter molecule is one in which a fused protein having a cancer-cell-targeting domain, as in the adapter expressed by the recombinant HSV, or more precisely, as in the fused protein of the cancer-cell-targeting domain and the extracellular domain of HVEM, is produced through a recombination process. Here, having the cancer-cell-targeting domain as in the adapter expressed by the recombinant HSV means that when the target molecule targeted by the cancer-cell-targeting domain of the adapter expressed by HSV is HER2, the target molecule targeted by the cancer-cell-targeting domain of the adapter molecule is also HER2. The method of producing the target protein of interest using a recombination process typically includes preparing an expression vector able to express a target protein and transforming the expression vector into host cells such as *E. coli*, yeast or animal cells (CHO cells, NSO cells, BHK cells, Sp2 cells, or HEK-293 cells), followed by culture and then isolation of the target protein, and the method of producing the target protein of interest using a recombination process is well known in the art (Sambrook et al., Molecular Cloning: A Laboratory Manual, Cold Spring Harbor Laboratory Press, (2001)). In particular, with regard to the production of the recombinant adapter molecule used in the present disclosure, reference may be made to Korean Patent No. 10-0937774 and U.S. Pat. No. 8,318,662. The pharmaceutical composition of the present disclosure further includes such a recombinant adapter molecule, and thus, when the recombinant HSV, which is the active ingredient of the present disclosure, and the recombinant adapter molecule are administered together to a patient, the initial cancer-cell infection efficiency of the recombinant HSV is effectively increased.

Moreover, the pharmaceutical composition of the present disclosure may be used in combination with or in a mixture with an approved anticancer agent. Examples of the anticancer agent may include any anticancer agents, any cytokine drugs, any antibody drugs, any immune checkpoint inhibitor drugs, and any cell therapeutic agents (for car-T cell therapy or car-NK cell therapy) that exhibit cytotoxicity to cancer cells, such as metabolic antagonists, alkylating agents, topoisomerase antagonists, microtubule antagonists, and plant-derived alkaloids. Specific examples thereof may include taxol, nitrogen mustard, imatinib, oxaliplatin, gefitinib, bortezomib, sunitinib, carboplatin, cisplatin, rituximab, erlotinib, sorafenib, IL-2 drug, IFN-α drug, IFN-γ drug, trastuzumab, blinatumomab, ipilimumab, pembrolizumab, nivolumab, atezolizumab, durvalumab, bevacizumab, cetuximab, tisagenlecleucel (Kymriah), axicabtagene ciloleucel (Yescarta), and the like. In addition to the exemplary anticancer agents, other anticancer agents known in the art may be used without limitation in combination with or in a mixture with the pharmaceutical composition of the present disclosure.

The pharmaceutical composition of the present disclosure may include a pharmaceutically acceptable carrier or excipient, and may thus be prepared in the form of an oral formulation or a parenteral formulation through a typical method known in the art depending on the route of administration.

Such a pharmaceutically acceptable carrier or excipient does not impair the activity or properties of the drug and is not itself toxic to the human body, and examples thereof may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water (e.g. saline and sterile water), syrup, methyl cellulose, methylhydroxybenzoate, propylhydroxybenzoate, talc, magnesium stearate, mineral oil, Ringer's solution, buffer, maltodextrin solution, glycerol, ethanol, dextran, albumin, and any combination thereof. In particular, when the pharmaceutical composition of the present disclosure is formulated in the form of a liquid solution, an appropriate carrier or excipient may include saline, sterile water, Ringer's solution, buffered saline, albumin injection solution, dextrose solution, maltodextrin solution, glycerol, and ethanol, which may be used alone or in combination. If necessary, other typical pharmaceutical additives, such as antioxidants, buffers, bacteriostatic agents, etc., may be added and used.

When the pharmaceutical composition of the present disclosure is prepared into an oral formulation, it may be manufactured in the form of a tablet, troche, capsule, elixir, suspension, syrup, wafer, etc., and when prepared into a parenteral formulation, especially an injection, it may be manufactured in a unit dose ampoule or a multi-dose form. The pharmaceutical composition of the present disclosure may also be manufactured in the form of a solution, suspension, tablet, pill, capsule, sustained-release formulation, and the like.

The pharmaceutical composition of the present disclosure may be formulated in a unit dosage form suitable for administration to a patient's body according to a typical method in the pharmaceutical field, and may be administered through an oral route of administration or a parenteral route of administration, such as dermal, intralesional, intravenous, intramuscular, intraarterial, intramedullary, intrathecal, intraventricular, pulmonary, transdermal, subcutaneous, intraperitoneal, intranasal, enteral, topical, sublingual, intravaginal, and rectal routes, using any administration method commonly used in the art.

The dose (effective amount) of the pharmaceutical composition of the present disclosure may vary depending on factors such as the formulation method, the administration mode, the patient's age, weight and gender, pathological conditions, diet, administration time, administration route, excretion rate, and response sensitivity, and may be appropriately determined by those skilled in the art in consideration of these factors. In a preferred embodiment, the pharmaceutical composition of the present disclosure is prepared as an injection in a unit dosage form. When prepared as an injection in a unit dosage form, the amount of the recombinant HSV included per unit dose of the pharmaceutical composition of the present disclosure may range from $10^2$-$10^{14}$ pfu, particularly $10^4$-$10^{11}$ pfu.

Still another aspect of the present disclosure pertains to a method of treating or preventing cancer (tumors), including administering the pharmaceutical composition containing the recombinant HSV as described above to a subject such as a patient in an effective amount.

The method of treating cancer is made possible by lysing and killing cancer cells having a target molecule targeted by the cancer-cell-targeting domain of the adapter of the recombinant HSV. Therefore, the treatment method of the present disclosure may be applied to any carcinoma having such a target molecule. In particular, the treatment method of the present disclosure is preferably applied to a carcinoma expressing HER2 or EpCAM.

The treatment method of the present disclosure may be used without limitation in combination with the other cancer treatment methods described above. For example, cytotoxic anticancer agents, cytokine drugs, antibody drugs, immune checkpoint inhibitor drugs, cell therapeutic agents (for car-T cell therapy or car-NK cell therapy), radiotherapy, surgery, etc., as exemplified above, may be used before or after administration of the pharmaceutical composition of the present disclosure or in a manner of simultaneous administration in combination with the pharmaceutical composition of the present disclosure.

In the treatment method of the present disclosure, the effective amount is an amount in which the pharmaceutical composition of the present disclosure is administered so as to exhibit the intended medical effect, such as a cancer treatment or prevention effect, when the pharmaceutical composition of the present disclosure is administered to a subject such as a patient for the administration period based on the recommendation of a medical expert, etc. As described above, such an effective amount may be appropriately determined by a person skilled in the art, such as a medical expert, etc., depending on the patient's age, weight and gender, pathological conditions, and the like, as described above.

In the treatment method of the present disclosure, the pharmaceutical composition is preferably administered in the form of an injection to a patient or the like in a mode of parenteral administration, for example, intralesional (intratumoral), intravenous, intramuscular or intraarterial administration or the like.

Advantageous Effects

According to the present disclosure, it is possible to provide a recombinant HSV capable of multiple targeting through multiple expression of an adapter that is a fused protein of a cancer-cell-targeting domain and an extracellular domain of HVEM, and also to provide a recombinant HSV capable of multiple targeting by having a modified glycoprotein so as to enable retargeting, in addition to being capable of expressing the adapter that is the fused protein of the cancer-cell-targeting domain and the extracellular domain of HVEM.

In addition, according to the present disclosure, it is possible to provide a pharmaceutical composition for cancer treatment or prevention containing the recombinant HSV capable of multiple targeting as an active ingredient, and a method of preventing or treating cancer including administering the pharmaceutical composition to a subject such as a patient in an effective amount.

The recombinant HSV capable of multiple targeting according to the present disclosure has high cancer-cell infection efficiency and high cancer-cell-killing function compared to single-targeting HSV.

BRIEF DESCRIPTION OF DRAWINGS

FIG. 7 schematically shows the genomic structure of each of (i) a single-targeting virus having a HER2-targeting modified glycoprotein gH and (ii) a HER2 dual-targeting HSV-1 virus having a HER2-targeting modified glycoprotein gH and expressing a HER2-targeting adapter;

FIG. 8 shows the entire amino acid sequence of the HER2scFv ligand inserted and fused into gH and the configuration of the corresponding sequence;

FIG. 9 schematically shows the genomic structure of each of (i) a single-targeting virus having an EpCAM-targeting modified glycoprotein gH and (ii) an EpCAM dual-targeting HSV-1 virus having an EpCAM-targeting modified glycoprotein gH and expressing an EpCAM-targeting adapter;

DETAILED DESCRIPTION

A better understanding of the present disclosure will be given through the following examples. However, these examples are not to be construed as limiting the scope of the present disclosure.

<Example 1> Production of HVEM-Restricted
HSV-1 Virus

Figure 1:
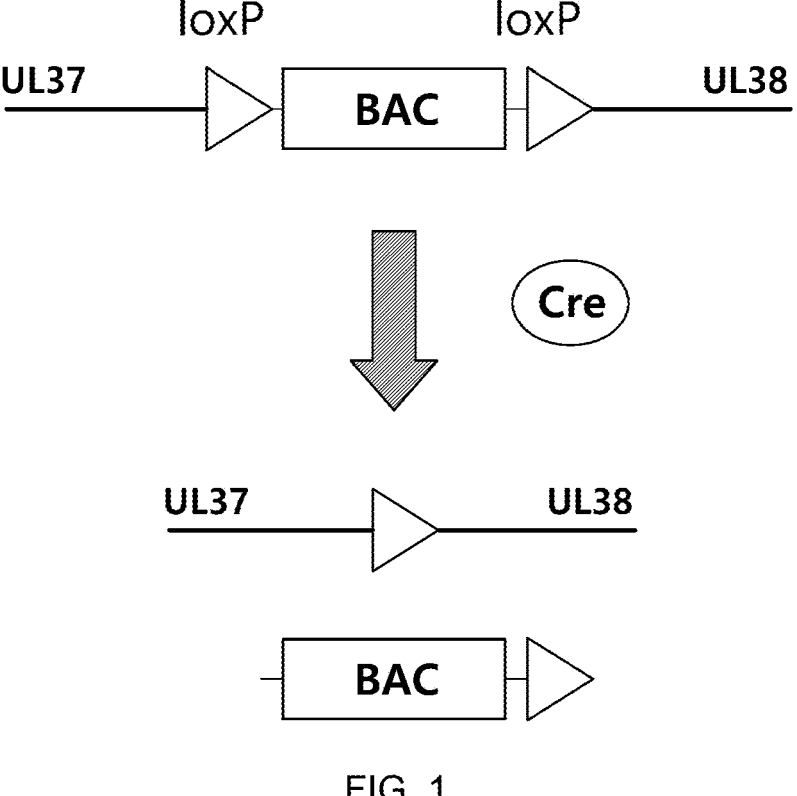
FIG. 1 schematically shows the genomic structure of KOS-37 BAC.

An HSV-1 gene is composed of a large gene about 152 kb in size, and thus KOS-37/BAC (GenBank Accession No. MF156583) (Gierasch W. W. et al. J. Virol. Methods. 2006. 135:197-206) was used to insert a foreign gene or a mutation at a specific locus. The HSV-1 KOS strain is a kind of HSV-1 strain mainly used in laboratories because of the well-known characteristics thereof and the usefulness thereof for investigation of gene function and etiology (Smith K O. Proc. Soc. Exp. Biol. Med. 1964. 115:814-816). KOS-37/BAC, manufactured by inserting a BAC plasmid into a KOS genome, enables cloning at the bacterial level through transformation of DH10B bacteria (Invitrogen) (Gierasch W. W. et al.; J. Virol. Methods. 2006. 135:197-206). In the KOS-37/BAC, BAC (bacterial artificial chromosome) is inserted along with a LoxP site at both sides thereof into a locus between UL37 and UL38 of the HSV-1 KOS genome. This is intended to remove the BAC gene using a Cre-Lox system in subsequent procedures. The schematic view thereof is shown in FIG. 1.

In order to manufacture HVEM-restricted HSV-1, which enters cells only through the HVEM cell receptor, a gD-R222N/F223I HSV-1 virus, in which arginine (R) at position 222 and phenylalanine (F) at position 223 of the HSV-1 gD amino acid sequence (GenBank Accession No. ASM47818, SEQ ID NO: 16) were substituted with asparagine (N) and isoleucine (I), respectively, was manufactured.

The gD-R222N/F223I HSV-1 virus manufactured through mutation is able to infect host cells only through HVEM (HveA) rather than nectin-1 as the cell entry receptor (Uchida H et al., J. Virol. 2009. 83 (7): 2951-2961), and is thus advantageous from the aspect of safety because it cannot infect normal cells having the nectin-1 receptor.

Figure 2:
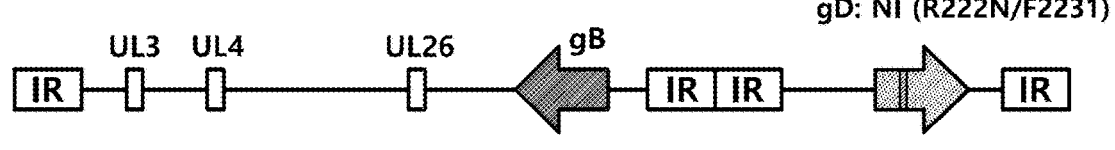
FIG. 2 schematically shows the genomic structure of an HVEM-restricted HSV-1 virus.

The genomic structure of the HVEM-restricted KOS-gD-R222N/F223I virus is schematically shown in FIG. 2.

The KOS-gD-R222N/F223I HSV-1 virus was manufactured by introducing R222N/F223I mutations into the gD site of KOS-37/BAC according to the manufacturer's protocol using a counter-selection BAC modification kit (GeneBridges Inc.).

Specifically, an *E. coli* clone containing KOS-37/BAC was transformed with a pRed/ET plasmid expressing RecE and RecT capable of performing the function of homologous recombination (Muyrers J. P. et al.; Nucleic Acids Res. 1999. 27 (6): 1555-1557). A gD-rpsL-neo/kan cassette was manufactured using a set of homologous region primers (forward primer gD-rpsL For: SEQ ID NO: 17, reverse primer gD-rpsL Rev: SEQ ID NO: 18) including a locus at which to introduce a mutation into gD. The gD-rpsL-neo/kan cassette is composed of the gD homologous region at the insertion locus, the rpsL gene, which is a selective marker for conferring sensitivity to streptomycin, and the neo/kan gene, which confers kanamycin resistance. When the gD-rpsL-neo/kan cassette is inserted, *E. coli* having sensitivity to streptomycin antibiotics due to the rpsL gene and kanamycin resistance due to the neo/kan gene is manufactured. After inducing the expression of RecE and RecT so as to enable homologous recombination by activating the function of pRed/ET by adding L-arabinose (Sigma-Aldrich) to the *E. coli* clone containing KOS-37/BAC and pRed/ET (Muyrers J. P. et al.; Nucleic Acids Res. 1999. 27 (6): 1555-1557), transformation with 200 ng of the manufactured gD-rpsL-neo/kan cassette was performed. Through homologous recombination, the gD-rpsL-neo/kan cassette is inserted into the gD locus of KOS-37/BAC. *E. coli* in which gD-rpsL-neo/kan is inserted into KOS-37/BAC exhibits kanamycin resistance, but streptomycin resistance is blocked by the rpsL gene. It was inferred for *E. coli* obtained from the kanamycin medium that gD-rpsL-neo/kan was inserted therein, and the final step of inserting a gene was performed. After inducing the expression of RecE and RecT so as to enable homologous recombination by activating the function of pRed/ET by adding L-arabinose (Sigma-Aldrich) to *E. coli* containing the KOS 37-BAC gD-rpsL-neo/kan clone, transformation with 100 pmol of R222N_F223I_mutant (SEQ ID NO: 19), which is an oligonucleotide in which R and F at respective positions 222 and 223 of gD were substituted with N and I, was performed. Based on the principle whereby streptomycin resistance blocked by rpsL is activated upon replacing the existing gD-rpsL-neo/kan cassette with the inserted oligonucleotide, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352), and the substitution of N and I at respective positions 222 and 223 of gD was confirmed through PCR (polymerase chain reaction) and DNA sequencing.

Next, for viral production, the completed KOS-37/BAC-gD-R222N/F223I DNA was extracted using a large-construct DNA purification kit (Macherey-Nagel), after which $2 \times 10^5$ Cre-Vero-HVEM cells were transfected with 1 µg of DNA using a Lipofectamine 2000 reagent (Invitrogen). Then, cell culture was carried out using DMEM (Dulbecco's Modified Eagle's Medium) (Welgene) containing 100 U/ml penicillin/100 µg/ml streptomycin (Welgene) and 10% FBS (fetal bovine serum, Welgene). The Cre-Vero-HVEM cell line is a cell line inducing HVEM protein expression by inserting the HVEM gene into the Cre-Vero cell line (Gierasch et al.; J. Virol. Methods. 2006. 135:197-206). The reason for using Cre-Vero-HVEM is that the BAC gene of KOS-37/BAC-gD-R222N/F223I may be removed using Cre recombinase of the cells and also that infection with the KOS-gD-R222N/F223I virus due to HVEM overexpression is effective, and thus mass production of viruses becomes easy. 3-4 days after gene introduction, the formation of cell plaques was confirmed, after which the virus-containing cells were collected, subjected three times to a freeze-thaw process (Gierasch W. W. et al.; J. Virol. Methods. 2006. 135:197-206), and sonicated, ultimately obtaining a KOS-gD-R222N/F223I virus.

<Example 2> Production of HVEM-Restricted HSV-1 Virus Expressing EmGFP

For the production of HVEM-restricted HSV-1 expressing EmGFP, an expression cassette capable of expressing EmGFP (emerald green fluorescent protein) was inserted into the UL26/UL27 locus of the KOS-37/BAC-gD-R222N/F223I DNA manufactured in Example 1 (Tiffany A. et al., J. Virol Methods. 2015. 231:18-25). This is to facilitate the observation of viral production and infection using EmGFP as a marker. A pCDNA6.2-GW/EmGFP-miR plasmid (Invitrogen) was used to manufacture the EmGFP cassette.

Figure 3:
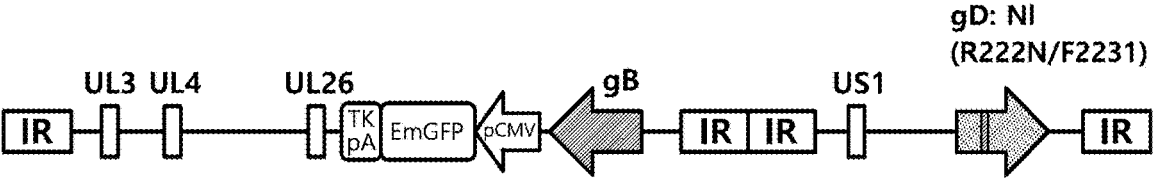
FIG. 3 schematically shows the genomic structure of an HVEM-restricted HSV-1 virus expressing EmGFP.

The genomic structure of KOS-EmGFP-gD-R222N/F223I expressing EmGFP is schematically shown in FIG. 3.

For EmGFP expression, pCMV-EmGFP-tkpA using pCMV as a gene promoter of cytomegalovirus and tkpA as a polyadenylation signal of HSV TK (herpes simplex virus thymidine kinase) was inserted into KOS-37/BAC-gD-R222N/F223I DNA.

All insertion methods were carried out according to the manufacturer's protocol using a counter-selection BAC modification kit (GeneBridges Inc.), as in Example 1.

Specifically, a clone containing KOS-37/BAC-gD-R222N/F223I was transformed with a pRed/ET plasmid expressing RecE and RecT capable of performing the function of homologous recombination (Muyrers J. P. et al.; Nucleic Acids Res. 1999. 27 (6): 1555-1557). A UL26/27-rpsL-neo/kan cassette was manufactured using a set of homologous region primers (forward primer UL26/27-rpsL_ For: SEQ ID NO: 20, reverse primer UL26/27-rpsL_Rev: SEQ ID NO: 21) including a locus at which to introduce a target gene between UL26 and UL27. The clone containing KOS-37/BAC-gD-R222N/F223I DNA and pRed/ET was added with L-arabinose (Sigma-Aldrich) to thus induce homologous recombination, followed by transformation with 200 ng of the manufactured UL26/27-rpsL-neo/kan cassette. The UL26/27-rpsL-neo/kan cassette is inserted into the UL26/27 locus of KOS-37/BAC through homologous recombination. *E. coli* into which UL26/27-rpsL-neo/kan is inserted exhibits kanamycin resistance, but streptomycin resistance is blocked by the rpsL gene. It was inferred for *E. coli* obtained from the kanamycin medium that UL26/27-rpsL-neo/kan was inserted therein, and the final step of inserting a gene was performed.

*E. coli* containing the UL26/27-rpsL-neo/kan cassette was added with L-arabinose (Sigma-Aldrich) activating the function of pRed/ET to thus induce homologous recombination, followed by transformation with 200 ng of a UL26/27-tkpA-EmGFP-pCMV cassette. The UL26/27-tkpA-EmGFP-pCMV cassette was manufactured using a pCDNA6.2-GW/EmGFP-miR plasmid (Invitrogen) as a template, a forward primer UL26/27-tkpA_For (SEQ ID NO: 22), and a reverse primer UL26/27-pCMV_Rev (SEQ ID NO: 23).

Based on the principle whereby streptomycin resistance blocked by rpsL is activated upon replacing the existing UL26/27-rpsL-neo/kan cassette with the inserted UL26/27-tkpA-EmGFP-pCMV, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352). The introduction of tkpA-EmGFP-pCMV at UL26/27 was confirmed through restriction enzyme EcoRI and XhoI treatment and PCR (polymerase chain reaction), and the exact gene sequence was identified through sequencing of the PCR product.

An experiment was conducted for normal expression of a fluorescent protein and production of a virus. The completed KOS-37/BAC-EmGFP-gD-R222N/F223I DNA was extracted using a large-construct DNA purification kit (Macherey-Nagel), after which $2 \times 10^5$ Cre-Vero-HVEM cells were transfected with 1 μg of DNA using a Lipofectamine 2000 reagent (Invitrogen) to remove the BAC gene using Cre recombinase. 3 days after transfection, expression of the EmGFP protein was observed using a fluorescence microscope, and viral production was observed through the formation of Cre-Vero-HVEM cell plaques. After confirmation of plaque formation, the virus-containing cells were collected, subjected three times to a freeze-thaw process (Gierasch W. W. et al.; J. Virol. Methods. 2006. 135:197-206), and sonicated, thus obtaining a KOS-EmGFP-gD-R222N/F223I virus (gDm).

For infection with the KOS-EmGFP-gD-R222N/F223I virus and fluorescence expression thereof, HVEM-free cell lines (J1 and J-Nectin) and cell lines expressing HVEM (J-HVEM) were used. J1 cells are young hamster kidney cell lines that are deficient in the virus HSV-1 receptors HVEM and nectin-1 (Petrovic B. et al., 2017. PLOS Pathog. 19; 13 (4): e1006352). J-Nectin and J-HVEM cell lines are cell lines that overexpress nectin-1 and HVEM respectively in J1 cells (Petrovic B. et al., 2017. PLOS Pathog. 19; 13 (4): e1006352). Each cell line was cultured in DMEM (Welgene) containing 100 U/ml penicillin/100 μg/ml streptomycin (Welgene) and 10% FBS (fetal bovine serum). $1 \times 10^4$ cells were infected at 10 MOI (multiplicity of infection) with the KOS-EmGFP-gD-R222N/F223I virus obtained above, and after 24 hours, the fluorescent protein expression and viral infection were observed using a fluorescence microscope (Baek H. J. et al., Mol. Ther. 2011. 19 (3): 507-514).

Figure 4:
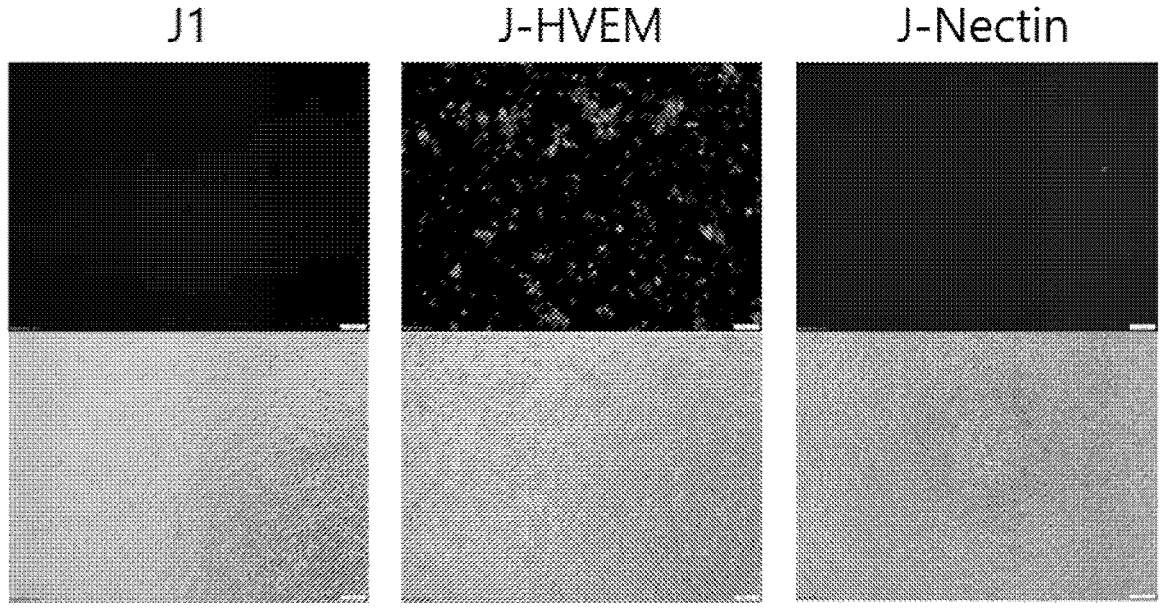
FIG. 4 shows the results of fluorescence expression of an HVEM-restricted HSV-1 virus expressing EmGFP and specific infection of cells having an HVEM receptor therewith.

The results thereof are shown in FIG. 4, upper and lower images of which were taken using a fluorescence microscope and an optical microscope, respectively. With reference to the upper fluorescence microscope images of FIG. 4, it can be seen that the JI cell line and the J-Nectin cell line were not infected, and only the J-HVEM cell line was infected.

Based on the above results, it was confirmed that the propagation of the KOS-EmGFP-gD-R222N/F223I virus (gDm) was easily observed through the expression of the fluorescent protein, as intended, and cell entry became possible using only HVEM as the cell entry receptor, without nectin-1.

<Example 3> Production of HSV-1 Virus Expressing HER2-Targeting Adapter, HSV-1 Virus Expressing EpCAM-Targeting Adapter, and HSV-1 Virus Expressing HER2/EpCAM Dual-Targeting Adapter Each of an adapter-expressing cassette expressing HER2scFv-HveA, an adapter-expressing cassette expressing EpCAM-HveA, and an adapter-expressing cassette expressing both HER2scFv-HveA and EpCAM-HveA was inserted into the UL3/UL4 locus of the KOS-37/BAC-EmGFP-gD-R222N/F223I DNA into which the EmGFP expression cassette (pCMV-EmGFP-tkpA) was inserted, manufactured in Example 2.

Figure 5:
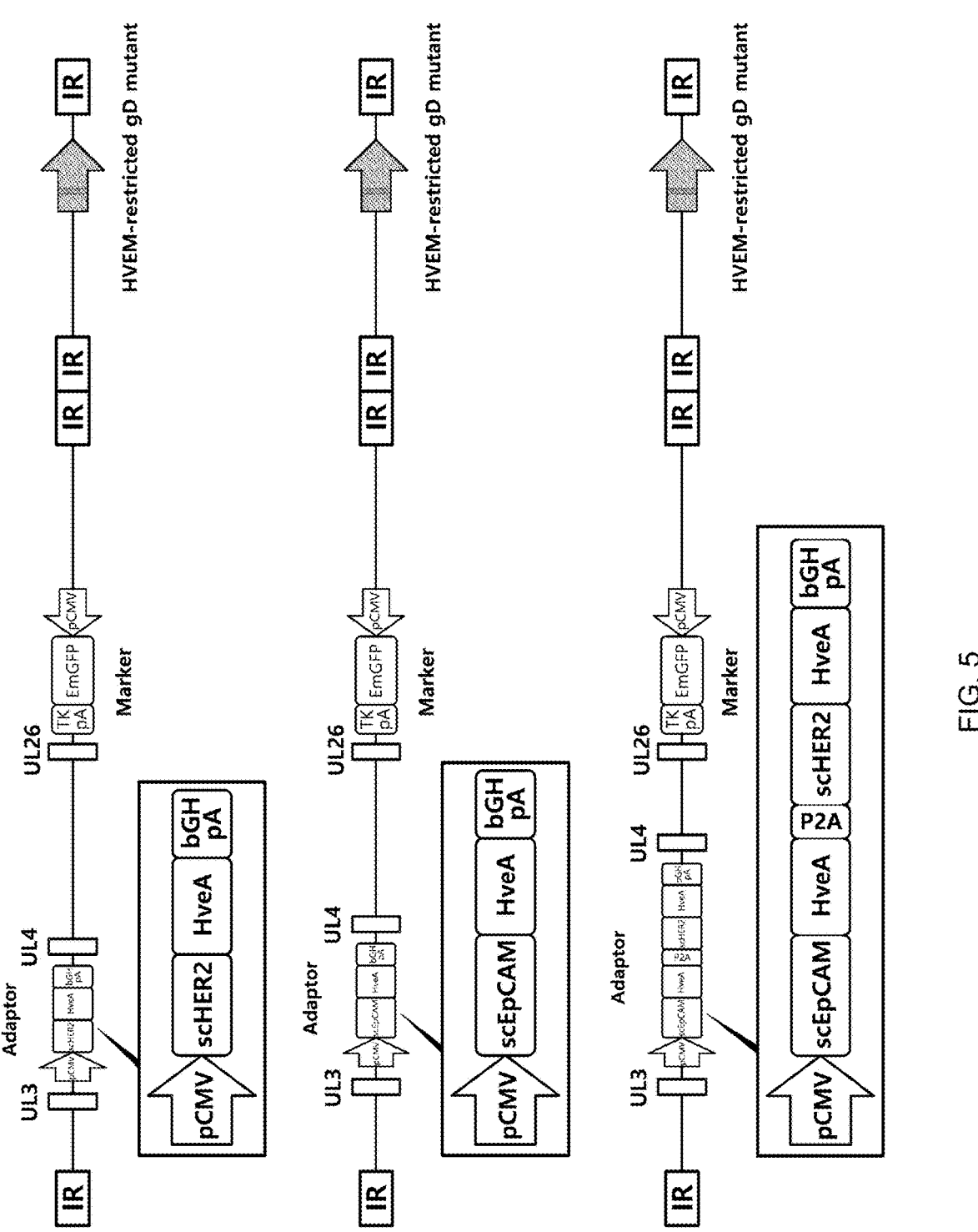
FIG. 5 schematically shows the genomic structure of each of an HSV-1 virus expressing a HER2-targeting adapter, an HSV-1 virus expressing an EpCAM-targeting adapter, and an HSV-1 virus expressing a HER2/EpCAM dual-targeting adapter.
Figure 6:
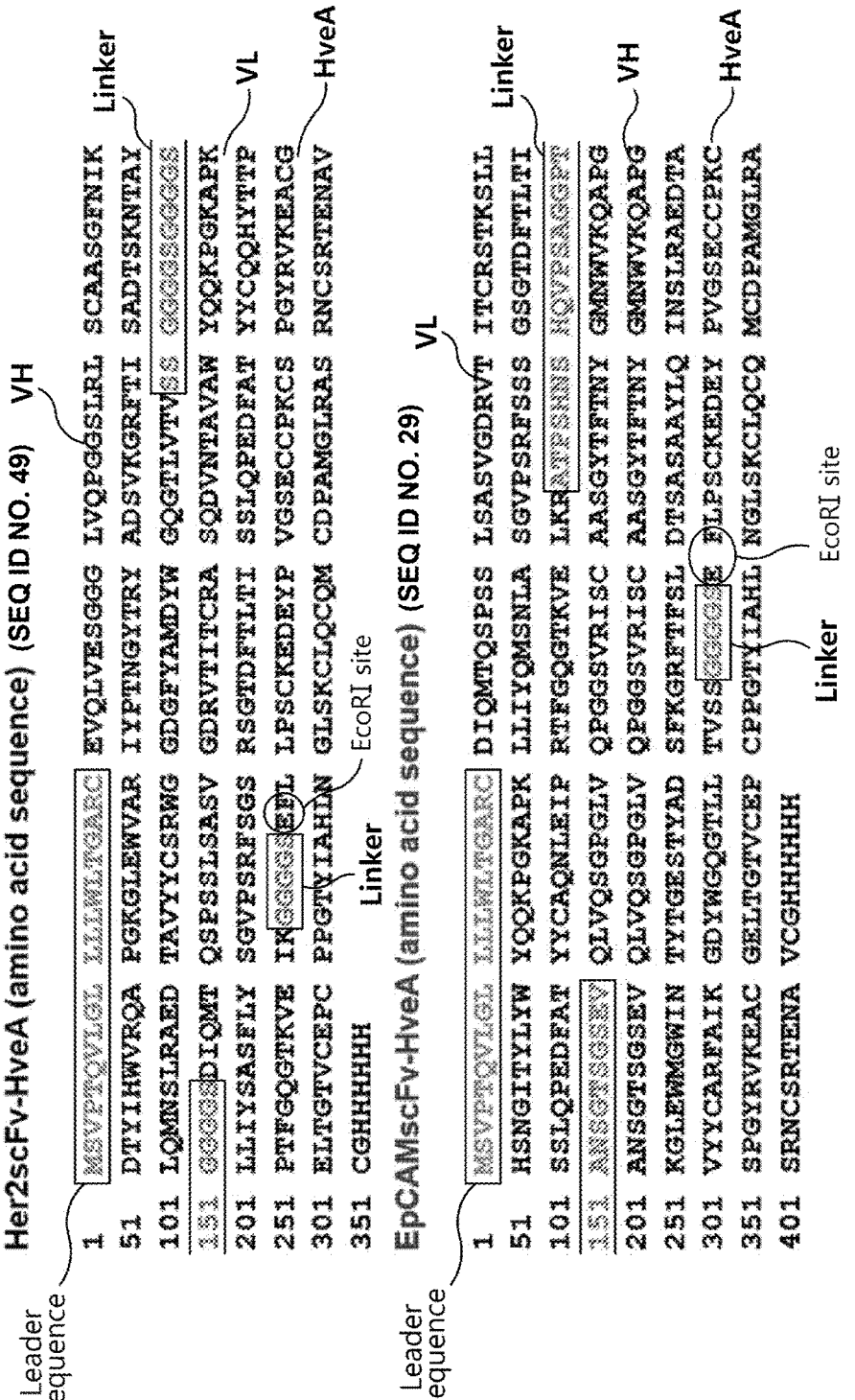
FIG. 6 shows the entire sequence of the HER2scFv-HveA adapter and the EpCAMscFv-HveA adapter and the configuration of the corresponding sequence.

The genomic structure of a KOS-UL3/4-HER2scFv-HveA-EmGFP-gD/R222N/F223I virus into which pCMV-HER2scFv-HveA-bGHpA as the adapter-expressing cassette expressing HER2scFv-HveA was inserted, the genomic structure of a KOS-UL3/4-EpCAMscFv-HveA-EmGFP-gD/R222N/F223I virus into which pCMV-EpCAMscFv-HveA-bGHpA as the adapter-expressing cassette expressing EpCAMscFv-HveA was inserted, and the genomic structure of a KOS-UL3/4-EpCAMscFv-HveA-HER2scFv-HveA-EmGFP-gD/R222N/F223I virus into which pCMV-Ep-CAMscFv-HveA-P2A-HER2scFv-HveA-bGHpA as the adapter-expressing cassette expressing both EpCAM-HveA and HER2scFv-HveA was inserted are schematically shown in FIG. 5, and the entire sequence of the HER2scFv-HveA adapter and the EpCAMscFv-HveA adapter and the configuration of the corresponding sequence are shown in FIG. 6.

Here, scFv for HER2 is configured such that VH of SEQ ID NO: 4 and VL of SEQ ID NO: 5 are linked via a linker peptide of SEQ ID NO: 24, scFv for EpCAM is configured such that VL of SEQ ID NO: 6 and VH of SEQ ID NO: 7 are linked via a linker peptide of SEQ ID NO: 25, and HveA is HveA82 of SEQ ID NO: 8 in the HER2scFv-HveA adapter and the EpCAMscFv-HveA adapter. In addition, in the HER2scFv-HveA adapter and the EpCAMscFv-HveA adapter, the leader sequence of SEQ ID NO: 26 is included at the N-terminus thereof, particularly before VH of HER2scFv and before VL of EpCAMscFv.

EF (base sequence: GAATTC), which is a restriction enzyme EcoRI site for easy cloning, is added after the scFv sequence for HER2 or EpCAM and the NH₂-GGGGS sequence, which is the linker sequence of the HveA sequence. Also, pCMV is the gene promoter of cytomegalovirus, bGH-pA is the bGH-PolyA (bovine growth hormone polyadenylation) signal sequence, and P2A in the adapter-expressing cassette pCMV-HER2scFv-HveA-P2A-Ep-CAMscFv-HveA-bGHpA expressing both HER2scFv-HveA and EpCAM-HveA is 2A of porcine teschovirus-1 (P2A).

Used in the present example, the amino acid sequence and the gene sequence of the full length of the HER2scFv-HveA adapter including the leader sequence are represented in SEQ ID NO: 27 and SEQ ID NO: 28, respectively, and the amino acid sequence and the gene sequence of the full length of the EpCAMscFv-HveA adapter including the leader sequence are represented in SEQ ID NO: 29 and SEQ ID NO: 30, respectively.

The insertion of the HER2scFv-HveA adapter-expressing cassette, the EpCAMscFv-HveA adapter-expressing cassette, and the EpCAM-HveA-HER2scFv-HveA dual adapter-expressing cassette was performed according to the manufacturer's protocol using a counter-selection BAC modification kit (GeneBridges Inc.), as in Examples 1 and 2.

Specifically, the E. coli clone containing the KOS-37/BAC-EmGFP-gD-R222N/F223I genome manufactured in Example 2 was transformed with a pRed/ET plasmid expressing RecE and RecT capable of performing the function of homologous recombination (Muyrers J. P. et al.; Nucleic Acids Res. 1999. 27 (6): 1555-1557). A UL3/4-rpsL-neo/kan cassette was manufactured using a set of homologous region primers (forward primer UL3/4-rpsLneo_for: SEQ ID NO: 31, reverse primer UL3/4-rpsL-neo_rev: SEQ ID NO: 32) including a locus at which to introduce a target gene between UL3 and UL4. The clone containing KOS-37/BAC-EmGFP-gD-R222N/F223I and pRedET was added with L-arabinose (Sigma-Aldrich) to thus induce homologous recombination, followed by transformation with 200 ng of the UL3/4-rpsL-neo/kan cassette manufactured as described above. Through such homologous recombination, the UL3/4-rpsL-neo/kan cassette is inserted into the UL3/4 locus of KOS-37/BAC-EmGFP-gD-R222N/F223I. E. coli into which UL3/4-rpsL-neo/kan is inserted exhibits kanamycin resistance, but streptomycin resistance is blocked by the rpsL gene. It was inferred for E. coli obtained from the kanamycin medium that UL3/4-rpsL-neo/kan was inserted therein, and the final step of inserting a target gene was performed.

E. coli containing the UL3/4-rpsL-neo/kan cassette was added with L-arabinose (Sigma-Aldrich) activating the function of pRed/ET to thus induce homologous recombination, followed by transformation with 200 ng of each of the UL3/4-pCMV-HER2scFv-HveA-bGHpA cassette, the UL3/4-pCMV-EpCAMscFv-HveA-bGHpA cassette, and the UL3/4-pCMV-EpCAMscFv-HveA-P2A-HER2scFv-HveA-bGHpA cassette. The UL3/4-pCMV-HER2scFv-HveA-bGHpA cassette, the UL3/4-pCMV-EpCAMscFv-HveA-bGHpA cassette, and the UL3/4-pCMV-EpCAMscFv-HveA-P2A-HER2scFv-HveA-bGHpA were manufactured using a forward primer UL3/4_pCMV_For (SEQ ID NO: 33) and a reverse primer UL3/4_bGH_poly_R (SEQ ID NO: 34) using, as respective templates, a pCDNA3.1-HER2scFv-HveA plasmid, a pCDNA3.1-EpCAMscFv-HveA plasmid, and pCDNA3.1-pCMV-EpCAMscFv-HveA-P2A-HER2scFv-HveA (Baek H. J. et al., Mol. Ther. 2011. 19 (3): 507-514; Carter P. et al., Proc. Natl. Acad. Sci. USA. 1992, 15; 89 (10): 4285-9, Willuda J. et al., Cancer Res. 1999, 15; 59 (22): 5758-67).

Based on the principle whereby streptomycin resistance blocked by rpsL is activated upon replacing the conventionally inserted UL3/4-rpsL-neo/kan cassette with the above inserted UL3/4-pCMV-HER2scFv-HveA-bGHpA, UL3/4-pCMV-EpCAMscFv-HveA-bGHpA, and UL3/4-pCMV-EpCAMscFv-HveA-P2A-HER2scFv-HveA-bGHpA, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352). The introduction of the UL3/4-pCMV-HER2scFv-HveA-bGHpA, UL3/4-pCMV-EpCAMscFv-HveA-bGHpA and UL3/4-pCMV-EpCAMscFv-HveA-P2A-HER2scFv-HveA-bGHpA at UL3/4 was confirmed through restriction enzyme EcoRI and XhoI treatment and PCR (polymerase chain reaction), and the exact gene sequence was identified through sequencing of the PCR product.

The completed KOS-37/BAC-UL3/4_HER2scFv-HveA-EmGFP-gD-R222N/F223I, KOS-37/BAC-UL3/4_EpCAM-scFv-HveA-EmGFP-gD-R222N/F223I, and KOS-37/BAC-UL3/4_EpCAMscFv-HveA-P2A-HER2scFv-HveA-Em-GFP-gD-R222N/F223I DNA were extracted using a large-construct DNA purification kit (Macherey-Nagel), after which 2×10⁵ Cre-Vero-HVEM cells were transfected with 1 µg of DNA using a Lipofectamine 2000 reagent (Invitrogen) to remove the BAC gene using Cre recombinase. 3 days after transfection, the fluorescence expression of the EmGFP protein and the formation of cell plaques were observed using a fluorescence microscope. After confirmation of plaque formation, the virus-containing cells were collected, subjected three times to a freeze-thaw process (Gierasch W. W. et al.; J. Virol. Methods. 2006. 135:197-206), and sonicated, ultimately obtaining a KOS-UL3/4_HER2scFv-HveA-EmGFP-gD-R222N/F223I virus (HADa-S) expressing the HER2-targeting adapter, a KOS-UL3/4_Ep-CAMscFv-HveA-EmGFP-gD/R222N/F223I virus (EADa-S) expressing the EpCAM-targeting adapter, and a KOS-UL3/4_EpCAMscFv-HveA-P2A-HER2scFv-HveA-Em-GFP-gD/R222N/F223I virus (EADa-HADa-D) expressing the HER2/EpCAM dual-targeting adapter.

<Example 4> Production of HSV-1 Virus Having HER2-Targeting Modified Glycoprotein gH and HSV-1 Virus Having HER2-Targeting Modified Glycoprotein gH and Expressing HER2-Targeting Adapter For the production of a retargeting HSV capable of targeting a target molecule expressed in specific cancer, a ligand (HER2 scFv) that recognizes HER2 specifically expressed in cancer cells was inserted between amino acids 29 and 30 of the amino acid sequence of gH (GenBank Accession No. ASM47773, SEQ ID NO: 3), which is a glycoprotein of HSV-1. A gene capable of expressing HER2scFv was inserted between amino acids 29 and 30 of the glycoprotein gH in the KOS-37/BAC-EmGFP-gD-R222N/F223I DNA and the KOS-37/BAC-UL3/4_HER2scFv-HveA-EmGFP-gD/R222N/F223I DNA manufactured in Examples 2 and 3.

The genome structure of each of the KOS-gH/HER2scFv-EmGFP-gD/R222N/F223I virus (HgH-S) and the KOS-UL3/4_HER2scFv-HveA-gH/HER2scFv-EmGFP-gD/R222N/F223I virus (HADa-HgH-D), in which the HER2scFv ligand was inserted into the gH of HSV-1, is shown in FIG. 7, and the entire sequence of the gH-HER2scFv ligand and the construction of the corresponding sequence are shown in FIG. 8. Here, scFv for HER2 is configured such that VH of SEQ ID NO: 4 and VL of SEQ ID NO: 5 are connected via a linker peptide of SEQ ID NO: 24, and the linker peptide of SEQ ID NO: 35 is linked to the N-terminus of the scFv, and the linker peptide of SEQ ID NO: 36 is linked to the C-terminus thereof.

The amino acid sequence and the gene sequence of the full length of HER2scFv used in the present example are represented in SEQ ID NO: 37 and SEQ ID NO: 38, respectively.

The insertion of the gH-HER2scFv ligand was performed according to the manufacturer's protocol using a counter-selection BAC modification kit (GeneBridges Inc.), as in Examples 1, 2 and 3.

Specifically, the E. coli clone containing the KOS-37/BAC-EmGFP-gD-R222N/F223I DNA and the KOS-37/BAC-UL3/4_HER2scFv-HveA-EmGFP-gD-R222N/F223I DNA manufactured in Examples 2 and 3 was transformed with a pRed/ET plasmid expressing RecE and RecT capable of performing the function of homologous recombination (Muyrers J. P. et al.; Nucleic Acids Res. 1999. 27 (6): 1555-1557). A gH29/30-rpsL-neo/kan cassette was manufactured using a set of homologous region primers (forward primer gH29/30-rpsL-neo_for: SEQ ID NO: 39, reverse primer gH29/30-rpsL-neo_rev: SEQ ID NO: 40) including a locus at which to introduce a target gene between amino acids 29 and 30 of gH. The clone containing each of KOS-37/BAC-EmGFP-gD-R222N/F223I DNA and KOS-37/BAC-UL3/4_HER2scFv-HveA-EmGFP-gD-R222N/F223I DNA and pRed/ET was added with L-arabinose (Sigma-Aldrich) to thus induce homologous recombination, followed by transformation with 200 ng of the gH29/30-rpsL-neo/kan cassette manufactured as described above. Through such homologous recombination, the gH29/30-rpsL-neo/kan cassette is inserted at the position between amino acids 29 and 30 of gH. E. coli into which gH29/30-rpsL-neo/kan is inserted exhibits kanamycin resistance, but streptomycin resistance is blocked by the rpsL gene. It was inferred for E. coli obtained from the kanamycin medium that gH29/30-rpsL-neo/kan was inserted therein, and the final step of inserting a target gene was performed.

E. coli containing the gH29/30-rpsL-neo/kan cassette was added with L-arabinose (Sigma-Aldrich) activating the function of pRed/ET to thus induce homologous recombination, followed by transformation with 200 ng of a gH29/30-HER2scFv ligand. The gH29/30-HER2scFv ligand was manufactured using a forward primer gH29/30-scFv_For (SEQ ID NO: 41) and a reverse primer gH29/30-scFv_Rev (SEQ ID NO: 42) using, as a template, a pCAGGSMCS-gH-HER2scFv plasmid. The pCAGGSMCS-gH-HER2scFv plasmid was manufactured by inserting HER2scFv into a pCAGGSMCS plasmid (Atanasiu D. et al., J. Virol. 2013 November 87 (21): 11332-11345), and, in detail, was manufactured by treating a pCAGGSMCS plasmid and HER2scFv amplified via PCR (Carter P. et al., Proc. Natl. Acad. Sci. USA. 1992, 15; 89 (10): 4285-9) with a NotI restriction enzyme (NEB, R3189) and joining the pCAGGSMCS plasmid and the HER2scFv, which were cleaved by NotI, using T4 DNA ligase (NEB, M0202).

Based on the principle whereby streptomycin resistance blocked by rpsL is activated upon replacing the conventionally inserted gH29/30-rpsL-neo/kan cassette with the above inserted gH29/30-HER2scFv, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352), the introduction of HER2scFv at gH29/30 was confirmed through restriction enzyme EcoRI and XhoI treatment and PCR (polymerase chain reaction), and the exact gene sequence was identified through sequencing of the PCR product.

The completed KOS-37/BAC-gH/HER2scFv-EmGFP-gD-R222N/F223I DNA and KOS-37/BAC-UL3/4_HER2scFv-HveA-gH/HER2scFv-EmGFP-gD-R222N/F223I DNA were extracted using a large-construct DNA purification kit (Macherey-Nagel), after which $2\times10^5$ Cre-Vero-HVEM cells were transfected with 1 μg of DNA using a Lipofectamine 2000 reagent (Invitrogen) to remove the BAC gene using Cre recombinase. 3 days after transfection, the fluorescence expression of the EmGFP protein and the formation of cell plaques were observed using a fluorescence microscope. After confirmation of plaque formation, the virus-containing cells were collected, subjected three times to a freeze-thaw process (Gierasch W. W. et al.; J. Virol. Methods. 2006. 135:197-206), and sonicated, ultimately obtaining a KOS-gH/HER2scFv-EmGFP-gD-R222N/F223I virus (HgH-S) and a KOS-UL3/4_HER2scFv-HveA-gH/HER2scFv-EmGFP-gD-R222N/F223I virus (HADa-HgH-D).

<Example 5> Production of HSV-1 Virus Having EpCAM-Targeting Modified Glycoprotein gH and HSV-1 Virus Having EpCAM-Targeting Modified Glycoprotein gH and Expressing EpCAM-Targeting Adapter For the production of a retargeting HSV capable of targeting a target molecule expressed in specific cancer, a ligand (EpCAM scFv) that recognizes EpCAM specifically expressed in cancer cells was inserted between amino acids 29 and 30 of the amino acid sequence of gH (GenBank Accession No. ASM47773, SEQ ID NO: 3), which is a glycoprotein of HSV-1. A gene capable of expressing EpCAMscFv was inserted between amino acids 29 and 30 of the glycoprotein gH in the KOS-37/BAC-EmGFP-gD-R222N/F223I DNA and the KOS-37/BAC-UL3/4_EpCAM-scFv-HveA-EmGFP-gD/R222N/F223I (EADa-S) DNA manufactured in Examples 2 and 3.

Figure 10:
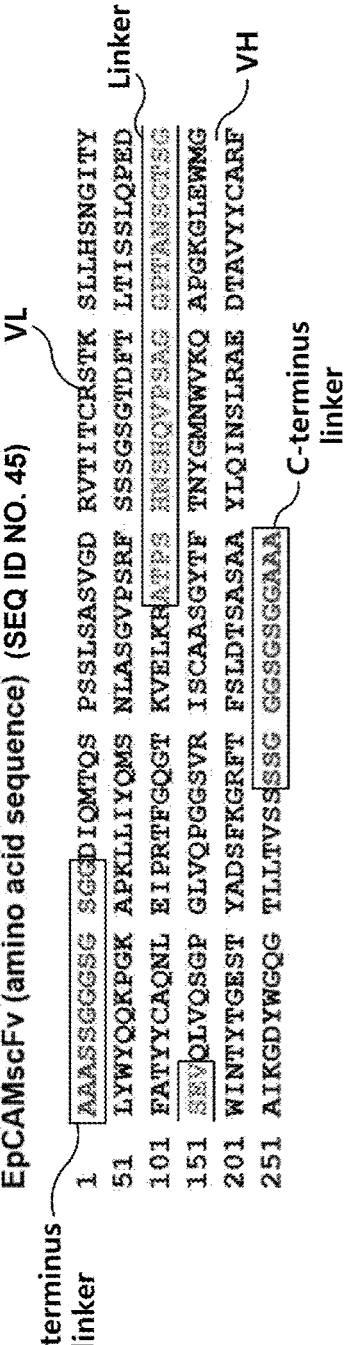
FIG. 10 shows the entire amino acid sequence of the EpCAMscFv ligand inserted and fused into gH and the configuration of the corresponding sequence.

The genomic structure of each of the KOS-gH/EpCAM-scFv-EmGFP-gD/R222N/F223I virus (EgH-S) and the KOS-UL3/4_EpCAMscFv-HveA-gH/EpCAMscFv-EmGFP-gD/R222N/F223I virus (EADa-EgH-D), in which the EpCAMscFv ligand was inserted into the gH of HSV-1, is shown in FIG. 9, and the entire sequence of the gH-EpCAMscFv ligand and the construction of the corresponding sequence are shown in FIG. 10. Here, scFv for EpCAM is configured such that VL of SEQ ID NO: 6 and VH of SEQ ID NO: 7 are linked via a linker peptide of SEQ ID NO: 25, and the linker peptide of SEQ ID NO: 43 is linked to the N-terminus of this scFv, and the linker peptide of SEQ ID NO: 44 is linked to the C-terminus thereof.

The amino acid sequence and the gene sequence of EpCAMscFv used in the present example are represented in SEQ ID NO: 45 and SEQ ID NO: 46, respectively.

The insertion of the gH-EpCAMscFv ligand was performed according to the manufacturer's protocol using a counter-selection BAC modification kit (GeneBridges Inc.), as in Example 4.

Specifically, the E. coli clone containing the KOS-37/BAC-EmGFP-gD-R222N/F223I DNA and the KOS-37/BAC-UL3/4_EpCAMscFv-HveA-EmGFP-gD-R222N/F223I DNA manufactured in Examples 2 and 3 was transformed with a pRed/ET plasmid expressing RecE and RecT capable of performing the function of homologous recombination (Muyrers J. P. et al.; Nucleic Acids Res. 1999. 27 (6): 1555-1557). A gH29/30-rpsL-neo/kan cassette was manufactured using a set of homologous region primers (forward primer gH29/30-rpsL-neo_for: SEQ ID NO: 39, reverse primer gH29/30-rpsL-neo_rev: SEQ ID NO: 40) including a locus at which to introduce a target gene between amino acids 29 and 30 of gH. The clone containing each of KOS-37/BAC-EmGFP-gD-R222N/F223I DNA and KOS-37/BAC-UL3/4_EpCAMscFv-HveA-EmGFP-gD-R222N/F223I DNA and pRed/ET was added with L-arabinose (Sigma-Aldrich) to thus induce homologous recombination, followed by transformation with 200 ng of the gH29/30-rpsL-neo/kan cassette manufactured as described above. Through such homologous recombination, the gH29/30-rpsL-neo/kan cassette is inserted between amino acids 29 and 30 of gH. E. coli into which gH29/30-rpsL-neo/kan is inserted exhibits kanamycin resistance, but streptomycin resistance is blocked by the rpsL gene. It was inferred for E. coli obtained from the kanamycin medium that gH29/30-rpsL-neo/kan was inserted therein, and the final step of inserting a target gene was performed.

E. coli containing the gH29/30-rpsL-neo/kan cassette was added with L-arabinose (Sigma-Aldrich) activating the function of pRed/ET to thus induce homologous recombination, followed by transformation with 200 ng of a gH29/30-EpCAMscFv ligand. The gH29/30-EpCAMscFv ligand was manufactured using a forward primer gH29/30-scFv_For (SEQ ID NO: 41) and a reverse primer gH29/30_scFv_Rev (SEQ ID NO: 42) using, as a template, a pCAGGSMCS-gH-EpCAMscFv plasmid. The pCAGGSMCS-gH-EpCAMscFv plasmid was manufactured by inserting EpCAMscFv into a pCAGGSMCS plasmid (Atanasiu D. et al., J. Virol. 2013 November 87 (21): 11332-11345), and, in detail, was manufactured by treating a pCAGGSMCS plasmid and EpCAMscFv amplified via PCR (Willuda J. et al., Cancer Res. 1999, 15; 59 (22): 5758-67) with a NotI restriction enzyme (NEB, R3189) and joining the pCAGGSMCS plasmid and the EpCAMscFv, which were cleaved by NotI, using T4 DNA ligase (NEB, M0202).

Based on the principle whereby streptomycin resistance blocked by rpsL is activated upon replacing the conventionally inserted gH29/30-rpsL-neo/kan cassette with the above inserted gH29/30-EpCAMscFv, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352). The introduction of EpCAMscFv at gH29/30 was confirmed through restriction enzyme EcoRI and XhoI treatment and PCR (polymerase chain reaction), and the exact gene sequence was identified through sequencing of the PCR product.

The completed KOS-37/BAC-gH_EpCAMscFv-EmGFP-gD-R222N/F223I and KOS-37/BAC-UL3/4_EpCAMscFv-HveA-gH/EpCAMscFv-EmGFP-gD-R222N/F223I DNA were extracted using a large-construct DNA purification kit (Macherey-Nagel), after which $2 \times 10^5$ Cre-Vero-HVEM cells were transfected with 1 μg of DNA using a Lipofectamine 2000 reagent (Invitrogen) to remove the BAC gene using Cre recombinase. 2 days after transfection, the fluorescence expression of the EmGFP protein and the formation of cell plaques were observed using a fluorescence microscope. After confirmation of plaque formation, the virus-containing cells were collected, subjected three times to a freeze-thaw process (Gierasch W. W. et al.; J. Virol. Methods. 2006.135:197-206), and sonicated, ultimately obtaining a KOS-gH/EpCAMscFv-EmGFP-gD-R222N/F223I virus (EgH-S) and a KOS-gH/EpCAMscFv-UL3/4_EpCAMscFv-HveA-EmGFP-gD-R222N/F223I virus (EADa-EgH-D).

<Example 6> Measurement of Activity of HER2 Dual-Targeting Oncolytic Virus

In order to confirm the expression level of the HER2scFv-HveA adapter as well as the viral proliferation and amplification of the KOS-UL3/4_HER2scFv-HveA-EmGFP-gD-R222N/F223I virus (HADa-S) expressing the HER2scFv-HveA adapter, the KOS-gH/HER2scFv-EmGFP-gD-R222N/F223I virus (HgH-S) expressing HER2scFv in gH, and the KOS-UL3/4_HER2scFv-HveA-gH/HER2scFv-EmGFP-gD-R222N/F223I (HADa-HgH-D) dual-targeting virus expressing the HER2scFv-HveA adapter and HER2scFv in gH, as manufactured in Examples 3 and 4, the following experiment was performed.

In order to perform the viral proliferation experiment, $2.0 \times 10^5$ Vero-HVEM cells and SK-OV-3 cells were applied on a 12 well plate.

An HSV-1 wild-type virus (KOS), the virus gDm expressing the fluorescent protein EmGFP manufactured in Example 2 and enabling cell entry using only HVEM as a cell receptor, the virus HADa-S expressing the HER2scFv-HveA adapter manufactured in Example 3, the virus HgH-S having the HER2scFv ligand in gH manufactured in Example 4, and the dual-targeting virus HADa-HgH-D having the HER2scFv ligand in gH and expressing the HER2scFv-HveA adapter manufactured in Example 4 were diluted and used for infection so that 20-50 viruses were contained in a single well. After 90 minutes, in order to remove the remaining initial virus and prevent the viral proliferation, the medium that was used was replaced with a medium containing 0.2% methylcellulose. After 3 days, viral proliferation was measured through the size of a virus plaque using a fluorescence microscope.

Figure 11:
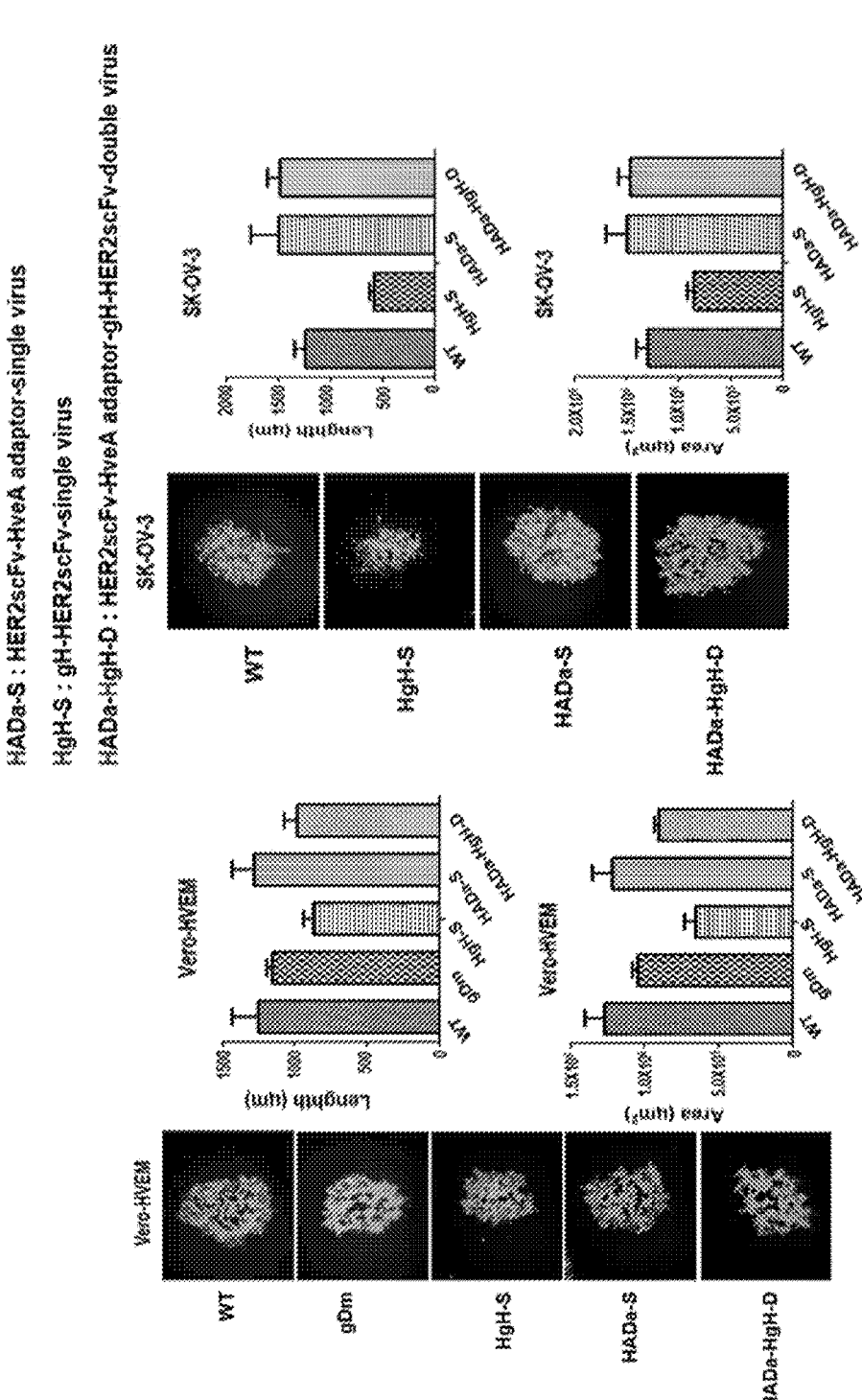
FIG. 11 shows the results of measurement of the proliferation, in Vero-HVEM cells and SK-OV-3 cells, of a virus (gDm) expressing a fluorescent protein EmGFP and enabling cell entry using only HVEM as a cell receptor, a virus (HADa-S) expressing a HER2scFv-HveA adapter, a virus (HgH-S) having a HER2scFv ligand in gH, and a dual-targeting virus (HADa-HgH-D) having a HER2scFv ligand in gH and expressing a HER2scFv-HveA adapter.

The results thereof are shown in FIG. 11. As is apparent from FIG. 11, in the Vero-HVEM cell line, the plaque sizes of gDm, HgH-S, HADa-S and HADa-HgH-D were 18%, 49%, 4%, and 29% smaller, respectively, than that of the wild-type virus (KOS). In SK-OV-3 cells as the HER2-expressing cell line, the plaque size of HgH-S was reduced by 53% compared to the wild-type virus (KOS), but HADa-S and HADa-HgH-D viruses were increased by 20% and 19%, respectively. The reason why the plaque size of HgH-S was decreased is deemed to be that, when gD binds to the entry receptor, gH plays a role in inducing cell fusion by transmitting an activation signal to gB through such binding, and also that endocytosis is induced through binding to integrins, and thus it is judged that viral proliferation or replication is inhibited by affecting such signal transmission or endocytosis due to structural changes through insertion of scFv into gH.

In order to perform the virus replication experiment, $1.0 \times 10^4$ Vero-HVEM cells were applied on a 96 well plate. The gDm, HgH-S expressing the HER2scFv ligand in gH, HADa-S expressing the HER2scFv-HveA adapter, and dual-targeting HADa-HgH-D viruses were used for infection at 0.1 MOI. After 90 minutes, the medium that was used was replaced with a fresh medium in order to remove the remaining initial virus. A virus culture solution was obtained at 3, 24, and 48 hours after infection, and the number of viruses in the culture solution was measured.

Figure 12:
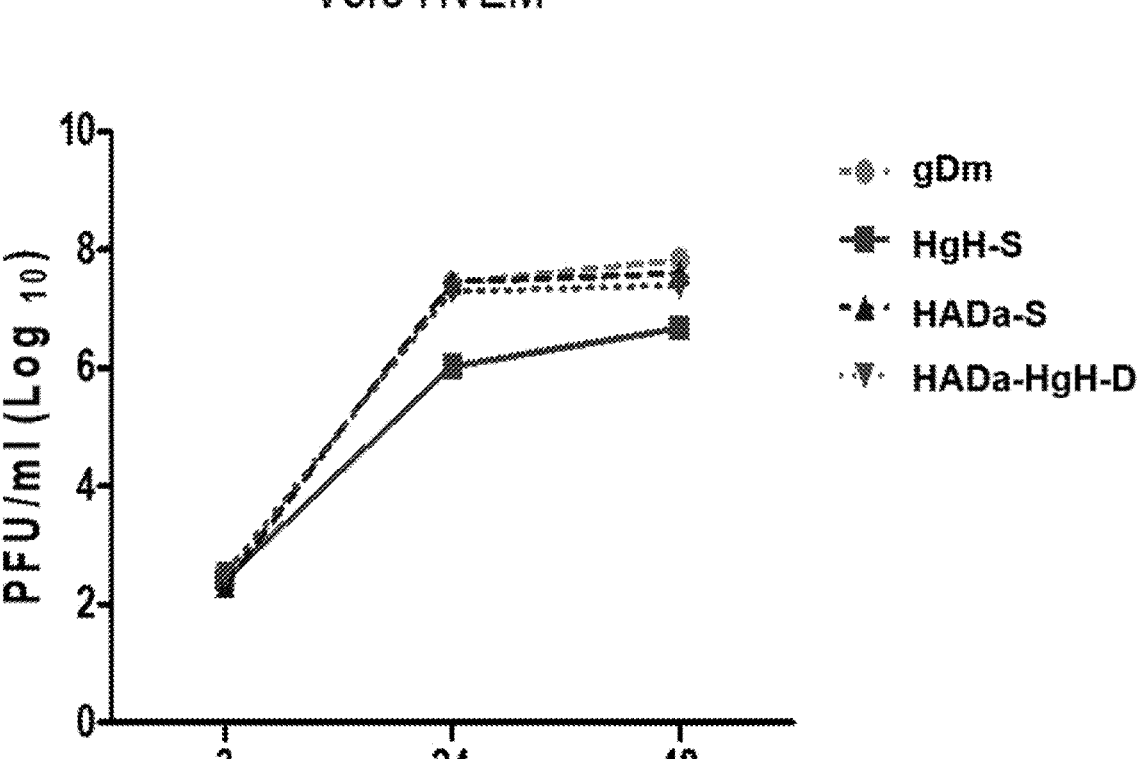
FIG. 12 shows the results of measurement of the amplification, in Vero-HVEM cells, of a virus (gDm) expressing a fluorescent protein EmGFP and enabling cell entry using only HVEM as a cell receptor, a virus (HADa-S) expressing a HER2scFv-HveA adapter, a virus (HgH-S) having a HER2scFv ligand in gH, and a dual-targeting virus (HADa-HgH-D) having a HER2scFv ligand in gH and expressing a HER2scFv-HveA adapter.

The results thereof are shown in FIG. 12. As is apparent from FIG. 12, although the virus propagation activity of gDm, HADa-S and HADa-HgH-D was similar in the Vero-HVEM cell line, it was confirmed that the virus propagation activity in HgH-S was reduced due to the decreased virus proliferation ability, as in the results of FIG. 11.

In order to perform the experiment to measure the expression level of the adapter, $2.0 \times 10^5$ Vero-HVEM and SK-OV-3 cells were applied on a 12-well plate. Then, gDm, HgH-S expressing the HER2scFv ligand in gH, HADa-S expressing the HER2scFv-HveA adapter, and the dual-targeting HADa-HgH-D virus were used for infection at 0.1 MOI. After 90 minutes, the medium that was used was replaced with a fresh medium without FBS in order to remove the remaining initial virus. 48 hours after infection, a virus culture solution was obtained, and protein expression levels were measured through Western blotting in order to measure the adapter in the culture solution.

Figure 13:
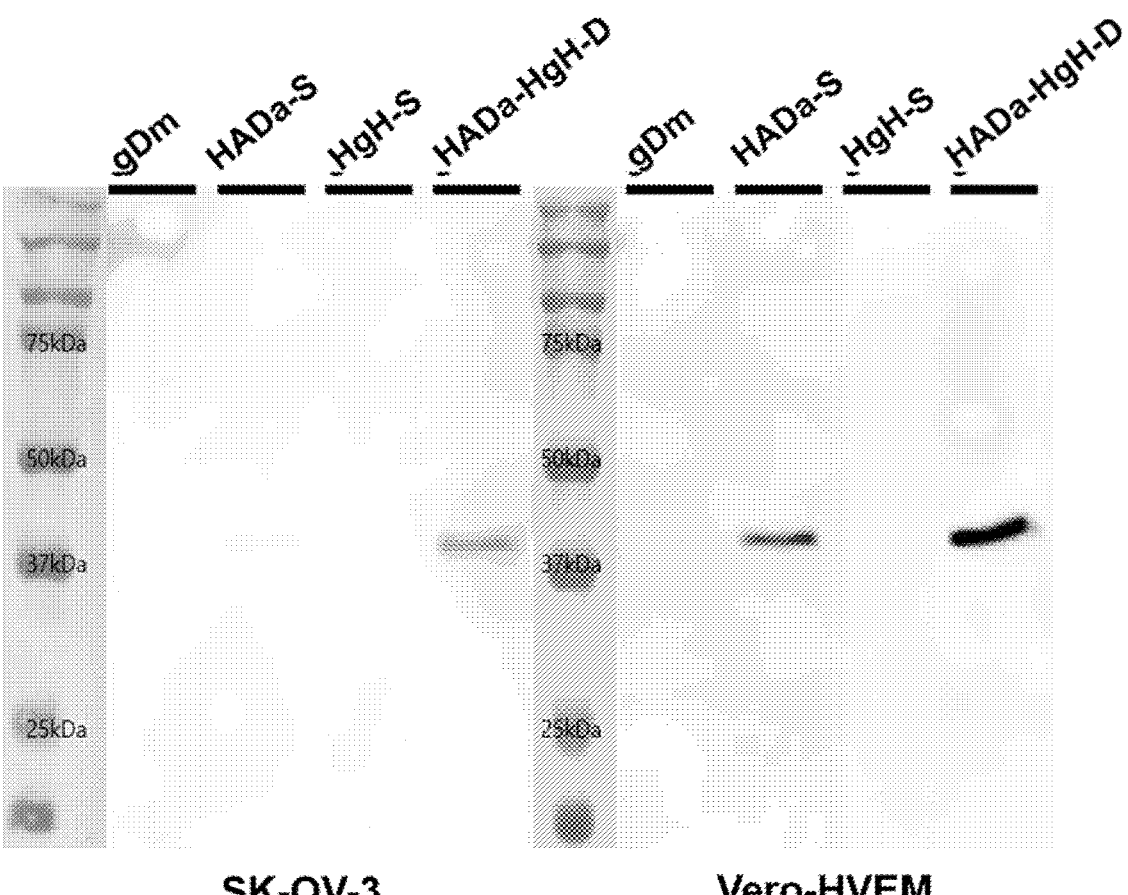
FIG. 13 shows the results of measurement of the expression level of the HER2scFv-HveA adapter of a virus (gDm) expressing a fluorescent protein EmGFP and enabling cell entry using only HVEM as a cell receptor, a virus (HADa-S) expressing a HER2scFv-HveA adapter, a virus (HgH-S) having a HER2scFv ligand in gH, and a dual-targeting virus (HADa-HgH-D) having a HER2scFv ligand in gH and expressing a HER2scFv-HveA adapter, in Vero-HVEM cells and SK-OV-3 cells.

The results thereof are shown in FIG. 13. As is apparent from FIG. 13, in the Vero-HVEM cell line, the HADa-HgH-D dual-targeting virus expressed the adapter in an amount as large as at least 3 times compared to the HADa-S virus expressing only the adapter. However, the adapter was not measured in gDm and HgH-S virus culture solutions having no adapter. In SK-OV-3 cells expressing HER2, only the adapter of the HADa-HgH-D dual-targeting virus was detected. This is because the HADa-HgH-D dual-targeting virus exhibits a higher infection rate in the cell line expressing HER2 compared to the HADa-S virus, so the expression of the adapter is proportionally higher.

Consequently, the HADa-HgH-D dual-targeting virus was confirmed to be relatively improved in view of the viral proliferation and amplification and the adapter expression level compared to other viruses.

<Example 7> Infection and Cytotoxicity of HER2-Expressing Cancer Cells Using HER2 Dual-Targeting Oncolytic Virus An experiment was performed in a HER2-expressing cancer cell line using gDm, HgH-S expressing the HER2scFv ligand in gH, HADa-S expressing the HER2scFv-HveA adapter, and the dual-targeting HADa-HgH-D virus expressing the HER2scFv-HveA adapter and the HER2scFv ligand in gH, manufactured in Examples 2, 3 and 4. In order to confirm whether each virus induces viral infection into surrounding cancer cells due to the HER2scFv ligand expressed in the glycoprotein gH or due to the adapter and whether it induces cytotoxicity after infection, the following experiment was conducted.

The cell lines that were used in the experiment were a cell line not expressing HER2 (MDA-MB-231) and cell lines expressing HER2 (SK-OV-3, MCF-7, MDA-MB-453, and BT-474). For breast cancer cell lines MDA-MB-231 (ATCC, HTB-26), MCF-7 (ATCC, HTB-22), and BT-474 (ATCC, HTB-20), and an ovarian cancer cell line SK-OV-3 (ATCC, HTB-77), culture was performed using DMEM containing 100 U/ml penicillin/100 µg/ml streptomycin (Welgene) and 10% FBS, and for a breast cancer cell line MDA-MB-453 (ATCC, HTB-131), culture was performed using an RPMI 1640 medium containing 100 U/ml penicillin/100 µg/ml streptomycin (Welgene) and 10% FBS.

For a HER2-specific viral infection experiment, $8 \times 10^3$ SK-OV-3 and MDA-MB-231, $4.0 \times 10^4$ MCF-7, $8.0 \times 10^4$ MDA-MB-453, and $7.0 \times 10^4$ BT-474 cell lines were used at 2 MOI and infected with HgH-S expressing the HER2scFv ligand in gH, HADa-S expressing the HER2scFv-HveA adapter, the dual-targeting HADa-HgH-D virus, and as a control, HER2-non-targeting gDm virus. After 90 minutes, the medium that was used was replaced with a fresh medium in order to remove the remaining initial virus. 2 days after infection, viral infection was confirmed through EmGFP fluorescence expression in each cell line (Baek H. J. et al., Mol. Ther. 2011. 19 (3): 507-514). Also, in order to measure cytotoxicity for 4 days after infection, the extent of color development of formazan, which is a color-developing material formed only in living cells using an EZ-Cytox (DoGenBio) reagent, was measured at 450 nm using an ELISA reader. Absorbance was quantified to determine the cytotoxicity of cancer cell lines due to each virus.

Figure 14:
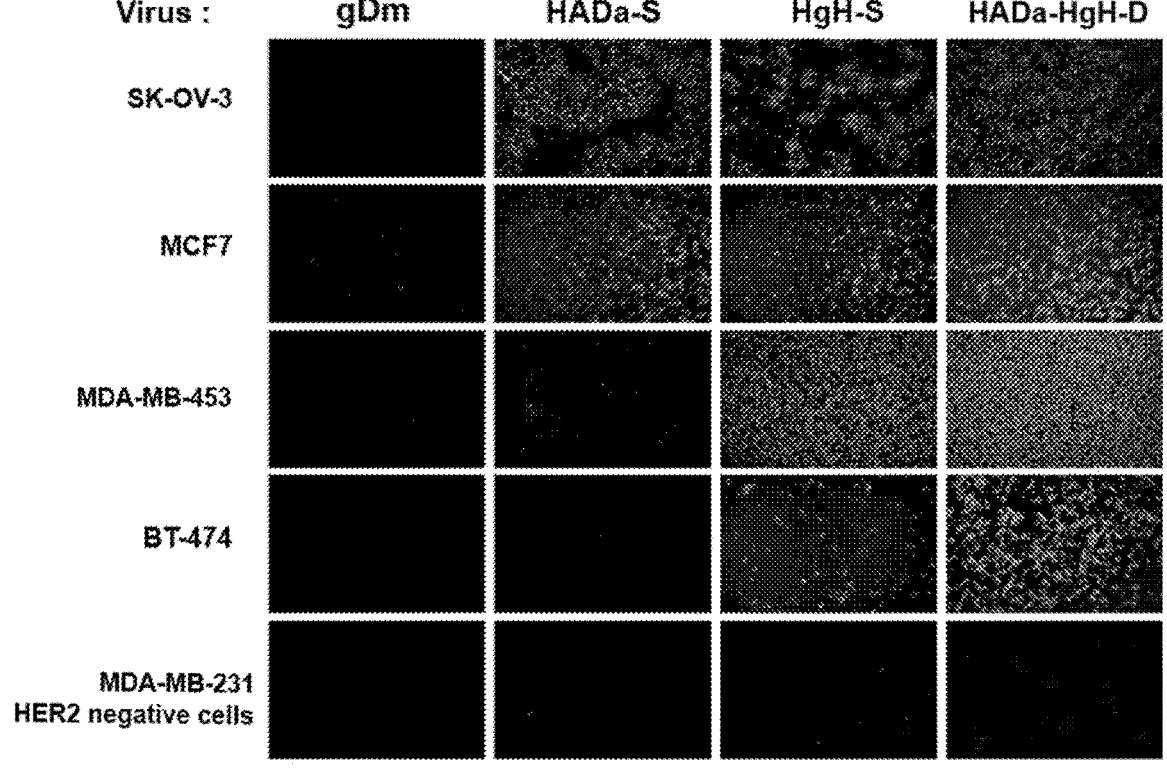
FIG. 14 shows the results of specific infection depending on the expression of HER2 in SK-OV-3 cells and the like, of a virus (gDm) expressing a fluorescent protein EmGFP and enabling cell entry using only HVEM as a cell receptor, a virus (HADa-S) expressing a HER2scFv-HveA adapter, a virus (HgH-S) having a HER2scFv ligand in gH, and a dual-targeting virus (HADa-HgH-D) having a HER2scFv ligand in gH and expressing a HER2scFv-HveA adapter.

The results thereof are shown in FIG. 14. As is apparent from FIG. 14, the HADa-S virus expressing the adapter had a high infection rate in SK-OV-3 and MCF7 cells, but a low infection rate was observed in MDA-MB-453 and BT-474. The HgH-S virus expressing the HER2scFv ligand in gH had a high infection rate in SK-OV-3, MCF7, and MDA-MB-453 cells, but a low infection rate was observed in BT-474. Unlike the virus that expresses each of the ligand and the adapter, the dual-targeting HADa-HgH-D virus was observed to exhibit a high infection rate in all cells expressing HER2. However, the gDm virus did not infect cancer cell lines because it was not targeted to HER2, and infection with all viruses was not observed in MDA-MB-231 cells not expressing HER2, as a control. The low infection rate in MDA-MB-453 and BT-474 is deemed to be due to the cell morphology and characteristics of MDA-MB-453 and BT-474 and the initial low infection with the HADa-S virus.

Figure 15:
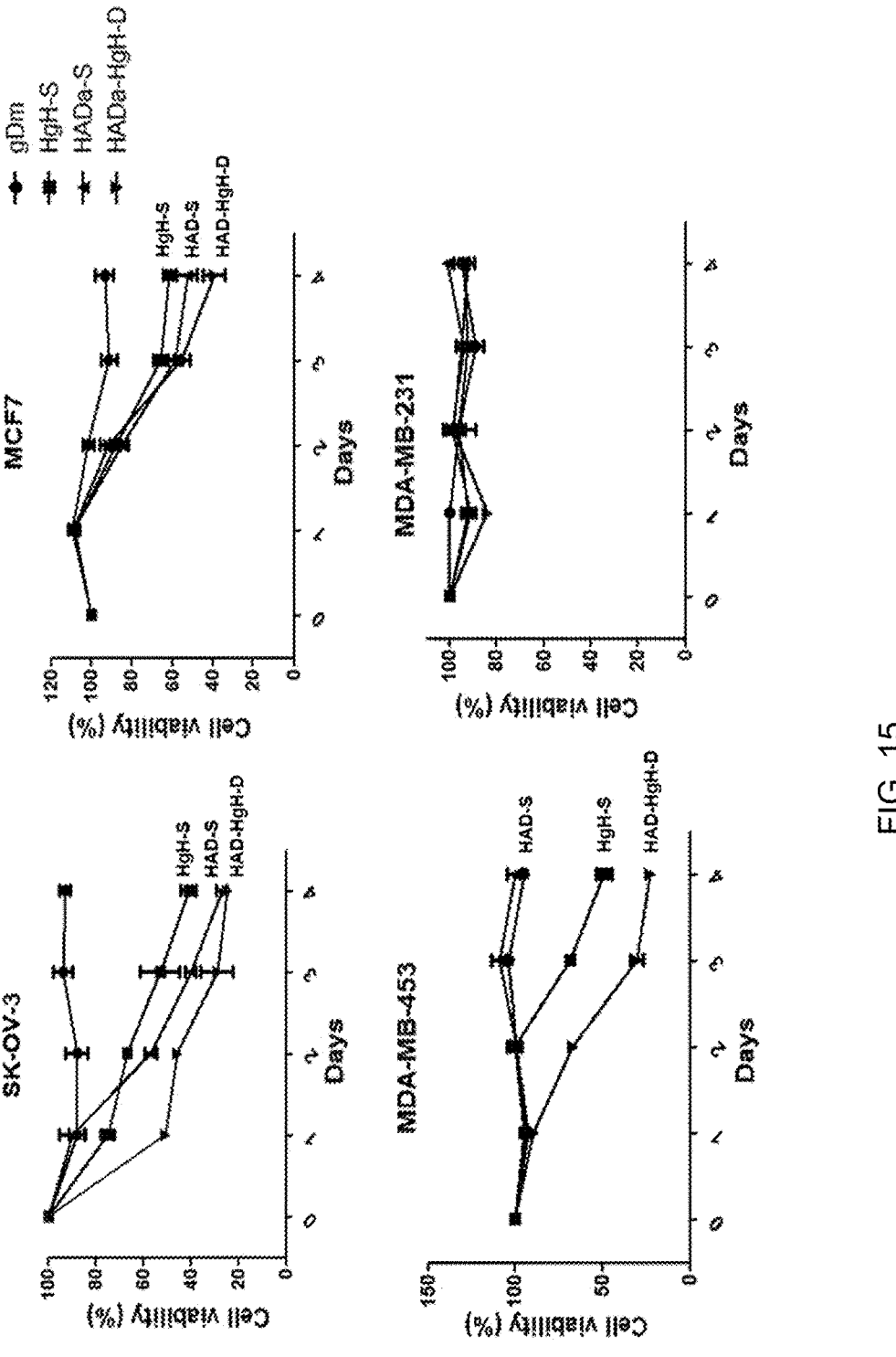
FIG. 15 shows the results of specific cell death depending on the expression of HER2 in SK-OV-3 cells and the like, of a virus (gDm) expressing a fluorescent protein EmGFP and enabling cell entry using only HVEM as a cell receptor, a virus (HADa-S) expressing a HER2scFv-HveA adapter, a virus (HgH-S) having a HER2scFv ligand in gH, and a dual-targeting virus (HADa-HgH-D) having a HER2scFv ligand in gH and expressing a HER2scFv-HveA adapter.

In addition, FIG. 15 shows the results of observation of the cytotoxicity of cancer cells due to the virus for 4 days after infection. The HgH-S, HADa-S, and HADa-HgH-D viruses exhibited respective cell viability values of 41%, 27%, and 25% in SK-OV-3, of 61%, 52%, and 39% in MCF-7, and of 49%, 100%, and 23% in MDA-MB-453. In the three cell lines expressing HER2, it was observed that the cytotoxicity due to infection with the dual-targeting HADa-HgH-D virus was the highest. However, since the gDm virus was not targeted to HER2, cytotoxicity was not observed, and MDA-MB-231 not expressing HER2 was not capable of infection, so it was observed that the three viruses were not involved in cytotoxicity. The reason why there was no effect on the viability of MDA-MB-453 cells seems to be that the initial infection with the HADa-S virus was very low compared to the other viruses.

<Example 8> Inhibition of Growth of Tumor Cells Due to HER2 Dual-Targeting Oncolytic Virus in Mice In order to confirm whether the dual-targeting HADa-HgH-D virus manufactured in Example 4 induces inhibition of growth of cancer cells expressing HER2 in mice, the following experiment was conducted.

After subcutaneous injection of SK-OV-3 at $5 \times 10^6$ cells/mouse into 5-week-old Balb/c nude mice (Orient Bio), the tumors were observed until the size thereof became 100 $mm^3$. Intratumoral injection of the HER2 dual-targeting HADa-HgH-D virus at $2 \times 10^7$ pfu/mouse into 5 mice having tumors was performed, and PBS was injected into 5 mice as a control. After virus injection, the size of the tumor generated in mice was observed for 28 days.

Figure 16:
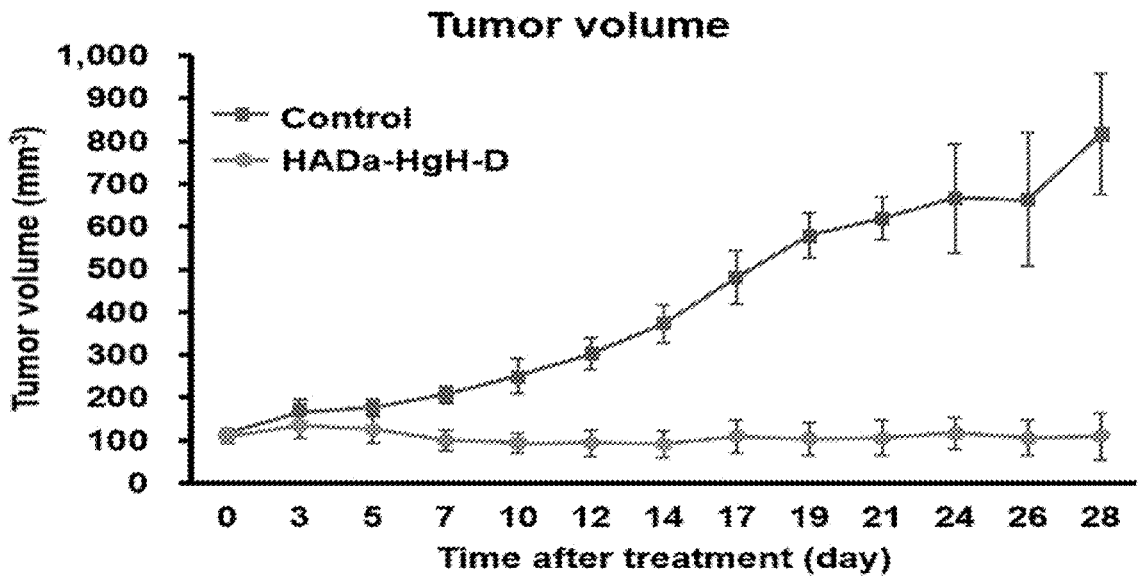
FIG. 16 shows the results of tumor suppression by a dual-targeting virus (HADa-HgH-D) having a HER2scFv ligand in gH and expressing a HER2scFv-HveA adapter in an animal experiment.

The results thereof are shown in a graph of the tumor size for 28 days in FIG. 16. In the control using PBS, the tumor grew to $815.28 \pm 141.36$ $mm^3$ from $116.46 \pm 11.21$ $mm^3$ in the initial stage, but in the mice injected with the HER2 dual-targeting HADa-HgH-D virus, tumor growth was observed from $108.85 \pm 15.54$ $mm^3$ to $110.02 \pm 55.44$ $mm^3$, which was regarded as inhibited compared to the control.

<Example 9> Infection and Cytotoxicity of EpCAM-Expressing Cancer Cells Using EpCAM Dual-Targeting Oncolytic Virus An experiment was performed in cancer cell lines using the EADa-S virus expressing the EpCAMscFv-HveA adapter, the EgH-S virus expressing the EpCAMscFv ligand in gH, and the dual-targeting EADa-EgH-D virus expressing both the EpCAMscFv-HveA adapter and the EpCAMscFv ligand in gH, manufactured in Examples 3 and 5.

In order to confirm whether each virus induces viral infection into surrounding cancer cells due to the EpCAM-scFv ligand expressed in the glycoprotein gH or due to the adapter and whether it induces cytotoxicity after infection, the following experiment was conducted.

The cell lines that were used in the experiment were a cell line not expressing EpCAM (Mia-PaCa-2) and cell lines expressing EpCAM (MCF-7, MDA-MB-453, and BT-474). For breast cancer cell lines MCF-7 (ATCC, HTB-22) and BT-474 (ATCC, HTB-20) and a pancreatic cancer cell line Mia-PaCa-2 (ATCC, CRL-1420), culture was performed using DMEM containing 100 U/ml penicillin/100 μg/ml streptomycin (Welgene) and 10% FBS, and for a breast cancer cell line MDA-MB-453 (ATCC, HTB-131), culture was performed using an RPMI medium containing 100 U/ml penicillin/100 μg/ml streptomycin (Welgene) and 10% FBS.

For an EpCAM-specific viral infection experiment, $4.0 \times 10^4$ MCF-7, $8.0 \times 10^4$ MDA-MB-453, and $7.0 \times 10^4$ BT-474 cell lines were used at 1 MOI and infected with EADa-S expressing the EpCAMscFv-HveA adapter manufactured in Example 3, the EgH-S virus expressing the EpCAMscFv ligand in gH manufactured in Example 4, the dual-targeting EADa-EgH-D virus expressing both the adapter and the ligand, and, as a control, the gDm virus not targeting EpCAM manufactured in Example 2. After 90 minutes, the medium that was used was replaced with a fresh medium in order to remove the remaining initial virus. 2 days after infection, viral infection was confirmed through EmGFP fluorescence expression in each cell line (Baek H. J. et al., Mol. Ther. 2011. 19 (3): 507-514). Also, in order to measure cytotoxicity for 5 days after infection, the extent of color development of formazan, which is a color-developing material formed only in living cells using an EZ-Cytox (DoGenBio) reagent, was measured at 450 nm using an ELISA reader. Absorbance was quantified to determine the cytotoxicity of cancer cell lines due to each virus.

Figure 17:
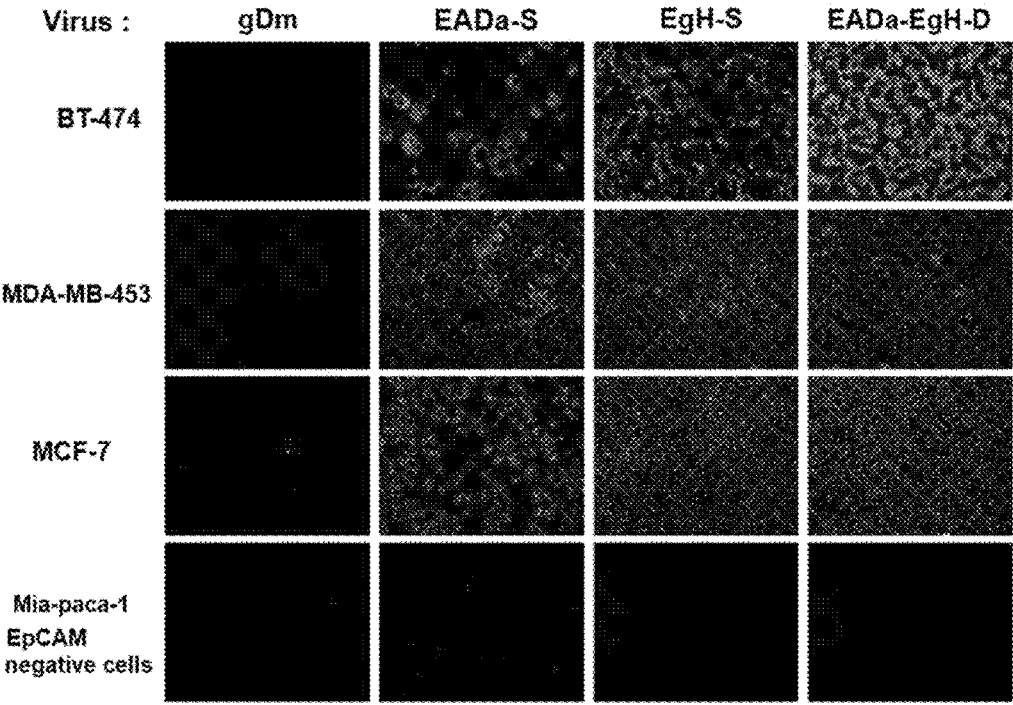
FIG. 17 shows the results of specific infection depending on the expression of EpCAM in BT-474 cells and the like, of a virus (gDm) expressing a fluorescent protein EmGFP and enabling cell entry using only HVEM as a cell receptor, a virus (EADa-S) expressing an EpCAMscFv-HveA adapter, a virus (EgH-S) having an EpCAMscFv ligand in gH, and a dual-targeting virus (EADa-EgH-D) having an EpCAMscFv ligand in gH and expressing an EpCAMscFv-HveA adapter.

The results thereof are shown in FIG. 17. As is apparent from FIG. 17, the infection of BT-474, MDA-MB-453 and MCF7 cells with all of the EADa-S virus expressing only the EpCAM-HveA adapter, the EgH-S virus expressing the EpCAMscFv ligand in gH, and the dual-targeting EADa-EgH-D virus expressing both the adapter and the ligand was observed through fluorescence, and the dual-targeting EADa-EgH-D virus was observed to exhibit a high infection rate compared to the EADa-S and EgH-S viruses. Since the gDm virus was not targeted to EpCAM, it was observed that the cancer cell lines were not infected therewith, and also that there was no viral infection in Mia-PaCa-2 cells not expressing EpCAM.

Figure 18:
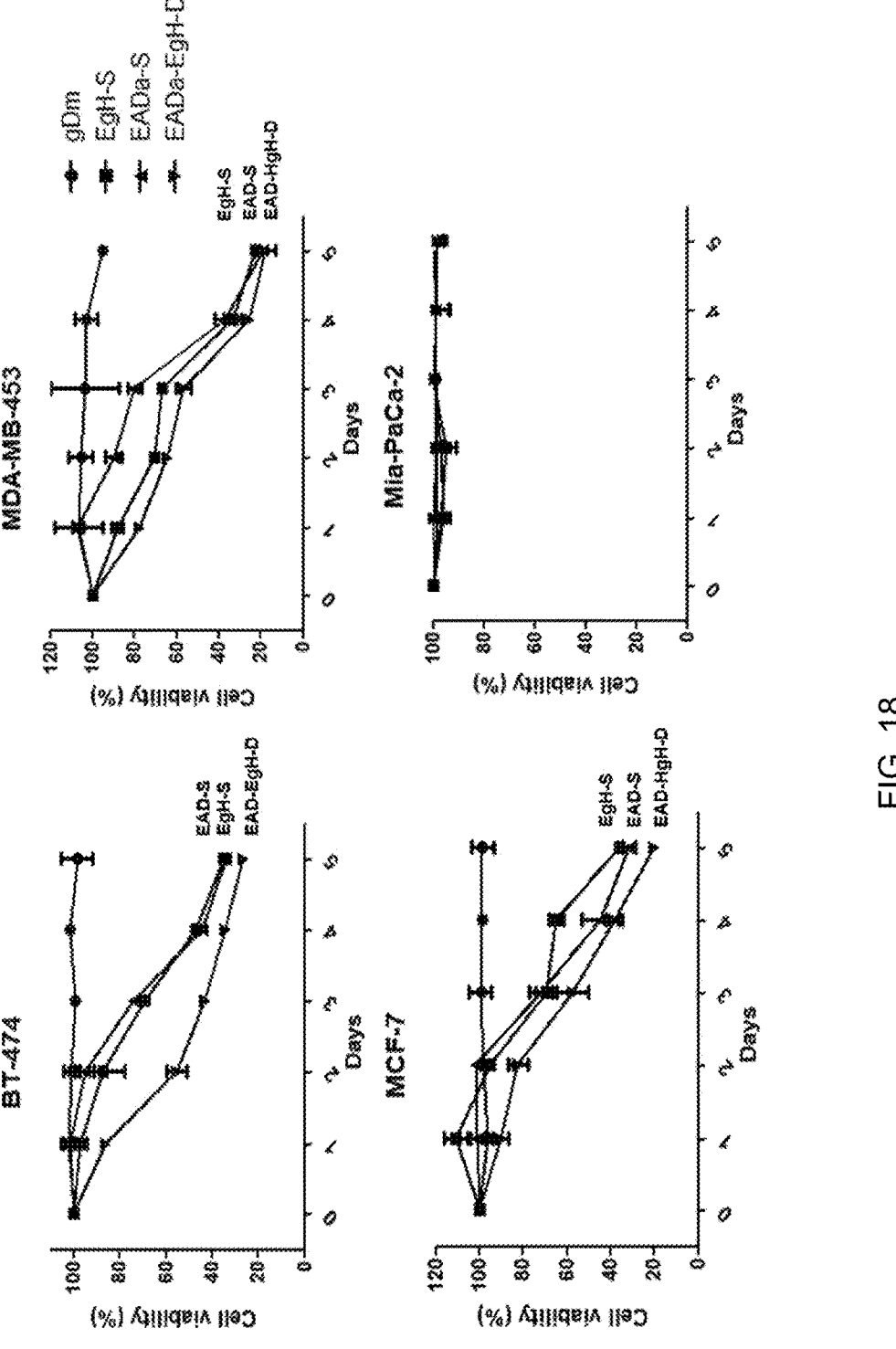
FIG. 18 shows the results of specific cell death depending on the expression of EpCAM in BT-474 cells and the like, of a virus (gDm) expressing a fluorescent protein EmGFP and enabling cell entry using only HVEM as a cell receptor, a virus (EADa-S) expressing an EpCAMscFv-HveA adapter, a virus (EgH-S) having an EpCAMscFv ligand in gH, and a dual-targeting virus (EADa-EgH-D) having an EpCAMscFv ligand in gH and expressing an EpCAMscFv-HveA adapter.

In addition, FIG. 18 shows the results of observation of the cytotoxicity of cancer cells due to the virus for 5 days after infection. The EgH-S, EADa-S, and EADa-EgH-D viruses exhibited respective cell viability values of 35%, 34%, and 26% in BT-474, of 22%, 19%, and 17% in MDA-MB-453, and of 36%, 31%, and 20% in MCF-7. In the three cell lines expressing EpCAM, it was observed that the cytotoxicity due to infection with the EADa-EgH-D dual-targeting virus was the highest. However, since the gDm virus was not targeted to EpCAM, cytotoxicity was not observed, and Mia-PaCa-2 not expressing EpCAM was not infected, so any virus was not involved in cytotoxicity.

<Example 10> Production of HSV-1 Having HER2-Targeting Modified Glycoprotein gH and Expressing EpCAM-Targeting Adapter For the production of HSV capable of dual targeting of two target molecules (HER2/EpCAM) expressed in specific cancer, a ligand (HER2 scFv) that recognizes HER2 specifically expressed in cancer cells was inserted between amino acids 29 and 30 of the amino acid sequence of gH (GenBank Accession No. ASM47773, SEQ ID NO: 3), which is a glycoprotein of the KOS-UL3/4_EpCAMscFv-HveA-EmGFP-gD-R222N/F223I (EADa-S) virus expressing the EpCAMscFv-HveA adapter.

A gene capable of expressing HER2scFv was inserted between amino acids 29 and 30 of the glycoprotein gH in the KOS-37/BAC-UL3/4_EpCAMscFv-HveA-EmGFP-gD/R222N/F223I (EADa-S) DNA manufactured in Example 3.

Figure 19:
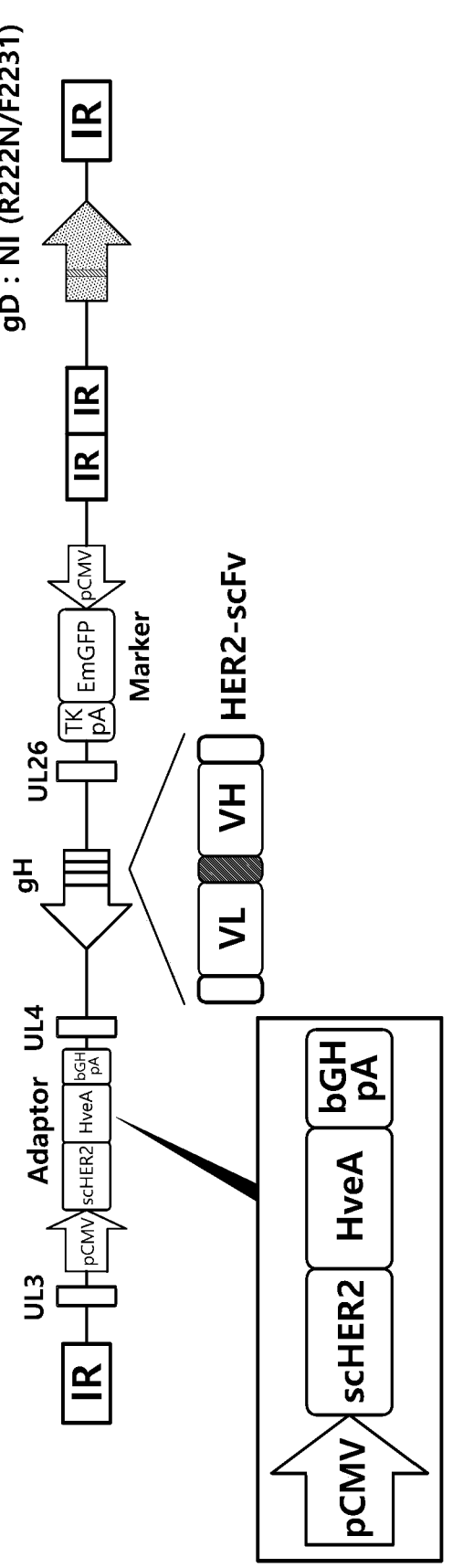
FIG. 19 schematically shows the genomic structure of a dual-targeting HSV-1 virus (EADa-HgH-D) having a HER2-targeting modified glycoprotein gH and expressing an EpCAM-targeting adapter.

The genomic structure of the KOS-UL3/4_EpCAMscFv-HveA-gH/HER2scFv-EmGFP-gD/R222N/F223I virus in which the HER2scFv ligand was inserted into the gH of HSV-1 is shown in FIG. 19, and the entire sequence of the gH-HER2scFv ligand and the construction of the corresponding sequence are shown in FIG. 8. Here, scFv for HER2 is configured such that VH of SEQ ID NO: 4 and VL of SEQ ID NO: 5 are linked via a linker peptide of SEQ ID NO: 24, and the linker peptide of SEQ ID NO: 35 is linked to the N-terminus of this scFv, and the linker peptide of SEQ ID NO: 36 is linked to the C-terminus thereof.

The amino acid sequence and the gene sequence of the full length of HER2scFv used in the present example are represented in SEQ ID NO: 37 and SEQ ID NO: 38, respectively.

Insertion of the gH-HER2scFv ligand was performed according to the manufacturer's protocol using a counter-selection BAC modification kit (GeneBridges Inc.), as in Example 4.

Specifically, the E. coli clone containing the KOS-37/BAC-UL3/4_EpCAMscFv-HveA-EmGFP-gD-R222N/F223I DNA manufactured in Example 3 was transformed with a pRed/ET plasmid expressing RecE and RecT capable of performing the function of homologous recombination (Muyrers J. P. et al.; Nucleic Acids Res. 1999. 27 (6): 1555-1557). A gH29/30-rpsL-neo/kan cassette was manufactured using a set of homologous region primers (forward primer gH29/30-rpsL-neo_for: SEQ ID NO: 39, reverse primer gH29/30-rpsL-neo_rev: SEQ ID NO: 40) including a locus at which to introduce a target gene between amino acids 29 and 30 of gH.

The clone containing KOS-37/BAC-UL3/4_EpCAMscFv-HveA-EmGFP-gD-R222N/F223I DNA and pRed/ET was added with L-arabinose (Sigma-Aldrich) to thus induce homologous recombination, followed by transformation with 200 ng of the gH29/30-rpsL-neo/kan cassette manufactured as described above. Through such homologous recombination, the gH29/30-rpsL-neo/kan cassette is inserted between amino acids 29 and 30 of gH. E. coli into which gH29/30-rpsL-neo/kan is inserted exhibits kanamycin resistance, but streptomycin resistance is blocked by the rpsL gene. It was inferred for E. coli obtained from the kanamycin medium that gH29/30-rpsL-neo/kan was inserted therein, and the final step of inserting a target gene was performed.

E. coli containing the gH29/30-rpsL-neo/kan cassette was added with L-arabinose (Sigma-Aldrich) activating the function of pRed/ET to thus induce homologous recombination, followed by transformation with 200 ng of the gH29/30-HER2scFv ligand. The gH29/30-HER2scFv ligand was manufactured using a forward primer gH29/30-scFv_For (SEQ ID NO: 41) and a reverse primer gH29/30scFv_Rev (SEQ ID NO: 42) using a pCAGGSMCS-gH-HER2scFv plasmid as a template.

Based on the principle whereby streptomycin resistance blocked by rpsL is activated upon replacing the conventionally inserted gH29/30-rpsL-neo/kan cassette with the above inserted gH29/30-HER2scFv, candidates were selected in a streptomycin medium (Heermann R. et al., Microb. Cell Fact. 2008. 14: doi: 10.1186). DNA was isolated from the selected candidates using a DNA preparation method (Horsburgh B. C. et al., Methods Enzymol. 1999. 306:337-352). The introduction of HER2scFv at gH29/30 was confirmed through restriction enzyme EcoRI and XhoI treatment and PCR (polymerase chain reaction), and the exact gene sequence was identified through sequencing of the PCR product.

The completed KOS-37/BAC-gH/HER2scFv-UL3/4_EpCAMscFv-HveA-EmGFP-gD-R222N/F223I DNA was extracted using a large-construct DNA purification kit (Macherey-Nagel), after which 2×10⁵ Cre-Vero-HVEM cells were transfected with 1 μg of DNA using a Lipofectamine 2000 reagent (Invitrogen) to remove the BAC gene using Cre recombinase. 3 days after transfection, the fluorescence expression of the EmGFP protein and the formation of cell plaques were observed using a fluorescence microscope. After confirmation of plaque formation, the virus-containing cells were collected, subjected three times to a freeze-thaw process (Gierasch W. W. et al.; J. Virol. Methods. 2006. 135:197-206), and sonicated, ultimately obtaining a KOS-UL3/4_EpCAMscFv-HveA-gH_HER2scFv-EmGFP-gD-R222N/F223I dual-targeting virus (EADa-HgH-D) expressing the EpCAMscFv-HveA adapter and the HER2scFv ligand in gH.

<Example 11> Experiment of Dual-Targeting Effect of HSV-1 Having HER2-Targeting Modified Glycoprotein gH and Expressing EpCAM-Targeting Adapter In order to confirm induction of infection of cells expressing HER2 and EpCAM proteins with the KOS-UL3/4_EpCAMscFv-HveA-gH/HER2scFv-EmGFP-gD-R222N/F223I dual-targeting virus (EADa-HgH-D) expressing the EpCAMscFv-HveA adapter and the HER2scFv ligand in gH manufactured in Example 10, the following experiment was conducted.

The cell lines that were used in the experiment were a cell line (CHO-K1) not expressing HER2 and EpCAM, a cell line (CHO-HER2) expressing HER2, and a cell line (CHO-EpCAM) expressing EpCAM. The Chinese hamster ovary cell lines CHO-K1, CHO-HER2, and CHO-EpCAM (Kuroki M et al., J. Biol. Chem. 1991. 74:10132-10141) were cultured using a HaM's F-12K medium (Welgene) containing 100 U/ml penicillin/100 μg/ml streptomycin (Welgene) and 10% FBS (fetal bovine serum).

For specific viral infection, 2.5×10⁴ CHO-K1, CHO-HER2, and CHO-EpCAM cell lines were applied on a 96-well plate. After 24 hours, the HER2 dual-targeting virus (HADa-HgH-D) manufactured in Example 4, the EpCAM dual-targeting virus (EADa-EgH-D) manufactured in Example 5, and the HER2/EpCAM dual-targeting virus (EADa-HgH-D) manufactured in Example 10 were used at 5 MOI for infection. After 90 minutes, the medium that was used was replaced with a fresh medium in order to remove the remaining initial virus and adapter. 2 days after infection, viral infection was observed through fluorescence expression in each cell line (Baek H. J. et al., Mol. Ther. 2011. 19 (3): 507-514).

Figure 20:
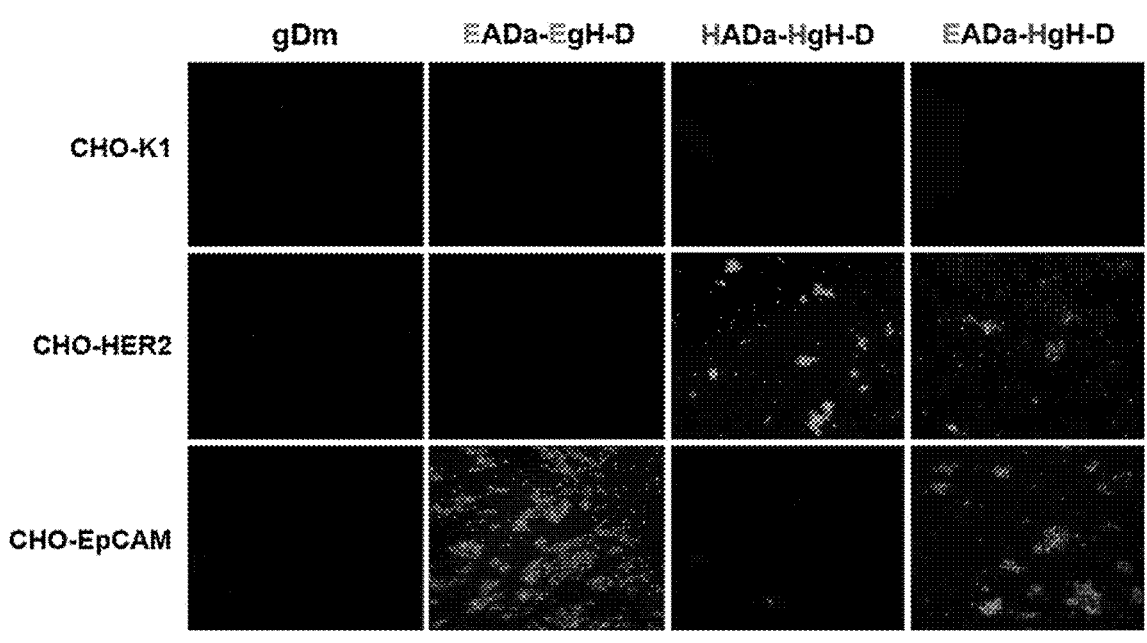
FIG. 20 shows the results of dual targeting depending on the expression of HER2 and EpCAM in CHO-K1 cells and the like, of a dual-targeting HSV-1 virus (EADa-HgH-D) having a HER2-targeting modified glycoprotein gH and expressing an EpCAM-targeting adapter.

The results thereof are shown in FIG. 20. As is apparent from FIG. 20, fluorescence microscope images of the cell lines infected with the viruses are shown. It was observed that no viruses infected the CHO-K1 cell line not expressing HER2 and EpCAM. The HER2 dual-targeting virus (HADa-HgH-D) infected only CHO-HER2, and the EpCAM dual-targeting virus (EADa-EgH-D) infected only CHO-EpCAM. However, it was confirmed that the HER2/EpCAM dual-targeting virus (EADa-HgH-D) infected all of CHO-HER2 and CHO-EpCAM cells. Based on the above results, it was possible to confirm the possibility of a strategy to target at least two target molecules using the virus capable of targeting two target molecules together.

<Example 12> Experiment of Dual-Targeting Effect of HSV-1 Expressing HER2/EpCAM Dual-Targeting Adapter In order to confirm induction of infection of cells expressing HER2 and EpCAM proteins with the HER2 and EpCAM dual-targeting virus (EADa-HADa-D) expressing both the EpCAMscFv-HveA adapter and the HER2scFv-HveA adapter manufactured in Example 3, the following experiment was conducted.

The cell lines that were used in the experiment were a cell line (CHO-K1) not expressing HER2 and EpCAM, a cell line (CHO-HER2) expressing HER2, and a cell line (CHO-EpCAM) expressing EpCAM. The Chinese hamster ovary cell lines CHO-K1, CHO-HER2, and CHO-EpCAM (Kuroki M et al., J. Biol. Chem. 1991. 74:10132-10141) were cultured using a HaM's F-12K medium (Welgene) containing 100 U/ml penicillin/100 μg/ml streptomycin (Welgene) and 10% FBS (fetal bovine serum).

For specific viral infection, 2.5×10⁴ CHO-K1, CHO-HER2, and CHO-EpCAM cell lines were applied on a 96-well plate. After 24 hours, the virus (HADa-S) expressing only the HER2scFv-HveA adapter, the virus (EADa-S) expressing only the EpCAMscFv-HveA adapter, and the dual-targeting virus (EADa-HADa-D) expressing the EpCAMscFv-HveA adapter and the HER2scFv-HveA adapter, manufactured in Example 3, were used at 5 MOI for infection. After 90 minutes, the medium that was used was replaced with a fresh medium in order to remove the remaining initial virus and adapter. 2 days after infection, viral infection was observed through fluorescence expression in each cell line using a fluorescence microscope (Baek H. J. et al., Mol. Ther. 2011. 19 (3): 507-514).

Figure 21:
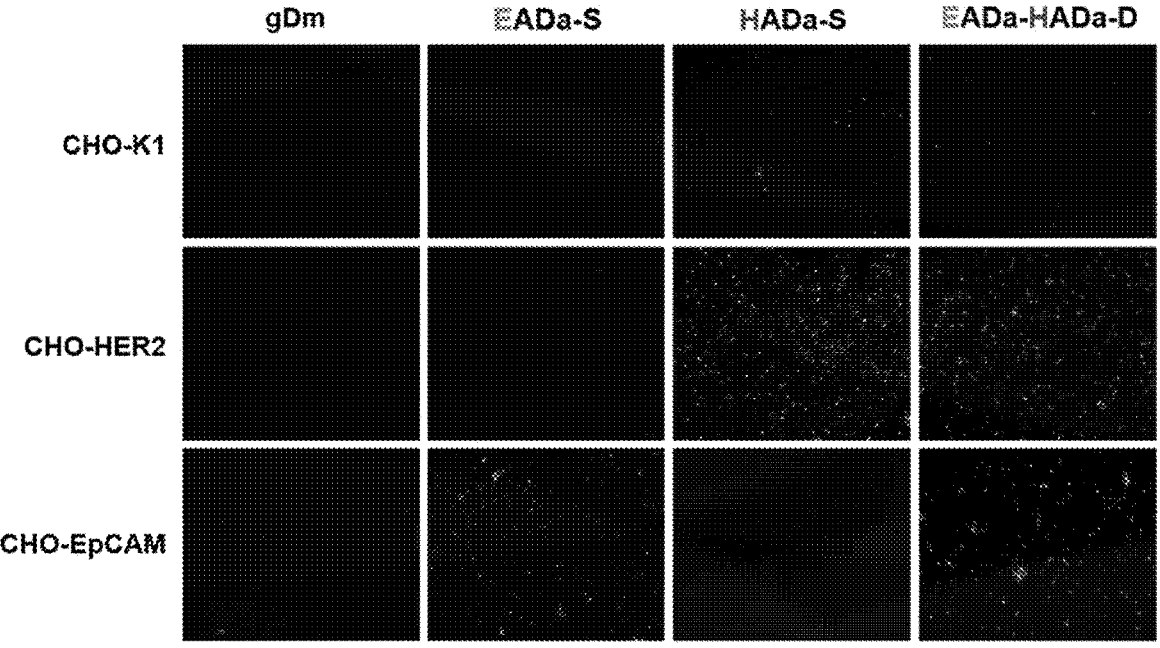
FIG. 21 shows the results of dual targeting depending on the expression of HER2 and EpCAM in CHO-K1 cells and the like, of an HSV-1 virus (EADa-HADa-D) expressing a HER2/EpCAM dual-targeting adapter.

As a result, FIG. 21 shows fluorescence microscope images of the cell lines that were infected with individual viruses. It was observed that no viruses infected the CHO-K1 cell line not expressing HER2 and EpCAM, the virus (HADa-S) expressing only the HER2scFv-HveA adapter infected only CHO-HER2, and the virus (EADa-S) expressing only the EpCAMscFv-HveA adapter infected only CHO-EpCAM. However, it was confirmed that the dual-targeting virus (EADa-HADa-D) expressing both the EpCAMscFv-HveA adapter and the HER2scFv-HveA adapter infected all of CHO-HER2 and CHO-EpCAM cells.

Based on the above results, it was possible to confirm the possibility of a strategy to target at least two target molecules using the virus expressing the adapter capable of targeting two target molecules together.

What is claimed is:

1. A recombinant herpes simplex virus for multiple targeting comprising:

(i) at least two expression cassettes, wherein each expression cassette is capable of expressing an adapter, wherein the adapter is a fused protein comprising a targeting domain that binds to a cancer cell target molecule and an extracellular domain of Herpesvirus Entry Mediator HveA (HVEM) that binds to a glycoprotein gD, and wherein the at least two expression cassettes are inserted into a genome of a herpes simplex virus without inhibiting propagation of the herpes simplex virus;

(ii) a leader sequence attached to the N-terminus of the cancer cell target domain or the extracellular domain of HVEM, wherein the expression cassettes are inserted between UL3 and UL4 genes, between UL26 and UL27 genes, between UL48 and UL49 genes, between UL53 and UL54 genes, or between US1 and US2 genes in the genome of the virus; and (iii) another targeting domain, wherein the another targeting domain binds to a cancer cell target molecule, wherein the another targeting domain is inserted and fused into a position between amino acids 29 and 30 in a glycoprotein gH, wherein the glycoprotein gH has a sequence consisting of SEQ ID NO: 3, and wherein the cancer cell target molecule is an antigen or a receptor on a surface of a cancer cell that is expressed only in a cancer cell or is overexpressed in a cancer cell compared to a normal cell.

2. The recombinant herpes simplex virus of claim 1, wherein the targeting domain of (i) and the another targeting domain of (iii) have (a) targeting domains that bind to an identical target molecule, or (b) different targeting domains that bind to different target molecules.

3. The recombinant herpes simplex virus of claim 1, wherein the extracellular domain of HVEM is HveA82 comprising an amino acid sequence of SEQ ID NO: 8 or 9.

4. The recombinant herpes simplex virus of claim 1, wherein the fused proteins of (i) are fused proteins in which the cancer cell targeting domain and the extracellular domain of HVEM are linked via a linker peptide comprising 1 to 30 amino acids, and the linker peptide comprises at least one amino acid selected from among Ser, Gly, Ala, and Thr.

5. The recombinant herpes simplex virus of claim 1, wherein the antigen or the receptor is HER2 (human epidermal growth factor receptor 2) or EpCAM (epithelial cell adhesion molecule).

6. The recombinant herpes simplex virus of claim 1, wherein the cancer cell target molecule of (i) is HER2, and the targeting domain of (i) is scFv, wherein the targeting domain comprises VH of SEQ ID NO: 4 and VL of SEQ ID NO: 5, wherein the VH and VL are linked in an order of VH, a linker peptide, and VL via the linker peptide.

7. The recombinant herpes simplex virus of claim 1, wherein the cancer cell target molecule of (i) is EpCAM, and the targeting domain of (i) is scFv, wherein the targeting domain comprises VL of SEQ ID NO: 6 and VH of SEQ ID NO: 7, wherein the VL and VH are linked in an order of VL, a linker peptide, and VH via the linker peptide.

8. The recombinant herpes simplex virus of claim 1, wherein the recombinant herpes simplex virus is a recombinant HSV-1 virus, a recombinant HSV-2 virus, or an HSV-1 and HSV-2 chimeric virus.

9. The recombinant herpes simplex virus of claim 1, wherein the recombinant herpes simplex virus is a recombinant HSV-1 derived from an HSV-1 KOS strain.

10. The recombinant herpes simplex virus of claim 1, wherein the recombinant herpes simplex virus further comprises an expression cassette expressing one selected from:

(i) cytokine, (ii) chemokine, (iii) an antagonist to an immune checkpoint, (iv) a co-stimulatory factor, which induces activation of an immune cell, (v) an antagonist to TGFβ, which inhibits an immune response to a cancer cell, (vi) heparanase, which degrades heparan sulfate proteoglycan for a solid tumor microenvironment, (vii) an antagonist, which inhibits a function of an angiogenesis factor receptor VEGFR-2 (VEGF receptor-2), and (viii) a prodrug-activating enzyme, which converts a prodrug into a drug that exhibits toxicity to a cancer cell, wherein the expression cassette is further inserted into the genome of the herpes simplex virus without inhibiting propagation of the herpes simplex virus.

11. The recombinant herpes simplex virus of claim 10, wherein the cytokine is at least one selected from interleukins including IL-2, IL-4, IL-7, IL-10, IL-12, IL-15, IL-18, and IL-24, interferons including IFNα, IFNβ, and IFNγ, tumor necrosis factors including TNFα, GM-CSF, G-CSF, and FLT3L, wherein the chemokine is at least one selected from CCL2, RANTES, CCL7, CCL9, CCL10, CCL12, CCL15, CCL19, CCL21, CCL20, and XCL-1, wherein the immune checkpoint is at least one selected from PD-1 (programmed cell death 1), PD-L1 (programmed cell death ligand 1), PD-L2 (programmed cell death ligand 2), CD27 (cluster of differentiation 27), CD28 (cluster of differentiation 28), CD70 (cluster of differentiation 70), CD80 (cluster of differentiation 80), CD86 (cluster of differentiation 86), CD137 (cluster of differentiation 137), CD276 (cluster of differentiation 276), KIR (killer-cell immunoglobulin-like receptor), LAG3 (lymphocyte activation gene 3), GITR (glucocorticoid-induced TNFR-related protein), GITRL (glucocorticoid-induced TNFR-related protein ligand), and CTLA-4 (cytolytic T lymphocyte associated antigen-4), wherein the co-stimulatory factor is at least one selected from CD2, CD7, LIGHT, NKG2C, CD27, CD28, 4-1BB, OX40, CD30, CD40, LFA-1 (lymphocyte function-associated antigen-1), ICOS (inducible T cell co-stimulator), CD3γ, CD3δ, and CD3ε, and wherein the prodrug-activating enzyme is at least one selected from cytosine deaminase, rat cytochrome P450 (CYP2B1), carboxylesterase, bacterial nitroreductase, and PNP (purine nucleoside phosphorylase) isolated from *E. coli*.

12. The recombinant herpes simplex virus of claim 1, wherein each of the expression cassettes is inserted between UL3 and UL4 genes, between UL26 and UL27 genes, between UL37 and UL38 genes, between UL48 and UL49 genes, between UL53 and UL54 genes, or between US1 and US2 genes in the genome of the virus.

13. The recombinant herpes simplex virus of claim 1, wherein the fused proteins are in an order of NH2/cancercell-targeting domain/extracellular domain of HVEM/ COOH or in a reversed order thereof.

14. The recombinant herpes simplex virus of claim 1, wherein the fused proteins comprise the cancer cell targeting domain and the extracellular domain of HVEM linked via a linker peptide, and the fused proteins are in an order of NH$_2$/cancer-cell-targeting domain/linker peptide/extracellular domain of HVEM/COOH or in a reversed order thereof.

15. The recombinant herpes simplex virus of claim 1, wherein the expression cassettes of (i) have a polycistronic configuration in which the at least two fused protein genes are contained, a nucleic acid sequence encoding an IRES (internal ribosome entry site) or a 2A peptide is located between the genes, and at least one expression cassette is inserted.

16. The recombinant herpes simplex virus of claim 1, wherein the expression cassettes of (i) have a monocistronic configuration in which the at least two expression cassettes are inserted into the genome of the recombinant herpes simplex virus.

17. The recombinant herpes simplex virus of claim 1, wherein the fused proteins have (a) targeting regions that specifically bind to the same target molecule, or (b) different targeting regions that specifically bind different target molecules.

\* \* \* \* \*

```
                              SEQUENCE LISTING

<160> NUMBER OF SEQ ID NOS: 49

<210> SEQ ID NO 1
<211> LENGTH: 904
<212> TYPE: PRT
<213> ORGANISM: Artificial Sequence
<220> FEATURE:
<223> OTHER INFORMATION: gB

<400> SEQUENCE: 1

Met His Gln Gly Ala Pro Ser Trp Gly Arg Arg Trp Phe Val Val Trp
1               5                   10                  15

Ala Leu Leu Gly Leu Thr Leu Gly Val Leu Val Ala Ser Ala Ala Pro
            20                  25                  30

Ser Ser Pro Gly Thr Pro Gly Val Ala Ala Ala Thr Gln Ala Ala Asn
        35                  40                  45

Gly Gly Pro Ala Thr Pro Ala Pro Pro Ala Leu Gly Ala Ala Pro Thr
    50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
        115                 120                 125

Gln Pro Arg Arg Cys Pro Thr Arg Pro Glu Gly Gln Asn Tyr Thr Glu
    130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
```

```
             210                  215                  220

Arg Asp Asp His Glu Thr Asp Met Glu Leu Lys Pro Ala Asn Ala Ala
225                  230                  235                  240

Thr Arg Thr Ser Arg Gly Trp His Thr Thr Asp Leu Lys Tyr Asn Pro
                 245                  250                  255

Ser Arg Val Glu Ala Phe His Arg Tyr Gly Thr Thr Val Asn Cys Ile
                 260                  265                  270

Val Glu Glu Val Asp Ala Arg Ser Val Tyr Pro Tyr Asp Glu Phe Val
                 275                  280                  285

Leu Ala Thr Gly Asp Phe Val Tyr Met Ser Pro Phe Tyr Gly Tyr Arg
                 290                  295                  300

Glu Gly Ser His Thr Glu His Thr Ser Tyr Thr Ala Asp Arg Phe Lys
305                  310                  315                  320

Gln Val Asp Gly Phe Tyr Ala Arg Asp Leu Thr Thr Lys Ala Arg Ala
                 325                  330                  335

Thr Ala Pro Thr Thr Arg Asn Leu Leu Thr Thr Pro Lys Phe Thr Val
                 340                  345                  350

Ala Trp Asp Trp Val Pro Lys Arg Pro Ser Val Cys Thr Met Thr Lys
                 355                  360                  365

Trp Gln Glu Val Asp Glu Met Leu Arg Ser Glu Tyr Gly Gly Ser Phe
                 370                  375                  380

Arg Phe Ser Ser Asp Ala Ile Ser Thr Thr Phe Thr Thr Asn Leu Thr
385                  390                  395                  400

Glu Tyr Pro Leu Ser Arg Val Asp Leu Gly Asp Cys Ile Gly Lys Asp
                 405                  410                  415

Ala Arg Asp Ala Met Asp Arg Ile Phe Ala Arg Arg Tyr Asn Ala Thr
                 420                  425                  430

His Ile Lys Val Gly Gln Pro Gln Tyr Tyr Leu Ala Asn Gly Gly Phe
                 435                  440                  445

Leu Ile Ala Tyr Gln Pro Leu Leu Ser Asn Thr Leu Ala Glu Leu Tyr
                 450                  455                  460

Val Arg Glu His Leu Arg Glu Gln Ser Arg Lys Pro Pro Asn Pro Thr
465                  470                  475                  480

Pro Pro Pro Pro Gly Ala Ser Ala Asn Ala Ser Val Glu Arg Ile Lys
                 485                  490                  495

Thr Thr Ser Ser Ile Glu Phe Ala Arg Leu Gln Phe Thr Tyr Asn His
                 500                  505                  510

Ile Gln Arg His Val Asn Asp Met Leu Gly Arg Val Ala Ile Ala Trp
                 515                  520                  525

Cys Glu Leu Gln Asn His Glu Leu Thr Leu Trp Asn Glu Ala Arg Lys
                 530                  535                  540

Leu Asn Pro Asn Ala Ile Ala Ser Val Thr Val Gly Arg Arg Val Ser
545                  550                  555                  560

Ala Arg Met Leu Gly Asp Val Met Ala Val Ser Thr Cys Val Pro Val
                 565                  570                  575

Ala Ala Asp Asn Val Ile Val Gln Asn Ser Met Arg Ile Ser Ser Arg
                 580                  585                  590

Pro Gly Ala Cys Tyr Ser Arg Pro Leu Val Ser Phe Arg Tyr Glu Asp
                 595                  600                  605

Gln Gly Pro Leu Val Glu Gly Gln Leu Gly Glu Asn Asn Glu Leu Arg
                 610                  615                  620

Leu Thr Arg Asp Ala Ile Glu Pro Cys Thr Val Gly His Arg Arg Tyr
625                  630                  635                  640
```

```
Phe Thr Phe Gly Gly Gly Tyr Val Tyr Phe Glu Glu Tyr Ala Tyr Ser
            645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
            675                 680                 685

Tyr Thr Arg His Glu Ile Lys Asp Ser Gly Leu Leu Asp Tyr Thr Glu
            690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
            725                 730                 735

Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
            755                 760                 765

Ser Phe Met Ser Asn Pro Phe Gly Ala Leu Ala Val Gly Leu Leu Val
            770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
            805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
            835                 840                 845

Tyr Met Ala Leu Val Ser Ala Met Glu Arg Thr Glu His Lys Ala Lys
            850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
            885                 890                 895

Gly Asp Ala Asp Glu Asp Asp Leu
            900
```

<210> SEQ ID NO 2
<211> LENGTH: 511
<212> TYPE: PRT
<213> ORGANISM: Artificial Sequence
<220> FEATURE:
<223> OTHER INFORMATION: gC

<400> SEQUENCE: 2

```
Met Ala Pro Gly Arg Val Gly Leu Ala Val Val Leu Trp Ser Leu Leu
1               5                   10                  15

Trp Leu Gly Ala Gly Val Ala Gly Gly Ser Glu Thr Ala Ser Thr Gly
            20                  25                  30

Pro Thr Ile Thr Ala Gly Ala Val Thr Asn Ala Ser Glu Ala Pro Thr
            35                  40                  45

Ser Gly Ser Pro Gly Ser Ala Ala Ser Pro Glu Val Thr Pro Thr Ser
            50                  55                  60

Thr Pro Asn Pro Asn Asn Val Thr Gln Asn Lys Thr Thr Pro Thr Glu
65                  70                  75                  80

Pro Ala Ser Pro Pro Thr Thr Pro Lys Pro Thr Ser Thr Pro Lys Ser
            85                  90                  95
```

-continued

```
Pro Pro Thr Ser Thr Pro Asp Pro Lys Pro Lys Asn Asn Thr Thr Pro
            100             105             110

Ala Lys Ser Gly Arg Pro Thr Lys Pro Pro Gly Pro Val Trp Cys Asp
            115             120             125

Arg Arg Asp Pro Leu Ala Arg Tyr Gly Ser Arg Val Gln Ile Arg Cys
    130             135             140

Arg Phe Arg Asn Ser Thr Arg Met Glu Phe Arg Leu Gln Ile Trp Arg
145             150             155             160

Tyr Ser Met Gly Pro Ser Pro Ile Ala Pro Ala Pro Asp Leu Glu
            165             170             175

Glu Val Leu Thr Asn Ile Thr Ala Pro Pro Gly Gly Leu Leu Val Tyr
            180             185             190

Asp Ser Ala Pro Asn Leu Thr Asp Pro His Val Leu Trp Ala Glu Gly
            195             200             205

Ala Gly Pro Gly Ala Asp Pro Pro Leu Tyr Ser Val Thr Gly Pro Leu
    210             215             220

Pro Thr Gln Arg Leu Ile Ile Gly Glu Val Thr Pro Ala Thr Gln Gly
225             230             235             240

Met Tyr Tyr Leu Ala Trp Gly Arg Met Asp Ser Pro His Glu Tyr Gly
            245             250             255

Thr Trp Val Arg Val Arg Met Phe Arg Pro Pro Ser Leu Thr Leu Gln
            260             265             270

Pro His Ala Val Met Glu Gly Gln Pro Phe Lys Ala Thr Cys Thr Ala
            275             280             285

Ala Ala Tyr Tyr Pro Arg Asn Pro Val Glu Phe Val Trp Phe Glu Asp
    290             295             300

Asp Arg Gln Val Phe Asn Pro Gly Gln Ile Asp Thr Gln Thr His Glu
305             310             315             320

His Pro Asp Gly Phe Thr Thr Val Ser Thr Val Thr Ser Glu Ala Val
            325             330             335

Gly Gly Gln Val Pro Pro Arg Thr Phe Thr Cys Gln Met Thr Trp His
            340             345             350

Arg Asp Ser Val Met Phe Ser Arg Arg Asn Ala Thr Gly Leu Ala Leu
    355             360             365

Val Leu Pro Arg Pro Thr Ile Thr Met Glu Phe Gly Val Arg His Val
    370             375             380

Val Cys Thr Ala Gly Cys Val Pro Glu Gly Val Thr Phe Ala Trp Phe
385             390             395             400

Leu Gly Asp Asp Pro Ser Pro Ala Ala Lys Ser Ala Val Thr Ala Gln
            405             410             415

Glu Ser Cys Asp His Pro Gly Leu Ala Thr Val Arg Ser Thr Leu Pro
            420             425             430

Ile Ser Tyr Asp Tyr Ser Glu Tyr Ile Cys Arg Leu Thr Gly Tyr Pro
            435             440             445

Ala Gly Ile Pro Val Leu Glu His His Gly Ser His Gln Pro Pro Pro
    450             455             460

Arg Asp Pro Thr Glu Arg Gln Val Ile Glu Ala Ile Glu Trp Val Gly
465             470             475             480

Ile Gly Ile Gly Val Leu Ala Ala Gly Val Leu Val Val Thr Ala Ile
            485             490             495

Val Tyr Val Val Arg Thr Ser Gln Ser Arg Gln Arg His Arg Arg
            500             505             510
```

<210> SEQ ID NO 3
<211> LENGTH: 838
<212> TYPE: PRT
<213> ORGANISM: Artificial Sequence
<220> FEATURE:
<223> OTHER INFORMATION: gH

<400> SEQUENCE: 3

```
Met Gly Asn Gly Leu Trp Phe Val Gly Val Ile Leu Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
            35                  40                  45

Arg Leu Trp Leu Pro Asn Thr Pro Asp Pro Gln Lys Pro Pro Arg Gly
        50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Ser Lys Thr
                100                 105                 110

Tyr Leu Leu Gly Arg Pro Pro Asn Ala Ser Leu Pro Ala Pro Ile Thr
            115                 120                 125

Val Glu Pro Thr Ala Gln Pro Pro Ala Val Ala Pro Leu Lys Gly
            130                 135                 140

Leu Leu His Asn Pro Thr Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
                180                 185                 190

Pro Pro Pro Arg Pro Pro Val Gly Ala Arg Arg His Pro Thr Thr Glu
            195                 200                 205

Leu Asp Ile Thr His Leu His Asn Ala Ser Thr Thr Trp Leu Ala Thr
            210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
                260                 265                 270

Gly Leu Val Ile Ser Met His Asp Ser Pro Pro Val Glu Val Met Val
            275                 280                 285

Val Pro Ala Gly Gln Thr Leu Asp Arg Val Gly Asp Pro Ala Asp Glu
            290                 295                 300

Asn Pro Pro Gly Ala Leu Pro Gly Pro Pro Gly Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
            355                 360                 365
```

-continued

```
Gly Ala Glu Gln Gly Pro Arg Pro Pro Leu Phe Trp Arg Leu Thr Gly
    370             375             380

Leu Leu Ala Thr Ser Gly Phe Ala Phe Val Asn Ala Ala His Ala Asn
385             390             395             400

Gly Ala Val Cys Leu Ser Asp Leu Leu Gly Phe Leu Ala His Ser Arg
            405             410             415

Ala Leu Ala Gly Leu Ala Ala Arg Gly Ala Ala Gly Cys Ala Ala Asp
            420             425             430

Ser Val Phe Phe Asn Val Ser Val Leu Asp Pro Thr Ala Arg Leu Gln
        435             440             445

Leu Glu Ala Arg Leu Gln His Leu Val Ala Glu Ile Leu Glu Arg Glu
    450             455             460

Gln Ser Leu Ala Leu His Ala Leu Gly Tyr Gln Leu Ala Phe Val Leu
465             470             475             480

Asp Ser Pro Ser Ala Tyr Asp Ala Val Ala Pro Ser Ala Ala His Leu
            485             490             495

Ile Asp Ala Leu Tyr Ala Glu Phe Leu Gly Gly Arg Val Leu Thr Thr
            500             505             510

Pro Val Val His Arg Ala Leu Phe Tyr Ala Ser Ala Val Leu Arg Gln
        515             520             525

Pro Phe Leu Ala Gly Val Pro Ser Ala Val Gln Arg Glu Arg Ala Arg
    530             535             540

Arg Ser Leu Leu Ile Ala Ser Ala Leu Cys Thr Ser Asp Val Ala Ala
545             550             555             560

Ala Thr Asn Ala Asp Leu Arg Thr Ala Leu Ala Arg Ala Asp His Gln
            565             570             575

Lys Thr Leu Phe Trp Leu Pro Asp His Phe Ser Pro Cys Ala Ala Ser
            580             585             590

Leu Arg Phe Asp Leu Asp Glu Ser Val Phe Ile Leu Asp Ala Leu Ala
        595             600             605

Gln Ala Thr Arg Ser Glu Thr Pro Val Glu Val Leu Ala Gln Gln Thr
    610             615             620

His Gly Leu Ala Ser Thr Leu Thr Arg Trp Ala His Tyr Asn Ala Leu
625             630             635             640

Ile Arg Ala Phe Val Pro Glu Ala Ser His Arg Cys Gly Gly Gln Ser
            645             650             655

Ala Asn Val Glu Pro Arg Ile Leu Val Pro Ile Thr His Asn Ala Ser
            660             665             670

Tyr Val Val Thr His Ser Pro Leu Pro Arg Gly Ile Gly Tyr Lys Leu
        675             680             685

Thr Gly Val Asp Val Arg Arg Pro Leu Phe Leu Thr Tyr Leu Thr Ala
    690             695             700

Thr Cys Glu Gly Ser Thr Arg Asp Ile Glu Ser Lys Arg Leu Val Arg
705             710             715             720

Thr Gln Asn Gln Arg Asp Leu Gly Leu Val Gly Ala Val Phe Met Arg
            725             730             735

Tyr Thr Pro Ala Gly Glu Val Met Ser Val Leu Leu Val Asp Thr Asp
            740             745             750

Asn Thr Gln Gln Gln Ile Ala Ala Gly Pro Thr Glu Gly Ala Pro Ser
        755             760             765

Val Phe Ser Ser Asp Val Pro Ser Thr Ala Leu Leu Leu Phe Pro Asn
    770             775             780

Gly Thr Val Ile His Leu Leu Ala Phe Asp Thr Gln Pro Val Ala Ala
```

-continued

```
785                790                795                800

Ile Ala Pro Gly Phe Leu Ala Ala Ser Ala Leu Gly Val Val Met Ile
                805                810                815

Thr Ala Ala Leu Ala Gly Ile Leu Lys Val Leu Arg Thr Ser Val Pro
                820                825                830

Phe Phe Trp Arg Arg Glu
        835

<210> SEQ ID NO 4
<211> LENGTH: 120
<212> TYPE: PRT
<213> ORGANISM: Artificial Sequence
<220> FEATURE:
<223> OTHER INFORMATION: HER2 VH

<400> SEQUENCE: 4

Glu Val Gln Leu Val Glu Ser Gly Gly Gly Leu Val Gln Pro Gly Gly
1                5                10                15

Ser Leu Arg Leu Ser Cys Ala Ala Ser Gly Phe Asn Ile Lys Asp Thr
                20                25                30

Tyr Ile His Trp Val Arg Gln Ala Pro Gly Lys Gly Leu Glu Trp Val
        35                40                45

Ala Arg Ile Tyr Pro Thr Asn Gly Tyr Thr Arg Tyr Ala Asp Ser Val
    50                55                60

Lys Gly Arg Phe Thr Ile Ser Ala Asp Thr Ser Lys Asn Thr Ala Tyr
65                70                75                80

Leu Gln Met Asn Ser Leu Arg Ala Glu Asp Thr Ala Val Tyr Tyr Cys
                85                90                95

Ser Arg Trp Gly Gly Asp Gly Phe Tyr Ala Met Asp Tyr Trp Gly Gln
            100                105                110

Gly Thr Leu Val Thr Val Ser Ser
        115                120

<210> SEQ ID NO 5
<211> LENGTH: 107
<212> TYPE: PRT
<213> ORGANISM: Artificial Sequence
<220> FEATURE:
<223> OTHER INFORMATION: HER2 VL

<400> SEQUENCE: 5

Asp Ile Gln Met Thr Gln Ser Pro Ser Ser Leu Ser Ala Ser Val Gly
1                5                10                15

Asp Arg Val Thr Ile Thr Cys Arg Ala Ser Gln Asp Val Asn Thr Ala
                20                25                30

Val Ala Trp Tyr Gln Gln Lys Pro Gly Lys Ala Pro Lys Leu Leu Ile
        35                40                45

Tyr Ser Ala Ser Phe Leu Tyr Ser Gly Val Pro Ser Arg Phe Ser Gly
    50                55                60

Ser Arg Ser Gly Thr Asp Phe Thr Leu Thr Ile Ser Ser Leu Gln Pro
65                70                75                80

Glu Asp Phe Ala Thr Tyr Tyr Cys Gln Gln His Tyr Thr Thr Pro Pro
                85                90                95

Thr Phe Gly Gln Gly Thr Lys Val Glu Ile Lys
            100                105

<210> SEQ ID NO 6
<211> LENGTH: 113
```

```
<212> TYPE: PRT
<213> ORGANISM: Artificial Sequence
<220> FEATURE:
<223> OTHER INFORMATION: EpCAM VL

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg

<210> SEQ ID NO 7
<211> LENGTH: 114
<212> TYPE: PRT
<213> ORGANISM: Artificial Sequence
<220> FEATURE:
<223> OTHER INFORMATION: EpCAM VH

<400> SEQUENCE: 7

Gln Leu Val Gln Ser Gly Pro Gly Leu Val Gln Pro Gly Gly Ser Val
1               5                   10                  15

Arg Ile Ser Cys Ala Ala Ser Gly Tyr Thr Phe Thr Asn Tyr Gly Met
            20                  25                  30

Asn Trp Val Lys Gln Ala Pro Gly Lys Gly Leu Glu Trp Met Gly Trp
        35                  40                  45

Ile Asn Thr Tyr Thr Gly Glu Ser Thr Tyr Ala Asp Ser Phe Lys Gly
    50                  55                  60

Arg Phe Thr Phe Ser Leu Asp Thr Ser Ala Ser Ala Ala Tyr Leu Gln
65                  70                  75                  80

Ile Asn Ser Leu Arg Ala Glu Asp Thr Ala Val Tyr Tyr Cys Ala Arg
                85                  90                  95

Phe Ala Ile Lys Gly Asp Tyr Trp Gly Gln Gly Thr Leu Leu Thr Val
            100                 105                 110

Ser Ser

<210> SEQ ID NO 8
<211> LENGTH: 82
<212> TYPE: PRT
<213> ORGANISM: Artificial Sequence
<220> FEATURE:
<223> OTHER INFORMATION: HveA 82

<400> SEQUENCE: 8

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30
```

-continued

```
Thr Gly Thr Val Cys Glu Pro Cys Pro Pro Gly Thr Tyr Ile Ala His
        35              40              45

Leu Asn Gly Leu Ser Lys Cys Leu Gln Cys Gln Met Cys Asp Pro Ala
    50              55              60

Met Gly Leu Arg Ala Ser Arg Asn Cys Ser Arg Thr Glu Asn Ala Val
65              70              75              80

Cys Gly

<210> SEQ ID NO 9
<211> LENGTH: 120
<212> TYPE: PRT
<213> ORGANISM: Artificial Sequence
<220> FEATURE:
<223> OTHER INFORMATION: leader sequence _ HveA82

<400> SEQUENCE: 9

Met Glu Pro Pro Gly Asp Trp Gly Pro Pro Pro Trp Arg Ser Thr Pro
1               5               10              15

Arg Thr Asp Val Leu Arg Leu Val Leu Tyr Leu Thr Phe Leu Gly Ala
            20              25              30

Pro Cys Tyr Ala Pro Ala Leu Pro Ser Cys Lys Glu Asp Glu Tyr Pro
        35              40              45

Val Gly Ser Glu Cys Cys Pro Lys Cys Ser Pro Gly Tyr Arg Val Lys
    50              55              60

Glu Ala Cys Gly Glu Leu Thr Gly Thr Val Cys Glu Pro Cys Pro Pro
65              70              75              80

Gly Thr Tyr Ile Ala His Leu Asn Gly Leu Ser Lys Cys Leu Gln Cys
                85              90              95

Gln Met Cys Asp Pro Ala Met Gly Leu Arg Ala Ser Arg Asn Cys Ser
            100             105             110

Arg Thr Glu Asn Ala Val Cys Gly
        115             120

<210> SEQ ID NO 10
<211> LENGTH: 87
<212> TYPE: PRT
<213> ORGANISM: Artificial Sequence
<220> FEATURE:
<223> OTHER INFORMATION: HveA 87

<400> SEQUENCE: 10

Leu Pro Ser Cys Lys Glu Asp Glu Tyr Pro Val Gly Ser Glu Cys Cys
1               5               10              15

Pro Lys Cys Ser Pro Gly Tyr Arg Val Lys Glu Ala Cys Gly Glu Leu
            20              25              30

Thr Gly Thr Val Cys Glu Pro Cys Pro Pro Gly Thr Tyr Ile Ala His
        35              40              45

Leu Asn Gly Leu Ser Lys Cys Leu Gln Cys Gln Met Cys Asp Pro Ala
    50              55              60

Met Gly Leu Arg Ala Ser Arg Asn Cys Ser Arg Thr Glu Asn Ala Val
65              70              75              80

Cys Gly Cys Ser Pro Gly His
            85

<210> SEQ ID NO 11
<211> LENGTH: 125
<212> TYPE: PRT
<213> ORGANISM: Artificial Sequence
<220> FEATURE:
```

<223> OTHER INFORMATION: leader sequence - HveA 87

<400> SEQUENCE: 11

```
Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His
            115                 120                 125
```

<210> SEQ ID NO 12
<211> LENGTH: 102
<212> TYPE: PRT
<213> ORGANISM: Artificial Sequence
<220> FEATURE:
<223> OTHER INFORMATION: HveA 102

<400> SEQUENCE: 12

```
Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala
                100
```

<210> SEQ ID NO 13
<211> LENGTH: 140
<212> TYPE: PRT
<213> ORGANISM: Artificial Sequence
<220> FEATURE:
<223> OTHER INFORMATION: leader sequence - HveA 102

<400> SEQUENCE: 13

```
Met Glu Pro Pro Gly Asp Trp Gly Pro Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
```

```
         50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala
    130                 135                 140

<210> SEQ ID NO 14
<211> LENGTH: 107
<212> TYPE: PRT
<213> ORGANISM: Artificial Sequence
<220> FEATURE:
<223> OTHER INFORMATION: HveA 107

<400> SEQUENCE: 14

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser
            100                 105

<210> SEQ ID NO 15
<211> LENGTH: 145
<212> TYPE: PRT
<213> ORGANISM: Artificial Sequence
<220> FEATURE:
<223> OTHER INFORMATION: leader sequence - HveA 107

<400> SEQUENCE: 15

Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110
```

```
Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser
145

<210> SEQ ID NO 16
<211> LENGTH: 369
<212> TYPE: PRT
<213> ORGANISM: Artificial Sequence
<220> FEATURE:
<223> OTHER INFORMATION: gD (ASM47818)

<400> SEQUENCE: 16

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
        130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
            195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
            275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320
```

-continued

```
Ala Val Gly Gly Ser Leu Leu Ala Ala Leu Val Ile Cys Gly Ile Val
                325                 330                 335

Tyr Trp Met His Arg Arg Thr Arg Lys Ala Pro Lys Arg Ile Arg Leu
            340                 345                 350

Pro His Ile Arg Glu Asp Asp Gln Pro Ser Ser His Gln Pro Leu Phe
        355                 360                 365

Tyr

<210> SEQ ID NO 17
<211> LENGTH: 60
<212> TYPE: DNA
<213> ORGANISM: Artificial Sequence
<220> FEATURE:
<223> OTHER INFORMATION: gD-rpsL For

<400> SEQUENCE: 17
cccaggccta ccagcagggg gtgacggtgg acagcatcgg gatgctgccc ggcctggtga    60

<210> SEQ ID NO 18
<211> LENGTH: 88
<212> TYPE: DNA
<213> ORGANISM: Artificial Sequence
<220> FEATURE:
<223> OTHER INFORMATION: gD-rpsL Rev

<400> SEQUENCE: 18
ccggcgatct tcaagctgta tacggcgacg gtgcgctggt tctcggggat tcagaagaac    60
tcgtcaagaa ggcgtgatgg cgggatcg                                      88

<210> SEQ ID NO 19
<211> LENGTH: 106
<212> TYPE: DNA
<213> ORGANISM: Artificial Sequence
<220> FEATURE:
<223> OTHER INFORMATION: gD R222N_F223I_mutant

<400> SEQUENCE: 19
cccaggccta ccagcagggg gtgacggtgg acagcatcgg gatgctgccc aatatcatcc    60
ccgagaacca gcgcaccgtc gccgtataca gcttgaagat cgccgg                  106

<210> SEQ ID NO 20
<211> LENGTH: 74
<212> TYPE: DNA
<213> ORGANISM: Artificial Sequence
<220> FEATURE:
<223> OTHER INFORMATION: UL26/27-rpsL_For

<400> SEQUENCE: 20
gcgtgggggg gaggaaatcg gcactgacca aggggggtccg ttttgtcacg tcagaagaac   60
tcgtcaagaa ggcg                                                     74

<210> SEQ ID NO 21
<211> LENGTH: 74
<212> TYPE: DNA
<213> ORGANISM: Artificial Sequence
<220> FEATURE:
<223> OTHER INFORMATION: UL26/27-rpsL_Rev

<400> SEQUENCE: 21
aacacataaa ctcccccggg tgtccgcggc ctgtttcctc tttcctttcc ggcctggtga    60
tgatggcggg atcg                                                     74
```

<210> SEQ ID NO 22
<211> LENGTH: 74
<212> TYPE: DNA
<213> ORGANISM: Artificial Sequence
<220> FEATURE:
<223> OTHER INFORMATION: UL26/27-tkpA_For

<400> SEQUENCE: 22
gcgtgggggg gaggaaatcg gcactgacca agggggtccg ttttgtcacg gcctcagaag      60
ccatagagcc cacc                                                       74

<210> SEQ ID NO 23
<211> LENGTH: 74
<212> TYPE: DNA
<213> ORGANISM: Artificial Sequence
<220> FEATURE:
<223> OTHER INFORMATION: UL26/27-pCMV_Rev

<400> SEQUENCE: 23
aacacataaa ctcccccggg tgtccgcggc ctgtttcctc tttcctttcc tatacgcgtt      60
gacattgatt attg                                                       74

<210> SEQ ID NO 24
<211> LENGTH: 15
<212> TYPE: PRT
<213> ORGANISM: Artificial Sequence
<220> FEATURE:
<223> OTHER INFORMATION: HER2 Linker

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 27
<212> TYPE: PRT
<213> ORGANISM: Artificial Sequence
<220> FEATURE:
<223> OTHER INFORMATION: EpCAM Linker

<400> SEQUENCE: 25

Ala Thr Pro Ser His Asn Ser His Gln Val Pro Ser Ala Gly Gly Pro
1               5                   10                  15

Thr Ala Asn Ser Gly Thr Ser Gly Ser Glu Val
            20                  25

<210> SEQ ID NO 26
<211> LENGTH: 20
<212> TYPE: PRT
<213> ORGANISM: Artificial Sequence
<220> FEATURE:
<223> OTHER INFORMATION: scFv leader sequence

<400> SEQUENCE: 26

Met Ser Val Pro Thr Gln Val Leu Gly Leu Leu Leu Leu Trp Leu Thr
1               5                   10                  15

Gly Ala Arg Cys
            20

<210> SEQ ID NO 27
<211> LENGTH: 351
<212> TYPE: PRT
<213> ORGANISM: Artificial Sequence
<220> FEATURE:

-continued

```
<223> OTHER INFORMATION: Whole sequence _ HER2scFv-HveA adapter

<400> SEQUENCE: 27

Met Ser Val Pro Thr Gln Val Leu Gly Leu Leu Leu Leu Trp Leu Thr
1               5                   10                  15

Gly Ala Arg Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
            115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Val Asn Thr Ala Val Ala Trp Tyr Gln
            180                 185                 190

Gln Lys Pro Gly Lys Ala Pro Lys Leu Leu Ile Tyr Ser Ala Ser Phe
            195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln His Tyr Thr Thr Pro Pro Thr Phe Gly Gln Gly
            245                 250                 255

Thr Lys Val Glu Ile Lys Gly Gly Gly Ser Glu Phe Leu Pro Ser
            260                 265                 270

Cys Lys Glu Asp Glu Tyr Pro Val Gly Ser Glu Cys Cys Pro Lys Cys
            275                 280                 285

Ser Pro Gly Tyr Arg Val Lys Glu Ala Cys Gly Glu Leu Thr Gly Thr
    290                 295                 300

Val Cys Glu Pro Cys Pro Pro Gly Thr Tyr Ile Ala His Leu Asn Gly
305                 310                 315                 320

Leu Ser Lys Cys Leu Gln Cys Gln Met Cys Asp Pro Ala Met Gly Leu
            325                 330                 335

Arg Ala Ser Arg Asn Cys Ser Arg Thr Glu Asn Ala Val Cys Gly
            340                 345                 350

<210> SEQ ID NO 28
<211> LENGTH: 1053
<212> TYPE: DNA
<213> ORGANISM: Artificial Sequence
<220> FEATURE:
<223> OTHER INFORMATION: Whole sequence _ HER2scFv-HveA adapter

<400> SEQUENCE: 28
```

-continued

```
atgagtgtgc ccactcaggt cctggggttg ctgctgctgt ggcttacagg tgccagatgt          60
gaggtgcagc tggttgaatc tggcggagga ctggttcagc ctggcggatc tctgagactg         120
tcttgtgccg ccagcggctt caacatcaag gacacctaca tccactgggt ccgacaggcc         180
cctggcaaag acttgaatg gtcgccaga atctacccca ccaacggcta caccagatac          240
gccgactctg tgaagggcag attcaccatc agcgccgaca ccagcaagaa caccgcctac         300
ctgcagatga acagcctgag agccgaggac accgccgtgt actactgttc tagatgggga         360
ggcgacggct tctacgccat ggattattgg ggccagggca ccctggtcac agtttctagc         420
ggaggcggag gttctggcgg cggaggaagt ggtggcggag gctctgatat ccagatgaca         480
cagagcccca gcagcctgtc tgcctctgtg ggagacagag tgaccatcac ctgtagagcc         540
agccaggacg tgaacacagc cgtggcttgg tatcagcaga gcctggcaa ggcccctaag          600 ctgctgatct acagcgccag ctttctgtac agcggcgtgc ccagcagatt cagcggctct         660
agaagcggca ccgacttcac cctgaccata agcagtctgc agcccgagga cttcgccacc         720
tactactgtc agcagcacta caccacacct ccaaccttcg acagggcac caaggtggaa          780 atcaagggtg gtggcggttc agaattcctg ccgtcctgca aggaggacga gtacccagtg         840
ggctccgagt gctgccccaa gtgcagtcca ggttatcgtg tgaaggaggc ctgcggggag         900
ctgacgggca cagtgtgtga accctgccct ccaggcacct acattgccca cctcaatggc         960
ctaagcaagt gtctgcagtg ccaaatgtgt gacccagcca tgggcctgcg cgcgagccgg        1020
aactgctcca ggacagagaa cgccgtgtgt ggc                                     1053
```

<210> SEQ ID NO 29
<211> LENGTH: 369
<212> TYPE: PRT
<213> ORGANISM: Artificial Sequence
<220> FEATURE:
<223> OTHER INFORMATION: Whole sequence _ EpCAMscFv-HveA adapter

<400> SEQUENCE: 29

```
Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ser Ser Leu Ser
                20                  25                  30

Ala Ser Val Gly Asp Arg Val Thr Ile Thr Cys Arg Ser Thr Lys Ser
            35                  40                  45

Leu Leu His Ser Asn Gly Ile Thr Tyr Leu Tyr Trp Tyr Gln Gln Lys
        50                  55                  60

Pro Gly Lys Ala Pro Lys Leu Leu Ile Tyr Gln Met Ser Asn Leu Ala
65                  70                  75                  80

Ser Gly Val Pro Ser Arg Phe Ser Ser Ser Gly Ser Gly Thr Asp Phe
                85                  90                  95

Thr Leu Thr Ile Ser Ser Leu Gln Pro Glu Asp Phe Ala Thr Tyr Tyr
            100                 105                 110

Cys Ala Gln Asn Leu Glu Ile Pro Arg Thr Phe Gly Gln Gly Thr Lys
        115                 120                 125

Val Glu Leu Lys Arg Ala Thr Pro Ser His Asn Ser His Gln Val Pro
    130                 135                 140

Ser Ala Gly Gly Pro Thr Ala Asn Ser Gly Thr Ser Gly Ser Glu Val
145                 150                 155                 160

Gln Leu Val Gln Ser Gly Pro Gly Leu Val Gln Pro Gly Gly Ser Val
                165                 170                 175
```

-continued

```
Arg Ile Ser Cys Ala Ala Ser Gly Tyr Thr Phe Thr Asn Tyr Gly Met
            180                 185                 190

Asn Trp Val Lys Gln Ala Pro Gly Lys Gly Leu Glu Trp Met Gly Trp
            195                 200                 205

Ile Asn Thr Tyr Thr Gly Glu Ser Thr Tyr Ala Asp Ser Phe Lys Gly
        210                 215                 220

Arg Phe Thr Phe Ser Leu Asp Thr Ser Ala Ser Ala Ala Tyr Leu Gln
225                 230                 235                 240

Ile Asn Ser Leu Arg Ala Glu Asp Thr Ala Val Tyr Tyr Cys Ala Arg
                245                 250                 255

Phe Ala Ile Lys Gly Asp Tyr Trp Gly Gln Gly Thr Leu Leu Thr Val
            260                 265                 270

Ser Ser Gly Gly Gly Gly Ser Glu Phe Leu Pro Ser Cys Lys Glu Asp
            275                 280                 285

Glu Tyr Pro Val Gly Ser Glu Cys Cys Pro Lys Cys Ser Pro Gly Tyr
        290                 295                 300

Arg Val Lys Glu Ala Cys Gly Glu Leu Thr Gly Thr Val Cys Glu Pro
305                 310                 315                 320

Cys Pro Pro Gly Thr Tyr Ile Ala His Leu Asn Gly Leu Ser Lys Cys
                325                 330                 335

Leu Gln Cys Gln Met Cys Asp Pro Ala Met Gly Leu Arg Ala Ser Arg
            340                 345                 350

Asn Cys Ser Arg Thr Glu Asn Ala Val Cys Gly His His His His
            355                 360                 365

His
```

```
<210> SEQ ID NO 30
<211> LENGTH: 1089
<212> TYPE: DNA
<213> ORGANISM: Artificial Sequence
<220> FEATURE:
<223> OTHER INFORMATION: Whole sequence _ EpCAMscFv-HveA adapter

<400> SEQUENCE: 30
atgagtgtgc ccactcaggt cctggggttg ctgctgctgt ggcttacagg tgccagatgt        60
gatatccaga tgacccagtc cccgtcctcc ctgagtgctt ctgttggtga ccgtgttacc       120
atcacctgcc gttccaccaa atccctcctg cactccaacg gtatcaccta ccttttattgg      180 tatcaacaga aaccgggtaa agctccgaaa cttctgatct accagatgtc caacctggct       240
tccggtgttc cgtctcgttt ctccagttct ggttctggta ccgacttcac cctgaccatc       300
tcttctctgc agccggaaga cttcgctacc tactactgcg ctcagaacct ggaaatcccg       360
cgtaccttcg gtcagggtac caaagttgaa cttaagcgcg ctaccccgtc tcacaactcc       420
caccaggttc atccgcagg cggtccgact gctaactctg aactagtgg atccgaagta         480 cagctggttc agtccggccc gggtcttgtt caacccgggtg gttccgttcg tatctcttgc      540
gctgcttctg gttacacgtt caccaactac ggcatgaact gggtcaaaca ggctccgggt       600
aaaggcctgg aatggatggg ctggatcaac acctacaccg gtgaatccac ctacgctgac       660
tccttcaaag gtcgcttcac tttctccctc gacacaagtg ctagtgctgc atacctccaa       720
atcaactcgc tgcgtgcaga ggatacagca gtctattact gcgcccgttt cgctatcaaa       780
ggtgactact ggggtcaagg cacgctgctg accgtttcct cgggtggtgg cggttcagaa       840
ttcctgccgt cctgcaagga ggacgagtac ccagtgggct ccgagtgctg ccccaagtgc       900
```

-continued

```
agtccaggtt atcgtgtgaa ggaggcctgc ggggagctga cgggcacagt gtgtgaaccc     960
tgccctccag gcacctacat tgcccacctc aatggcctaa gcaagtgtct gcagtgccaa    1020
atgtgtgacc cagccatggg cctgcgcgcg agccggaact gctccaggac agagaacgcc    1080
gtgtgtggc                                                           1089

<210> SEQ ID NO 31
<211> LENGTH: 79
<212> TYPE: DNA
<213> ORGANISM: Artificial Sequence
<220> FEATURE:
<223> OTHER INFORMATION: UL3/4-rpsL-neo_for

<400> SEQUENCE: 31
taaataacac ataaatttgg ctggttgttt gttgtcttta atggaccgcc cgcaaggcct      60
ggtgatgatg gcgggatcg                                                  79

<210> SEQ ID NO 32
<211> LENGTH: 78
<212> TYPE: DNA
<213> ORGANISM: Artificial Sequence
<220> FEATURE:
<223> OTHER INFORMATION: UL3/4-rpsL-neo_rev

<400> SEQUENCE: 32
taggatcccg gccggatcgc gctcgtcacc cgacactgaa acgccccccc ccctcagaa      60 gaactcgtca agaaggcg                                                   78

<210> SEQ ID NO 33
<211> LENGTH: 79
<212> TYPE: DNA
<213> ORGANISM: Artificial Sequence
<220> FEATURE:
<223> OTHER INFORMATION: UL3/4-HM_pCMV_For

<400> SEQUENCE: 33
taaataacac ataaatttgg ctggttgttt gttgtcttta atggaccgcc cgcaatatac      60
gcgttgacat tgattattg                                                  79

<210> SEQ ID NO 34
<211> LENGTH: 78
<212> TYPE: DNA
<213> ORGANISM: Artificial Sequence
<220> FEATURE:
<223> OTHER INFORMATION: UL3/4_bGH_poly_R

<400> SEQUENCE: 34
taggatcccg gccggatcgc gctcgtcacc cgacactgaa acgccccccc ccccgcctca      60
gaagccatag agcccacc                                                   78

<210> SEQ ID NO 35
<211> LENGTH: 13
<212> TYPE: PRT
<213> ORGANISM: Artificial Sequence
<220> FEATURE:
<223> OTHER INFORMATION: HER2scFv _ N terminus linker

<400> SEQUENCE: 35

Ala Ala Ala Ser Ser Gly Gly Gly Ser Gly Ser Gly Gly
1               5                   10

<210> SEQ ID NO 36
```

```
<211> LENGTH: 12
<212> TYPE: PRT
<213> ORGANISM: Artificial Sequence
<220> FEATURE:
<223> OTHER INFORMATION: HER2scFv _ C terminus linker

<400> SEQUENCE: 36

Ser Gly Gly Gly Ser Gly Ser Gly Gly Ala Ala Ala
1               5               10

<210> SEQ ID NO 37
<211> LENGTH: 267
<212> TYPE: PRT
<213> ORGANISM: Artificial Sequence
<220> FEATURE:
<223> OTHER INFORMATION: Whole sequence _ HER2scFv ligand

<400> SEQUENCE: 37

Ala Ala Ala Ser Ser Gly Gly Gly Ser Gly Ser Gly Gly Glu Val Gln
1               5               10              15

Leu Val Glu Ser Gly Gly Gly Leu Val Gln Pro Gly Gly Ser Leu Arg
            20              25              30

Leu Ser Cys Ala Ala Ser Gly Phe Asn Ile Lys Asp Thr Tyr Ile His
        35              40              45

Trp Val Arg Gln Ala Pro Gly Lys Gly Leu Glu Trp Val Ala Arg Ile
    50              55              60

Tyr Pro Thr Asn Gly Tyr Thr Arg Tyr Ala Asp Ser Val Lys Gly Arg
65              70              75              80

Phe Thr Ile Ser Ala Asp Thr Ser Lys Asn Thr Ala Tyr Leu Gln Met
            85              90              95

Asn Ser Leu Arg Ala Glu Asp Thr Ala Val Tyr Tyr Cys Ser Arg Trp
            100             105             110

Gly Gly Asp Gly Phe Tyr Ala Met Asp Tyr Trp Gly Gln Gly Thr Leu
            115             120             125

Val Thr Val Ser Ser Gly Gly Gly Gly Ser Gly Gly Gly Gly Ser Gly
        130             135             140

Gly Gly Gly Ser Asp Ile Gln Met Thr Gln Ser Pro Ser Ser Leu Ser
145             150             155             160

Ala Ser Val Gly Asp Arg Val Thr Ile Thr Cys Arg Ala Ser Gln Asp
            165             170             175

Val Asn Thr Ala Val Ala Trp Tyr Gln Gln Lys Pro Gly Lys Ala Pro
            180             185             190

Lys Leu Leu Ile Tyr Ser Ala Ser Phe Leu Tyr Ser Gly Val Pro Ser
        195             200             205

Arg Phe Ser Gly Ser Arg Ser Gly Thr Asp Phe Thr Leu Thr Ile Ser
    210             215             220

Ser Leu Gln Pro Glu Asp Phe Ala Thr Tyr Tyr Cys Gln Gln His Tyr
225             230             235             240

Thr Thr Pro Pro Thr Phe Gly Gln Gly Thr Lys Val Glu Ile Lys Ser
            245             250             255

Gly Gly Gly Ser Gly Ser Gly Gly Ala Ala Ala
            260             265

<210> SEQ ID NO 38
<211> LENGTH: 801
<212> TYPE: DNA
<213> ORGANISM: Artificial Sequence
<220> FEATURE:
<223> OTHER INFORMATION: Whole sequence _ HER2scFv ligand
```

-continued

```
<400> SEQUENCE: 38
gcggccgcca gtagtggcgg tggctctggt tccggtggag aggtgcagct ggttgaatct      60
ggcggaggac tggttcagcc tggcggatct ctgagactgt cttgtgccgc cagcggcttc     120
aacatcaagg acacctacat ccactgggtc cgacaggccc ctggcaaagg acttgaatgg     180
gtcgccagaa tctaccccac caacggctac accagatacg ccgactctgt gaagggcaga     240
ttcaccatca cgccgacac cagcaagaac accgcctacc tgcagatgaa cagcctgaga     300
gccgaggaca ccgccgtgta ctactgttct agatggggag cgacggctt ctacgccatg     360 gattattggg gccagggcac cctggtcaca gtttctagcg gaggcggagg ttctggcggc     420
ggaggaagtg gtggcggagg ctctgatatc cagatgacac agagccccag cagcctgtct     480
gcctctgtgg gagacagagt gaccatcacc tgtagagcca gccaggacgt gaacacagcc     540
gtggcttggt atcagcagaa gcctggcaag gcccctaagc tgctgatcta cagcgccagc     600
tttctgtaca gcggcgtgcc cagcagattc agcggctcta gaagcggcac cgacttcacc     660
ctgaccataa gcagtctgca gcccgaggac ttcgccacct actactgtca gcagcactac     720
accacacctc caaccttcgg acagggcacc aaggtggaaa tcaagggtgg aggctctggt     780
tccggtggat ccgcggccgc g                                                801

<210> SEQ ID NO 39
<211> LENGTH: 73
<212> TYPE: DNA
<213> ORGANISM: Artificial Sequence
<220> FEATURE:
<223> OTHER INFORMATION: gH29/30-rpsL-neo_For

<400> SEQUENCE: 39
tcgtgggggt tattcttttg ggcgttgcgt ggggtcaggt ccacgactgg ggcctggtga      60
tgatggcggg atc                                                         73

<210> SEQ ID NO 40
<211> LENGTH: 74
<212> TYPE: DNA
<213> ORGANISM: Artificial Sequence
<220> FEATURE:
<223> OTHER INFORMATION: gH29/30-rpsL-neo_Rev

<400> SEQUENCE: 40
ttcgtgtcgc gccagtacat gcggtccatg cccaggccat ccaaaaacca tcagaagaac      60
tcgtcaagaa ggcg                                                        74

<210> SEQ ID NO 41
<211> LENGTH: 22
<212> TYPE: DNA
<213> ORGANISM: Artificial Sequence
<220> FEATURE:
<223> OTHER INFORMATION: gH29/30-scFv_For

<400> SEQUENCE: 41
tcgtgggggt tattcttttg gg                                               22

<210> SEQ ID NO 42
<211> LENGTH: 21
<212> TYPE: DNA
<213> ORGANISM: Artificial Sequence
<220> FEATURE:
<223> OTHER INFORMATION: gH29/30-scFv_Rev
```

<400> SEQUENCE: 42
ttcgtgtcgc gccagtacat g                                                                        21

<210> SEQ ID NO 43
<211> LENGTH: 12
<212> TYPE: PRT
<213> ORGANISM: Artificial Sequence
<220> FEATURE:
<223> OTHER INFORMATION: EpCAMscFv - N terminus linker

<400> SEQUENCE: 43

Ala Ala Ala Ser Ser Gly Gly Gly Ser Gly Ser Gly
1               5                   10

<210> SEQ ID NO 44
<211> LENGTH: 14
<212> TYPE: PRT
<213> ORGANISM: Artificial Sequence
<220> FEATURE:
<223> OTHER INFORMATION: EpCAMscFv - C terminus linker

<400> SEQUENCE: 44

Ser Ser Gly Gly Gly Ser Gly Ser Gly Gly Ser Ala Ala Ala
1               5                   10

<210> SEQ ID NO 45
<211> LENGTH: 280
<212> TYPE: PRT
<213> ORGANISM: Artificial Sequence
<220> FEATURE:
<223> OTHER INFORMATION: Whole sequence - EpCAMscFv ligand

<400> SEQUENCE: 45

Ala Ala Ala Ser Ser Gly Gly Gly Ser Gly Ser Gly Asp Ile Gln Met
1               5                   10                  15

Thr Gln Ser Pro Ser Ser Leu Ser Ala Ser Val Gly Asp Arg Val Thr
                20                  25                  30

Ile Thr Cys Arg Ser Thr Lys Ser Leu Leu His Ser Asn Gly Ile Thr
            35                  40                  45

Tyr Leu Tyr Trp Tyr Gln Gln Lys Pro Gly Lys Ala Pro Lys Leu Leu
        50                  55                  60

Ile Tyr Gln Met Ser Asn Leu Ala Ser Gly Val Pro Ser Arg Phe Ser
65                  70                  75                  80

Ser Ser Gly Ser Gly Thr Asp Phe Thr Leu Thr Ile Ser Ser Leu Gln
                85                  90                  95

Pro Glu Asp Phe Ala Thr Tyr Tyr Cys Ala Gln Asn Leu Glu Ile Pro
            100                 105                 110

Arg Thr Phe Gly Gln Gly Thr Lys Val Glu Leu Lys Arg Ala Thr Pro
        115                 120                 125

Ser His Asn Ser His Gln Val Pro Ser Ala Gly Gly Pro Thr Ala Asn
    130                 135                 140

Ser Gly Thr Ser Gly Ser Glu Val Gln Leu Val Gln Ser Gly Pro Gly
145                 150                 155                 160

Leu Val Gln Pro Gly Gly Ser Val Arg Ile Ser Cys Ala Ala Ser Gly
                165                 170                 175

Tyr Thr Phe Thr Asn Tyr Gly Met Asn Trp Val Lys Gln Ala Pro Gly
            180                 185                 190

Lys Gly Leu Glu Trp Met Gly Trp Ile Asn Thr Tyr Thr Gly Glu Ser
        195                 200                 205

```
Thr Tyr Ala Asp Ser Phe Lys Gly Arg Phe Thr Phe Ser Leu Asp Thr
    210                 215                 220

Ser Ala Ser Ala Ala Tyr Leu Gln Ile Asn Ser Leu Arg Ala Glu Asp
225                 230                 235                 240

Thr Ala Val Tyr Tyr Cys Ala Arg Phe Ala Ile Lys Gly Asp Tyr Trp
                245                 250                 255

Gly Gln Gly Thr Leu Leu Thr Val Ser Ser Ser Ser Gly Gly Gly Ser
                260                 265                 270

Gly Ser Gly Gly Ser Ala Ala Ala
        275                 280
```

```
<210> SEQ ID NO 46
<211> LENGTH: 840
<212> TYPE: DNA
<213> ORGANISM: Artificial Sequence
<220> FEATURE:
<223> OTHER INFORMATION: Whole sequence - EpCAMscFv ligand

<400> SEQUENCE: 46
gcggccgcca gtagtggcgg tggctctggt tccggtgata tccagatgac ccagtccccg      60
tcctccctga gtgcttctgt tggtgaccgt gttaccatca cctgccgttc caccaaatcc     120
ctcctgcact ccaacggtat cacctacctt tattggtatc aacagaaacc gggtaaagct     180
ccgaaacttc tgatctacca gatgtccaac ctggcttccg tgttccgtc tcgtttctcc      240 agttctggtt ctggtaccga cttcaccctg accatctctt ctctgcagcc ggaagacttc     300
gctacctact actgcgctca gaacctggaa atcccgcgta ccttcggtca gggtaccaaa     360
gttgaactta agcgcgctac cccgtctcac aactcccacc aggttccatc cgcaggcggt     420
ccgactgcta actctggaac tagtggatcc gaagtacagc tggttcagtc cggcccgggt     480
cttgttcaac cgggtggttc cgttcgtatc tcttgcgctg cttctggtta cacgttcacc     540
aactacggca tgaactgggt caaacaggct ccgggtaaag cctggaatg atgggctgg       600 atcaacacct acaccggtga atccacctac gctgactcct caaaggtcg cttcactttc      660 tccctcgaca caagtgctag tgctgcatac ctccaaatca actcgctgcg tgcagaggat     720
acagcagtct attactgcgc ccgtttcgct atcaaaggtg actactgggg tcaaggcacg     780
ctgctgaccg tttcctcgtc ttccggtgga ggctctggtt ccggtggatc cgcggccgcg     840
```

```
<210> SEQ ID NO 47
<211> LENGTH: 4
<212> TYPE: PRT
<213> ORGANISM: Artificial Sequence
<220> FEATURE:
<223> OTHER INFORMATION: aminoo acid sequence for Xhol recognition site

<400> SEQUENCE: 47

Leu Glu Glu Leu
1
```

```
<210> SEQ ID NO 48
<211> LENGTH: 12
<212> TYPE: DNA
<213> ORGANISM: Artificial Sequence
<220> FEATURE:
<223> OTHER INFORMATION: Recognition site for Xhol

<400> SEQUENCE: 48
ctcgaggagc tc                                                          12
```

-continued

<210> SEQ ID NO 49
<211> LENGTH: 357
<212> TYPE: PRT
<213> ORGANISM: Artificial Sequence
<220> FEATURE:
<223> OTHER INFORMATION: Whole sequence of Her2scFv-HveA adapter

<400> SEQUENCE: 49

Met Ser Val Pro Thr Gln Val Leu Gly Leu Leu Leu Leu Trp Leu Thr
1               5                   10                  15

Gly Ala Arg Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Val Asn Thr Ala Val Ala Trp Tyr Gln
            180                 185                 190

Gln Lys Pro Gly Lys Ala Pro Lys Leu Leu Ile Tyr Ser Ala Ser Phe
        195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln His Tyr Thr Thr Pro Pro Thr Phe Gly Gln Gly
                245                 250                 255

Thr Lys Val Glu Ile Lys Gly Gly Gly Gly Ser Glu Phe Leu Pro Ser
            260                 265                 270

Cys Lys Glu Asp Glu Tyr Pro Val Gly Ser Glu Cys Cys Pro Lys Cys
        275                 280                 285

Ser Pro Gly Tyr Arg Val Lys Glu Ala Cys Gly Glu Leu Thr Gly Thr
    290                 295                 300

Val Cys Glu Pro Cys Pro Gly Thr Tyr Ile Ala His Leu Asn Gly
305                 310                 315                 320

Leu Ser Lys Cys Leu Gln Cys Gln Met Cys Asp Pro Ala Met Gly Leu
            325                 330                 335

Arg Ala Ser Arg Asn Cys Ser Arg Thr Glu Asn Ala Val Cys Gly His
            340                 345                 350

His His His His His
        355